US008097650B2

(12) United States Patent
Feinmark et al.

(10) Patent No.: US 8,097,650 B2
(45) Date of Patent: Jan. 17, 2012

(54) METHOD OF TREATING A CONDITION ASSOCIATED WITH PHOSPHORYLATION OF TASK-1

(75) Inventors: Steven J Feinmark, Haworth, NJ (US); Richard B Robinson, Cresskill, NJ (US)

(73) Assignee: The Trustees of Columbia University In The City of New York, New York, NY (US)

( * ) Notice: Subject to any disclaimer, the term of this patent is extended or adjusted under 35 U.S.C. 154(b) by 161 days.

(21) Appl. No.: 11/498,343

(22) Filed: Aug. 2, 2006

(65) Prior Publication Data
US 2007/0259051 A1 Nov. 8, 2007

Related U.S. Application Data

(63) Continuation-in-part of application No. 11/495,012, filed on Jul. 27, 2006, now abandoned.

(60) Provisional application No. 60/703,151, filed on Jul. 27, 2005, provisional application No. 60/808,774, filed on May 25, 2006.

(51) Int. Cl.
*A01N 47/10* (2006.01)
*A61K 31/27* (2006.01)
(52) U.S. Cl. ........................ 514/476; 568/305
(58) Field of Classification Search .................. 514/476; 568/305
See application file for complete search history.

(56) References Cited

U.S. PATENT DOCUMENTS

| 5,916,910 A | 6/1999 | Lai |
| 2002/0028485 A1 | 3/2002 | Meadows et al. |
| 2003/0113888 A1 | 6/2003 | Benjamin et al. |
| 2004/0048780 A1 | 3/2004 | Marks |
| 2004/0185519 A1 * | 9/2004 | Gross ........................... 435/19 |
| 2005/0054673 A1 * | 3/2005 | Wirth et al. ................... 514/312 |

FOREIGN PATENT DOCUMENTS

| DE | 103 32 685 | 2/2005 |
| WO | WO0045810 | * 10/2000 |
| WO | WO 01/97798 | 12/2001 |
| WO | WO 2007/014347 | 2/2007 |

OTHER PUBLICATIONS

Kurosawa et al (Intl Archives of Allergy and Immunology vol. 97 Iss 3 (1992) 226-228, abstract only).*
Kennedy (Journal of the National Medical Association, vol. 100, No. 11 (2008) pp. 1260-1270).*
Abas, Lindy et al., "Mitochondrial ATP Production is Necessary for Activation of the Extracellular-Signal-Regulated Kinase during Ischaemia/Reperfusion in Rat Myocyte-Derived H9c2 Cells", Biochemical Journal (2000) vol. 349, pp. 119-126.
Aimond, Franck et al., "Simultaneous Activation of p38 MAPK and p42/44 MAPK by ATP Stimulates the K+ Current I Trek in Cardiomyocytes", Journal of Biological Chemistry (2000), vol. 275:50, pp. 39110-39116.
Andersson, Karl-Erik, et al., Urinary Bladder Contraction and Relaxation: Physiology and Pathophysiology (2004), vol. 84:3, pp. 935-986.
Barbuti, Andrea, et al., Block of the Background K+ Channel TASK-1 Contributes to Arrhythmogenic effects of Platelet-Activating Factor, Am J Physiol Circ Physiol, (2002), vol. 282, pp. H2024-H2030.
Bessana, Alessandra, et al., Activation of Protein Kinase C e Inhibits the Two-pore Domain K+ Channel, TASK-1, Inducing Repolarization Abnormalities in Cardiac Ventricular Myocytes (2004) Journal of Biological Chemistry, vol. 279:32, pp. 33154-33160.
Chalfant, Charles E. et al., "The Structural Requirements for Ceramide Activation of Serine-Threonine Protein Phosphatases", Journal of Lipid Research (2004), vol. 45, pp. 496-506.
Choudhury, Qamrul G., et al., "Investigation into the Involvement of Phospholipases A2 and MAP Kinases in Modulation of AA Release and Cell Growth in A549 Cells", British Journal of Pharmacology (2000), vol. 131:2, pp. 255-265.
Danthi, Sanjay, et al. "Caffeic Acid Esters Active TREK-1 Potassium Channels and Inhibit Depolarization-Dependant Secretion" Molecular Pharmacology (2004), vol. 65:3, pp. 599-610.
de Boer, Ruldolf A. et al., Extracellular Signal Regulated Kinase and SMAD Signalling both Mediate the Angiotensin II Driven Progression Toward Overt Heart Failure in Omozygous TGR(mRen2)27, Journal of Molecular Medicine (2004), vol. 82, pp. 678-687.
Enyeart, John J. et al., "An ACTH- and ATP-Regulated Background K+ Channel in Adrenocortical Cells Is TREK-1", Journal of Biological Chemistry (2002), vol. 277:51, pp. 49186-49199.
Goette, Andreas, et al. "Increased Expression of Extracellular Signal-Regulated Kinase and Angiotensin-Coverting Enzyme in Human Atria During Atrial Fibrillation", Journal of the American College of Cardiology, (2000), vol. 35:6, pp. 1669-1677.
Gruss, Marco et al., "Two-Pore-Domain K+ Channels Are a Novel Target for the Anesthetic Gases Xenon, Nitrous Oxide, and Cyclopropane", Molecular Pharmacology (2004), vol. 65:2, pp. 443-452.
Gruss, Marco et al., "The Two-Pore-Domain K+ Channels TREK-1 and TASK-3 Are Differentially Modulated by Copper and Zinc". Molecular Pharmacology (2004), vol. 66:3, pp. 530-537.
Klein, Gunnar, et al. "Increased Open Probability of Single Cardiac L-type Calcium Channels in Patients with Chronic Atrial Fibrillation: Role of Phosphatase 2A", Cardiovascular Research (2003) vol. 59, pp. 37-45.
Kurosawa, Motohiro, et al., "Effects of Phospholipase A2 Inhibitor ONO-RS-082 on substance P-induced histamine release from Rat Peritoneal Mast Cells", International Archives of Allergy and Immunology (1992) vol. 97, pp. 226-228.
Lauritzen, Inger et al., "Cross-Talk Between the Mechano-gated K2P Channel TREK-1 and the Actin Cytoskeleton", European Molecular Biology Organization (2005), vol. 6:7, 642-654.

(Continued)

*Primary Examiner* — Frederick Krass
*Assistant Examiner* — Benjamin Packard
(74) *Attorney, Agent, or Firm* — Evans & Molinelli PLLC; Judith A. Evans

(57) ABSTRACT

This invention provides methods and compositions for treating a condition associated with phosphorylation of TASK-1 in a subject comprising administering to the subject an amount of an agent effective to overcome the phosphorylation dependent loss of TASK-1 function so as to thereby treat the condition. In a specific embodiment of the invention the agent is a TREK-1 agonist.

10 Claims, 32 Drawing Sheets

OTHER PUBLICATIONS

Mumby, Marc C. et al., "Protein Serine/Threonine Phosphatases: Structure, Regulation, and Functions in Cell Growth", American Physiological Society (1993), vol. 73:4, pp. 673-699.

Ninio, Daniel A., "Dietary Fish Oil Protects Against Stretch-Induced Vulnerability to Atrial Fibrillation in a Rabbit Model", J. Cardiovascular Electrophysiology (2005), vol. 16:11, pp. 1189-1194.

Saint, David A. "Stretch-Activated Channels in the Heart: Their Role In Arrhythmias and Potential as Antiarrhythmic Drug Targets", Drug Development Research (2002), vol. 55, pp. 53-58.

Shen, Garry X. "Selective Protein Kinase C Inhibitors and Their Applications", Current Drug Targets—Cardiovascular & Haematological Disorders (2003), vol. 3:4, pp. 301-307.

Tertyshnikova, Svetlana, et al., "BL-1249[(5,6,7,8-Tetrahydornaphthalen-1-yl)-[2-(1H-tetrazol-5-yl)-phenyl]-amine]: A Putative Potassium Channel Opener with Bladder-Relaxant Properties", Journal of Pharmacology and Experimental Therapeutics, (2005) vol. 313:1 250-259.

ASBMB Annual Meeting, Boston, Jun. 14, 2004, Faseb, J. 18(8):C211 [Abstract].

Ogita, H. et al. "Synthesis and structure-activity relationship of diarylamide derivatives . . . ", Bioorganic & Medicinal Chemistry Letters (2001) vol. 11:4, pp. 549-551.

Search Report dated Oct. 7, 2009 from related EP Application No. 07836321.5.

* cited by examiner

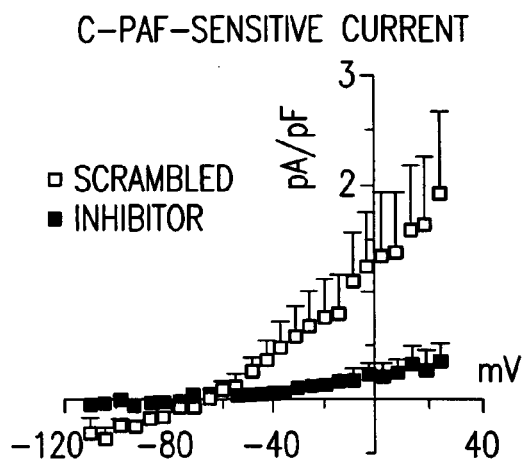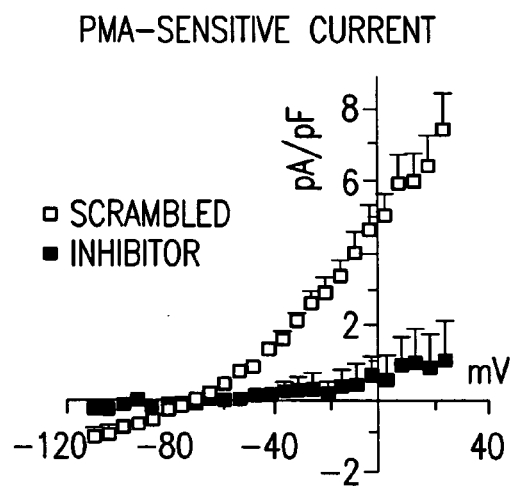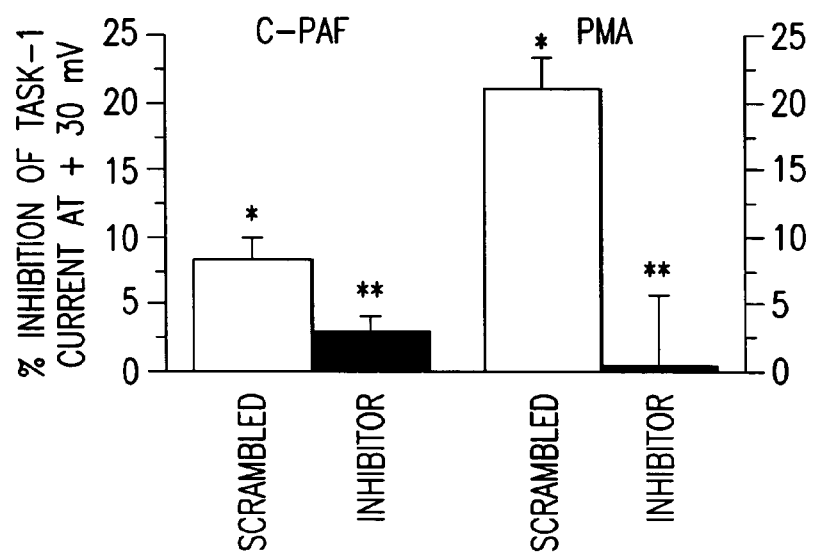
FIG.10A
FIG.10B
FIG.10C

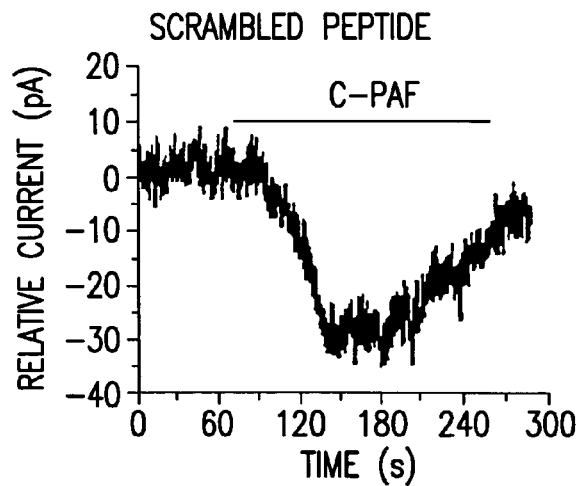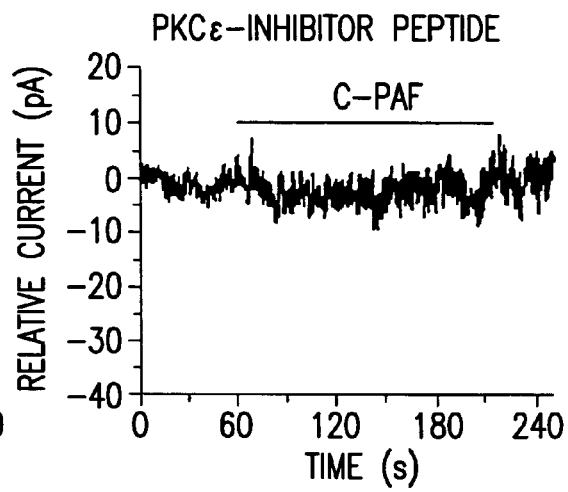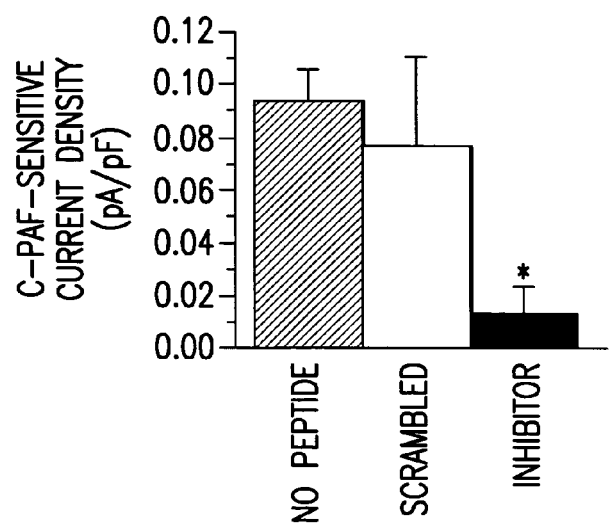

NSR　　　　　AF
TASK-1　
CANINE ATRIUM
TASK-1　
TREK-1　
HUMAN ATRIUM
FIG.17

BML263
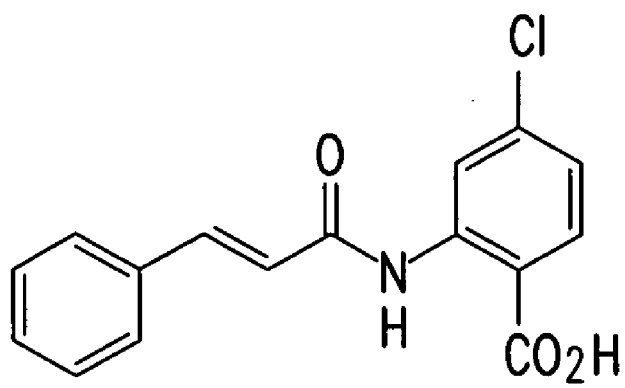
BML264
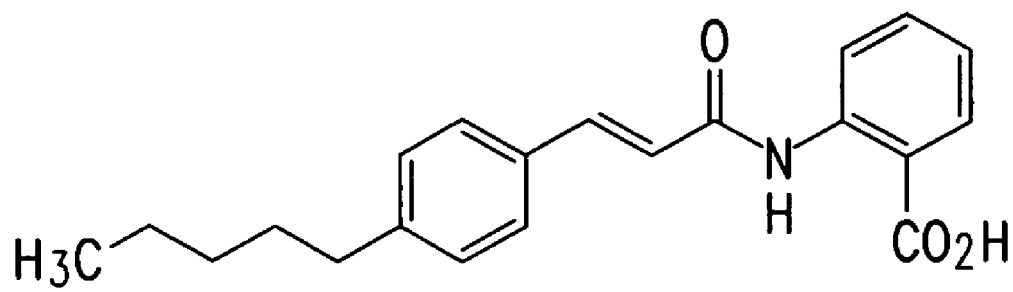
FIG.22A

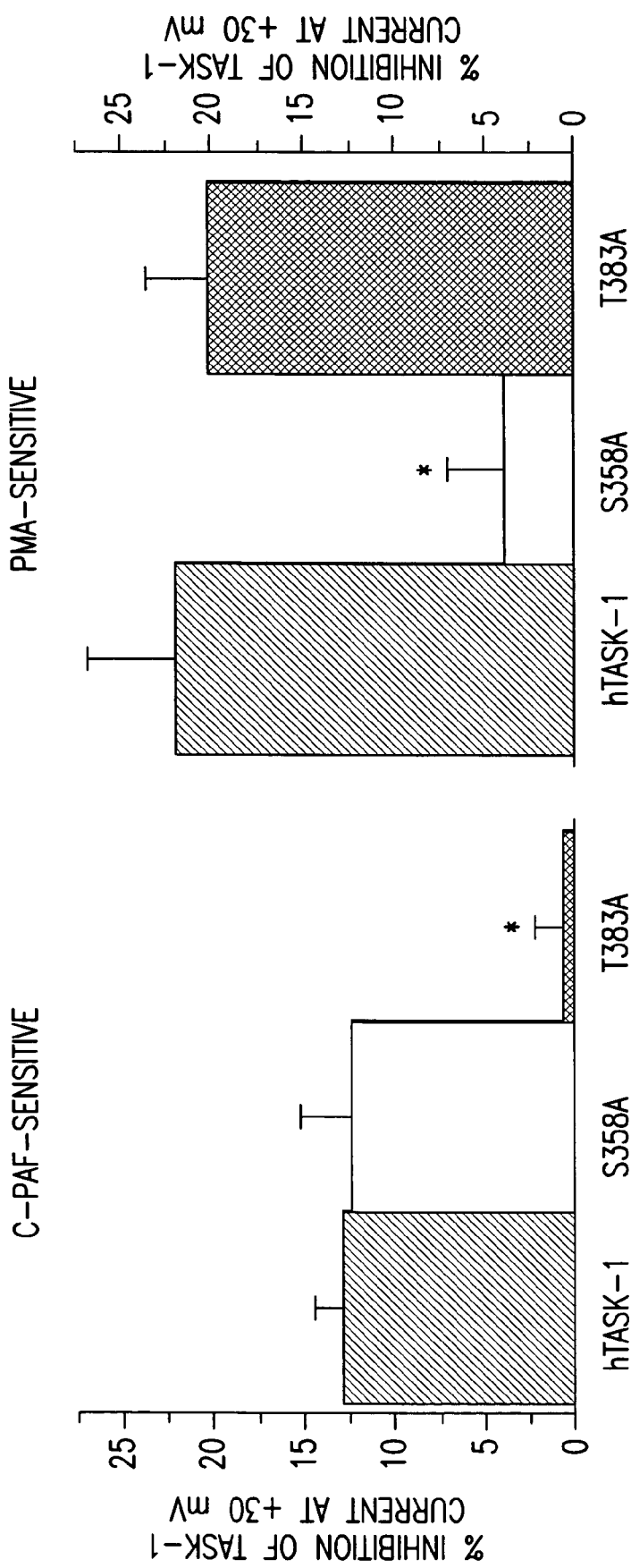

ONO-RS-082 HALTS ATRIAL FIBRILLATION IN THE DOG

NSR

ONO-RS-082 HALTS ATRIAL FIBRILLATION IN THE DOG

AF
AFTER
15 MIN

ONO-RS-082 HALTS ATRIAL FIBRILLATION IN THE DOG

NSR
1 h AFTER
ONO
(0.7 mg/kg)

CONTROL
ONO 100 nM
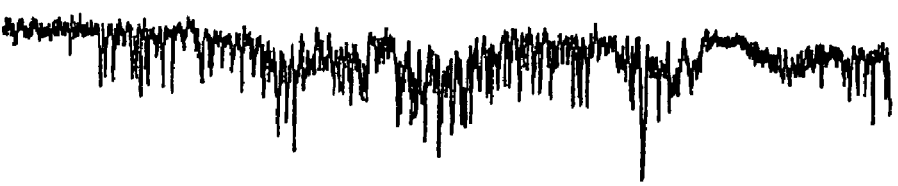
FIG.30

METHOD OF TREATING A CONDITION ASSOCIATED WITH PHOSPHORYLATION OF TASK-1

This application is a continuation-in-part of application Ser. No. 11/495,012, filed Jul. 27, 2006 now abandoned, which claims priority to Application Ser. No. 60/703,151, filed on Jul. 27, 2005, and Application Ser. No. 60/808,774 filed May 25, 2006 each of which is incorporated by reference herein in their entirety.

The invention disclosed herein was made with Government support under Grant No. R01 HL70105 from the National Institutes of Health, and Grant No. HL-56140 from the National Heart, Lung, and Blood Institute. Accordingly, the U.S. Government has certain rights in this invention.

INTRODUCTION

The present invention provides methods and compositions for treating a condition associated with phosphorylation of a human TASK-1 channel in a subject comprising administering to the subject an amount of a compound effective to inhibit phosphorylation of the human TASK-1 channel so as to thereby-restore human TASK-1 channel function and thereby treat the condition.

BACKGROUND OF THE INVENTION

Lethal arrhythmias commonly occur after myocardial ischemia, especially when ischemic myocardium is reperfused. These arrhythmias are usually initiated by ectopic activity triggered by early and delayed after depolarizations (EADs and DADs) of the membrane potential. One consequence of ischemia and reperfusion is a rapid migration of polymorphonuclear leukocytes (PMNL) into the infarcted zone. Activated PMNL bind to activated myocytes and release several substances, including oxygen radicals, proteolytic enzymes and inflammatory lipids that increase the extent of myocardial injury (Lucchesi B R, and Mullane K M. (1986) Annu Rev Pharmacol Toxicol 26: 201-224). Depletion of circulating neutrophils or treatment with anti-inflammatory drugs effectively limits the size of the infarct zone and the extent of the damage in hearts from several species (Lucchesi B R, and Mullane K M. (1986) Annu Rev Pharmacol Toxicol 26: 201-224, Mullane K M et al. (1984) J. Pharmacol. Exp. Ther. 228: 510-522, Romson J L et al. (1983) Circulation 67: 1016-1023).

Hoffman et al. (1997, J Cardiovasc Electrophysiol 8:679-687; 1996, J Cardiovasc Electrophysiol 7:120-133) demonstrated that activation of PMNL bound to isolated canine myocytes dramatically changed the myocyte transmembrane action potential. These changes included prolongation of the action potential duration (APD), EADs and in some cases arrest during the plateau phase of the action potential. It was also shown that direct superfusion of myocytes with the inflammatory phospholipid, platelet-activating factor (PAF) mimicked the action of activated PMNL, and that under similar conditions PMNL produce significant levels of PAF. Furthermore, incubation of myocytes with the PAF receptor (PAFR) antagonist, CV-6209, prevented both PAF- and PMNL-induced changes in myocyte membrane potential. PAF also induces arrhythmias in mice that overexpress the PAFR when the lipid is administered at intravenous doses that have little effect on wild-type animals (Ishii S et al. (1997) EMBO J. 16: 133-142). These observations suggested that PMNL-derived PAF could induce triggered activity and thus ventricular arrhythmias.

There is considerable confusion regarding the molecular mechanisms by which PAF could alter the electrical activity of the heart. Although PAF binds to a cell-surface, G-protein-linked receptor and ultimately increases cytosolic $Ca^{2+}$ levels (Massey C V et al.(1991) J Clin Invest 88: 2106-2116; Montrucchio G et al. (2000) Physiol Rev 80: 1669-1699) little is known about PAF effects on membrane channels. Wahler et al. showed that subnanomolar concentrations of PAF markedly decreased the inwardly rectifying potassium channel $IK_1$ in guinea pig ventricular myocytes (Wahler G M et al. (1990) Mol Cell Biochem 93: 69-76), while Hoffman et al. suggested that depolarizing $Na^+$ current may play a role in the arrhythmogenic action of PAF (Hoffman, B F et al. (1996) J Cardiovasc Electrophysiol 7:120-133).

Here, employing genetically modified mice in which PAFR have been knocked out (Ishii S et al. (1998) T, J Exp Med 187: 1779-1788), the ability of carbanyl-PAF (C-PAF), a non-metabolizable PAF analogue, to alter the membrane potential of isolated murine ventricular myocytes has been tested with the intent of clarifying the mechanisms determining the arrhythmogenic effects of this lipid. It is disclosed here that PAF-mediated cardiac electrophysiologic effects are linked to inhibition of the two-pore domain $K^+$ channel, TASK-1.

In addition, the molecular mechanism of the C-PAF effect on TASK-1 current is elucidated by identifying the epsilon isoform of PKC (PKCε) as a critical component in PAFR signaling. Furthermore, using site-directed mutagenesis, the critical residue that is the target for PKC in the murine and human channels is identified. Finally, data is presented here showing that the phosphorylation-dependent disruption of TASK-1 current also occurs in a rapid-pacing model of atrial fibrillation and in peri-operative atrial fibrillation.

SUMMARY OF THE INVENTION

The present invention provides a method of treating a condition associated with phosphorylation of a human TASK-1 channel in a subject comprising administering to the subject an amount of a compound effective to inhibit phosphorylation of the human TASK-1 channel so as to thereby-restore human TASK-1 channel function and thereby treat the condition. In a preferred embodiment of the invention, phosphorylation of amino acid residue S358 and/or T383 of the human TASK-1 channel is inhibited.

This invention also provides a method of treating a condition associated with phosphorylation of a human TASK-1 channel in a subject comprising administering to the subject an amount of a compound effective to dephosphorylate amino acid residue S358 and/or T383 of the human TASK-1 channel so as to thereby restore human TASK-1 channel function and thereby treat the condition.

The present invention further provides a method of treating a condition associated with phosphorylation of a TASK-1 channel in a subject comprising administering to the subject an amount of a TREK-1 channel agonist effective to overcome the phosphorylation dependent loss of TASK-1 function so as to thereby treat the condition.

This invention also provides a method of identifying an agent that induces activation of a human TREK-1 comprising: (a) providing a cell expressing the human TREK-1 in a membrane of the cell; (b) measuring current produced by the human TREK-1 at a predetermined membrane potential; (c) contacting the human TREK-1 with the agent; and (d) measuring current produced by the human TREK-1 at the predetermined membrane voltage in the presence of the agent, wherein an increase in current measured in step (d) as compared to step (b) indicates that the, agent induces activation of human TREK-1.

BRIEF DESCRIPTION OF THE DRAWINGS

FIGS. 10A-10C. The activation of PKCε decreases TASK-1 current in CHO cells. C-PAF- and PMA-sensitive currents were obtained from CHO cells transfected with murine TASK-1 in whole cell configuration using a ramp protocol as described in the legend to FIG. 9. In these experiments, the patch pipette contained either a PKCε-specific inhibitor peptide or a scrambled peptide (100 nM, in the pipette solution). The inhibitor peptide blocked the effect of C-PAF (185 nM, n=8, 10A, filled symbols) and PMA (100 nM, n=10, 10B, filled symbols) while the scrambled peptide had no effect on either C-PAF (n=10, 10A, open symbols) or PMA (n=11, 10B, open symbols). The percent inhibition in each case was measured at +30 mV by comparison of each cell before and after drug (10C). C-PAF and PMA significantly inhibit TASK-1 current in the presence of the scrambled peptide (*, p<0.05, t-test, comparing control to drug treated in the presence of scrambled peptide). Neither C-PAF nor PMA had a significant effect on the current in presence of the inhibitor peptide (not significant versus control) and the effect of both drugs on TASK-1 current was significantly reduced by the inhibitor peptide (, p<0.05, t-test, comparing drug in the presence of scrambled peptide to drug in the presence of inhibitor peptide). All the recordings started 8-10 min after the rupture of the membrane and the drugs were applied after the current was stable for at least 1 min. Drug treatment and calculation of the drug-sensitive currents were done as described in the legend to FIG. 9**.

FIGS. 11A-11C. The C-PAF dependent inhibition of TASK-1 current in mouse ventricular myocytes requires activation of PKCε. Steady-state current measurement. 11A. In voltage clamp, myocytes were held at −10 mV, dialyzed with scrambled peptide, and superfused with C-PAF (185 nM) for 2 min. This treatment causes an inhibition of an outward $K^+$-selective current previously identified as TASK-1 (Besana et al., 2004 J. Biol. Chem., 279 (32), 33154-33160). 11B. In the presence of the PKCε-inhibitor peptide (100 nM in the pipette solution), C-PAF was unable to affect the current. 11C. The C-PAF-sensitive current was not different from zero (*, p<0.05, comparing the C-PAF-sensitive current in the presence of inhibitor peptide, n=4, to no peptide, n=25, or scrambled peptide, n=4). In the typical traces shown in 10A and 10B the baseline outward holding current was adjusted to zero to illustrate the C-PAF-sensitive current. The holding current in 11A and 11B was 125 pA and 76 pA, respectively. The recordings started 10-12 min after the rupture of the membrane. C-PAF was applied after the current was stable for at least 1 min.

FIG. 17. Western blot analysis of 2PK channel expression in dog and human heart. Membrane fractions were prepared from atria of hearts that were either in normal sinus rhythm (NSR) or in chronic atrial fibrillation (AF). Equal amounts of protein were loaded to each lane and the mixtures were separated by SDS-PAGE. Proteins in the gel were transferred to nitrocellulose and the blot was probed with anti-TASK-1 and anti-TREK-1. The signal was detected with an enhanced ECL system.

FIG. 22A-B. 22A. Structure of ONO-RS-082 analogues BML263 and BML264. 22B. Activity of analogues of ONO-RS-082. hTREK-1 channel was expressed and current measured as described in FIG. 21. The change in current was measured after cells were perfused with varying doses of the drugs as noted in the Figure.

FIGS. 24A-24B. Mutations in human TASK-1 remove the sensitivity to C-PAF and PMA when the channel is expressed in CHO cells. Two human TASK-1 (hTASK-1) mutants in which either serine-358 was converted to alanine (S358A) or threonine-383 was converted to alanine (T383A) were generated and separately expressed in CHO cells. The C-PAF-sensitive (24A) and PMA-sensitive currents (24B) were obtained in Tyrode's at pH 8 using a ramp protocol in whose cell configuration, essentially as described in FIG. 15. The mutant channels displayed normal current in amplitude, sensitivity to pH, reversal potential and shape. However, the S358A channel was not inhibited in the presence of C-PAF (24A) and the T383A channel was not inhibited by PMA (24B).

FIG. 30. ONO-RS-082 activates TREK-1 in a cell-free patch: single channel recordings. CHO cells were transfected with a plasmid that encodes the human TREK-1 channel. 48 h after transfection cells were used in the patch clamp experiments. Single channel recordings were obtained in the inside-out configuration holding the patch at −80 mV in symmetrical $K^+$ (155 mM). Panel A shows a typical recording of the channel openings in CHO cell membrane under control conditions. Panel B shows an increase in single channel activity 1 min 30 s after perfusion of the patch with 100 nM ONO. This result is typical of at least 4 patches.

DETAILED DESCRIPTION OF THE INVENTION

Figure 1:
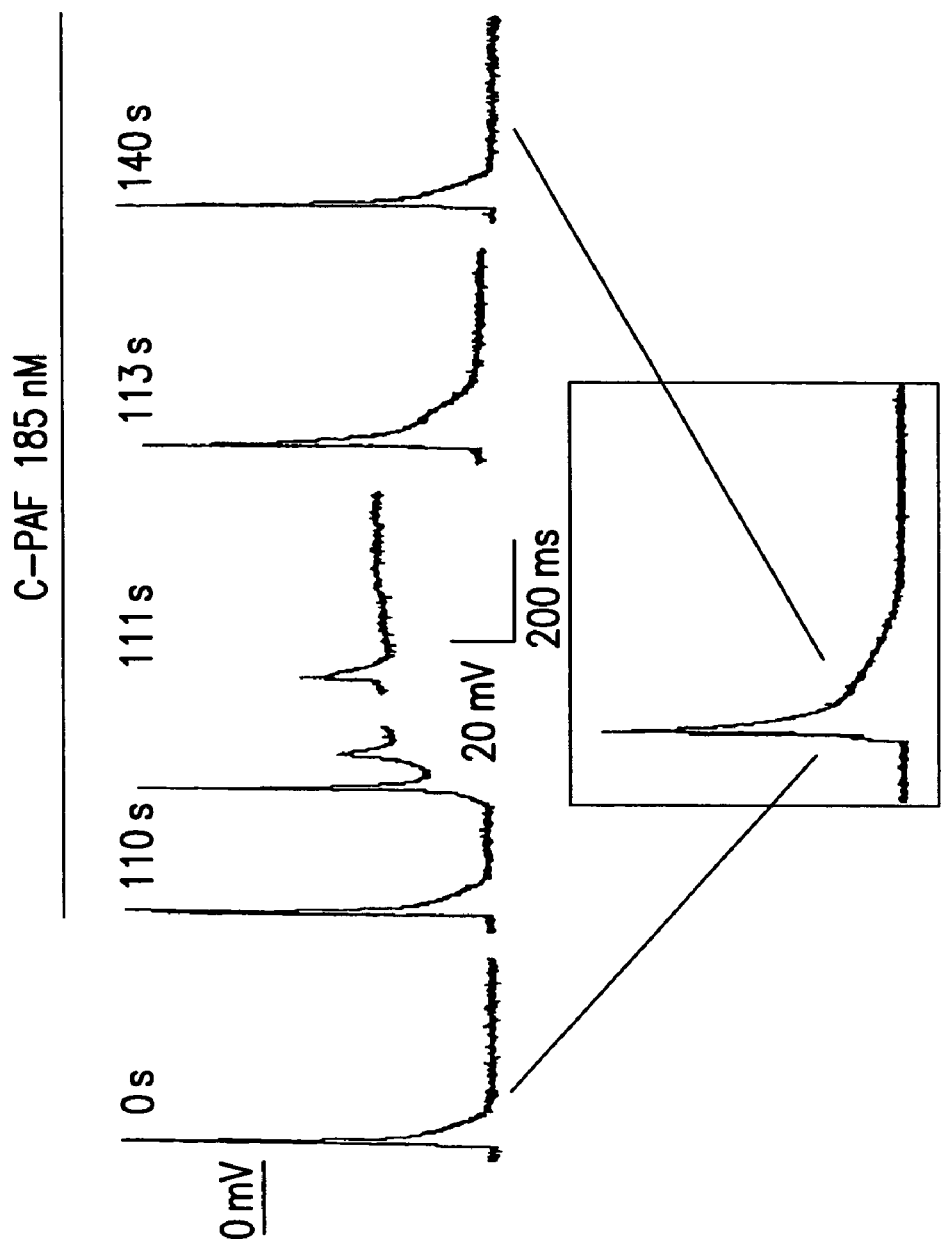
FIG. 1. C-PAF alters normal action potentials in mouse ventricular myocytes. Paced action potentials (cycle length 1000 ms) were recorded in current clamp mode under control conditions (left trace, 0 s) and after perfusion of C-PAF (185 nM;). After a delay, C-PAF caused abnormal automaticity (trace 2, 110 s) and sustained depolarization (trace 3, 111 s). The action potential progressively shortened and normal rhythm was re-established, indicating desensitization of the receptor in continuous presence of drug (traces 4 and 5, 113 s and 140 s). The inset shows that traces during control perfusion and after recovery completely overlap. The data in this figure are derived from a single cell and are typical of 8 cells. The traces were recorded immediately before the application of C-PAF (trace 1) and 110, 111, 113, and 140 s after C-PAF (traces 2 through 5).

The following abbreviations are used in the specification:
AP, action potential;
PKC, protein kinase C;
PMA, phorbol 12-myristate 13-acetate;
PAF, platelet-activating factor;
C-PAF, carbamyl-platelet-activating factor;
PAFR, platelet-activating factor receptor;
CHO, Chinese hamster ovary cells;
TASK-1, TWIK-related, acid-sensitive potassium channel-1;
TREK-1, TWIK-1 related K channel;
BIM-I, bisindoylmaleimide I;
KO, knockout;
WT, wild-type;
TEA, tetraethylammonium; and
EAD, early after depolarizations.

The present invention provides a method of treating a condition associated with phosphorylation of TASK-1 in a subject, or with current loss, preferably a mammal, e.g. a human being, a dog, a rat or a mouse, comprising administering to the subject an amount of a TREK-1 agonist effective to overcome the phosphorylation dependent loss of TASK-1 function, or current loss, so as to thereby treat the condition.

As used herein, "TASK-1" is a TWIK-related, acid-sensitive potassium channel-1, one of a family of TASK channels found in mammals as reported for example in Duprat, F. et al. (EMBO J. 1997 16:5464-5471); and Patel, A. J. et al. (Nat. Neurosci. 1999, 2 (5), 422-426); e.g. Genbank No. 014649; and Besana, A. et al. (J. Biol. Chem., 2004, 279 (32), 33154-33160).

As used herein, "TASK-1 function" means the background or "leak" outward potassium current carried by TASK-1 channels in myocytes functional in repolarization. Inhibition of this function delays repolarization of the myocyte and destabilizes the resting potential.

As used herein, "TREK-1 agonist" is a compound which activates a TREK-1 potassium current. Such a current may be outwardly rectifying. TREK-1 potassium currents are exemplified in Fink et al., (EMBO J. 1996 Dec. 16; 15:6854-62).

This invention also provides a method of preventing a condition associated with phosphorylation of TASK-1 in a subject comprising administering to the subject an amount of a TREK-1 agonist effective to overcome phosphorylation dependent loss of TASK-1 function so as to thereby prevent the condition.

In such methods the amount effective to overcome phosphorylation dependent loss of TASK-1 function may readily be determined by methods well known to those skilled in the art. The appropriate concentration of the composition of the invention which will be effective in the treatment of a particular cardiac disorder or condition will depend on the nature of the disorder or condition, and can be determined by one of skill in the art using standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose response curves derived from in vitro or animal model test systems. Additionally, the administration of the compound could be combined with other known efficacious drugs if the in vitro and in vivo studies indicate a synergistic or additive therapeutic effect when administered in combination.

In an embodiment of the invention, an effective amount is a dose between 0.01 and 100 mg/kg body weight of the subject per day, more typically between 10 mg/kg and 50 mg/kg body weight of the subject per day.

In one embodiment of this invention the condition associated with phosphorylation of TASK-1 is a cardiovascular disorder, such as in atrial fibrillation, particularly peri-operative atrial fibrillation. In another embodiment of this invention the condition associated with phosphorylation of TASK-1 is a ventricular arrhythmia, such as a post-ischemic arrhythmia.

The present invention further relates to pharmaceutical compositions comprising a TREK-1 agonist and a pharmaceutically acceptable carrier in an amount effective to overcome phosphorylation dependent loss of TASK-1 function. As used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. The composition can be formulated as a suppository, with traditional binders and carriers such as triglycerides. Oral formulation can include standard carvers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical sciences" by E. W. Martin. Such compositions will contain a therapeutically effective amount of the therapeutic compound, preferably in purified form, together with a suitable amount of carrier so as to provide the form for proper administration to the patient. The formulation should suit the mode of administration.

In certain embodiments of the invention the TREK-1 agonist is a lipid, a lipoxygenase metabolite of arachidonic acid or linoleic acid, anisomycin, riluzole, a caffeic acid ester, a tyrphostin, nitrous oxide, propranolol, xenon, cyclopropane, adenosine triphosphate, or copper. In one such embodiment the tyrphostin is tyrphostin 47.

In other embodiments of this invention the TREK-1 agonist has one of the following structures:

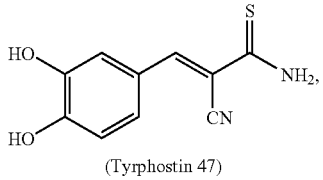
(Tyrphostin 47)

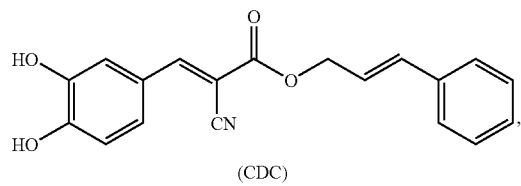
(CDC)

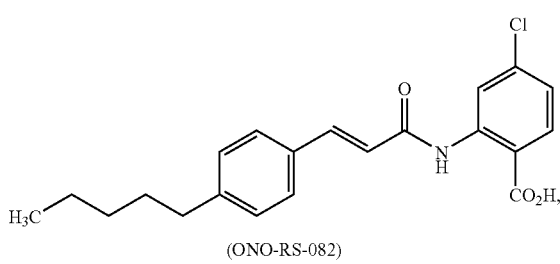
(ONO-RS-082)

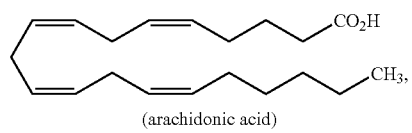
(arachidonic acid)

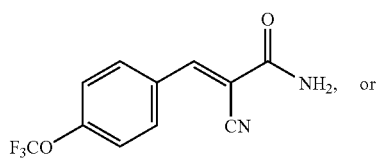

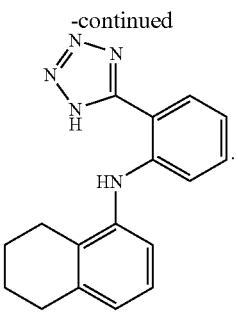

In one embodiment of this invention the TREK-1 agonist is (5, 6, 7, 8-Tetrahydro-naphthalen-1-yl)-[2-(1H-tetrazol-5-yl)-phenyl]-amine.

In one embodiment of the present invention, the TREK-1 activator may be a compound of the formula I:

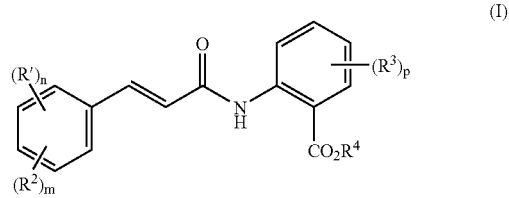
(I)

or a pharmaceutically acceptable ester, salt or hydrate thereof wherein:

each $R^1$ is independently selected from the group consisting of halo, $CF_3$, $NO_2$, $NH_2$, and CN;

each $R^2$ is independently selected from the group consisting of
— $C_1$ to $C_8$ alkyl,
— $C_2$ to $C_8$ alkenyl,
—O—($C_1$ to $C_8$ alkyl),
—NH($C_1$ to $C_8$ alkyl),
—C(=O)—($C_1$ to $C_8$ alkyl),
—O—C(=O)—($C_1$ to $C_8$ alkyl),
—C(=O)—O—($C_1$ to $C_8$ alkyl),
—C(=O)—NH—($C_1$ to $C_8$ alkyl), and
—NH—C(=O)—($C_1$ to $C_8$ alkyl),
wherein each $C_1$ to $C_8$ alkyl and $C_2$ to $C_8$ alkenyl may be branched or unbranched and may be optionally substituted with one or more substituents selected from the group consisting of halo, lower alkoxy, oxo, CN, $NO_2$, $NH_2$, NH-(lower alkyl), N(lower alkyl)$_2$, cycloalkyl, aryl, and a heterocyclic group;

each $R^3$ is independently selected from the group consisting of halo, lower alkyl, lower alkoxy, $NH_2$, NH-(lower alkyl), N(lower alkyl)$_2$, $NO_2$, CN, $CF_3$, and;

$R^4$ is selected from the group consisting of H and lower alkyl;

n=0 to 2;

m=0–2; and p=0 to 2.

In preferred embodiments, n=0, and m=1. In further embodiments $R_2$ is $C_1$ to $C_8$ alkyl, and preferably is in the meta or para position and most preferably in the para position.

In certain embodiments of the present invention, the TREK-1 activator may be a compound of the formula II:

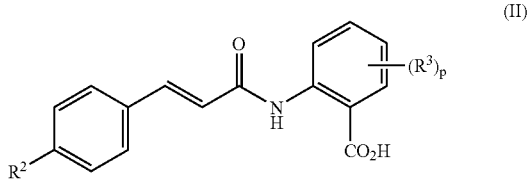

(II)

or a pharmaceutically acceptable ester, salt or hydrate thereof wherein:

$R^2$ selected from the group consisting of
- $C_1$ to $C_8$ alkyl,
- $C_2$ to $C_8$ alkenyl,
- O—($C_1$ to $C_8$ alkyl),
- NH($C_1$ to $C_8$ alkyl),
- C(=O)—($C_1$ to $C_8$ alkyl),
- O—C(=O)—($C_1$ to $C_8$ alkyl),
- C(=O)—O—($C_1$ to $C_8$ alkyl),
- C(=O)—NH—($C_1$ to $C_8$ alkyl), and
- NH—C(=O)—($C_1$ to $C_8$ alkyl),
  wherein each $C_1$ to $C_8$ alkyl and $C_2$ to $C_8$ alkenyl may be branched or unbranched and may be optionally substituted with one or more substituents selected from the group consisting of halo, lower alkoxy, oxo, CN, $NO_2$, $NH_2$, NH-(lower alkyl), N(lower alkyl)$_2$, cycloalkyl, aryl, and a heterocyclic group;

each $R^3$ is independently selected from the group consisting of halo, lower alkyl, lower alkoxy, $NH_2$, NH-(lower alkyl), N(lower alkyl)$_2$, $NO_2$, CN, $CF_3$, and;

$R^4$ is selected from the group consisting of H and lower alkyl; and p=0 to 2.

All value ranges, for example those given for n and m, are inclusive over the entire range. Thus, a range of 0 to 2 would include the values 0, 1, and 2.

It is understood that when n is a value greater than 1, each $R^1$ group may be selected independently. Thus, when more than one $R^1$ group is present, the $R^1$ groups may be selected from any of the stated groups so as to be the same or different. This also holds true for any other group or substituent which may be selected independently from among various groups or values.

The term "halo" or "halogen" as used herein includes fluorine, chlorine, bromine and iodine.

The term "lower alkyl" as used herein contemplates both straight and branched chain alkyl radicals containing from one to six carbon atoms and includes methyl, ethyl, propyl, isopropyl, butyl, isobutyl, tert-butyl, and the like.

The term "lower alkoxy" as used herein contemplates a group having the structure —O-(lower alkyl), which is bonded as a substituent through the oxygen atom.

The term "cycloalkyl" as used herein contemplates substituted or unsubstituted cyclic alkyl radicals containing form 3 to 7 carbon atoms and includes cyclopropyl, cyclopentyl, cyclohexyl, and the like.

The term "heterocyclic group" or "heterocyclic ring" as used herein contemplates substituted or unsubstituted aromatic and non-aromatic cyclic radicals having at least one heteroatom as a ring member. The term "heteroatom" refers to O, N, and S. Preferred heterocyclic groups are those containing 5 or 6 ring atoms which includes at least one hetero atom, and includes cyclic amines such as morpholino, piperidino, pyrrolidino, and the like, and cyclic ethers, such as tetrahydrofuran, tetrahydropyran, and the like. Aromatic heterocyclic groups, also termed "heteroaryl" groups contemplates single-ring hetero-aromatic groups that may include from one to three heteroatoms, for example, pyrrole, furan, thiophene, imidazole, oxazole, thiazole, triazole, pyrazole, pyridine, pyrazine, pyridazine, pyrimidine, and the like. The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles and/or heteroaryls. Examples of polycyclic heteroaromatic systems include quinoline, isoquinoline, tetrahydroisoquinoline, quinoxaline, quinaxoline, benzimidazole, benzofuran, purine, imidazopyridine, benzotriazole, and the like. A heterocyclic group may be optionally substituted with one or more substituents selected from halo, lower alkyl, lower alkoxy $CF_3$, CN, $NH_2$, and $NO_2$.

The terms "aryl", "aromatic group", or "aromatic ring" as used herein contemplates substituted or unsubstituted single-ring aromatic groups (for example, phenyl, pyridyl, pyrazole, etc.) and polycyclic ring systems (naphthyl, quinoline, etc.). The polycyclic rings may have two or more rings in which two atoms are common to two adjoining rings (the rings are "fused") wherein at least one of the rings is aromatic, e.g., the other rings can be cycloalkyls, cycloalkenyls, aryl, heterocycles and/or heteroaryls. The aryl group may be optionally substituted with one or more substituents selected from halo, lower alkyl, lower alkoxy $CF_3$, CN, $NH_2$, and $NO_2$.

In a specific embodiment of the invention compounds of formula (I) and/or (II) include, for example, ONO-RS-32 and ONO-RS-32 analogues as depicted in FIG. 22A.

In another embodiment of the invention, the TREK-1 agonist is a non-narcotic analgesics/non-steroidal anti-inflammatory drugs (NSAIDs). Such, NSAIDs include those having the following general structure:

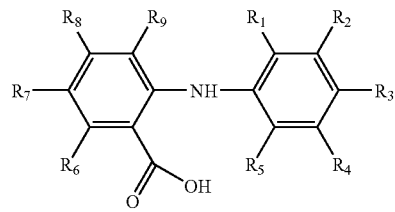

where $R_1$-$R_9$ may be the same or different and are selected from the group consisting of hydrogen, halogen, alkyl, or haloalkyl. The free —COOH group may also be in the form of a pharmaceutically acceptable salt or ester. In a specific embodiment of the invention, Meclofenamic acid having the molecular formula $C_{14}H_{11}Cl_2O_2N$ and the following chemical structure:

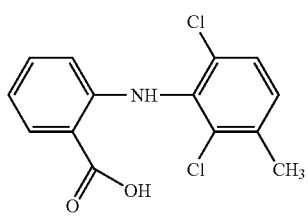

may be used as a TREK-1 agonist. Additional compounds that may be used as TREK-1 agonist include, for example, naproxen, sulindac, nimesulide and ibuprofen.

This invention also provides a method of treating a condition in a subject which condition is alleviated by activation of TREK-1 which comprises administering to the subject an amount of a compound having the following structure effective to activate TREK-1 and thereby alleviate the condition:

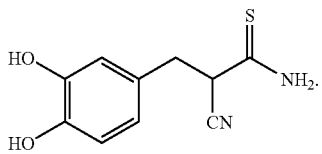

Additionally, the method of treating a condition in a subject which condition is alleviated by activation of TREK-1 comprises administering to the subject any of the TREK-1 agonists disclosed herein in an amount effective to activate TREK-1 and thereby alleviate the condition.

It should be understood that compounds capable of modulating TREK-1 activity, as disclosed herein, include functional derivatives and analogs, including pharmaceutically acceptable salts, esters, or hydrates thereof.

In the context of the invention, preference is given to pharmaceutically acceptable salts. "Pharmaceutically acceptable salts" refers to an acid addition salt or a basic addition salt of a compound of the invention in which the resulting counter ion is understood in the art to be generally acceptable for pharmaceutical uses. Pharmaceutically acceptable salts can be salts of the compounds according to the invention with inorganic or organic acids. Preference is given to salts with inorganic acids, such as, for example, hydrochloric acid, hydrobromic acid, phosphoric acid or sulfuric acid, or to salts with organic carboxylic or sulfonic acids, such as, for example, acetic acid, maleic acid, fumaric acid, malic acid, citric acid, tartaric acid, lactic acid, benzoic acid, or methanesulfonic acid, ethanesulfonic acid, phenylsulfonic acid, toluenesulfonic acid or naphthalenedisulfonic acid. Pharmaceutically acceptable salts can also be metal or ammonium salts of the compounds according to the invention. Particular preference is given to, for example, sodium, potassium, magnesium or calcium salts, and also to ammonium salts which are derived from ammonia or organic amines, such as, for example, ethylamine, di- or triethylamine, di- or triethanolamine, dicyclohexylamine, dimethylaminoethanol, arginine, lysine, ethylenediamine or 2-phenylethylamine. (see, Berge et al. *J. Pharm. Sci.* 1977, 66, 1-19.)

The substances according to the invention may also be present as pharmaceutically acceptable ester, such as the methyl ester, ethyl ester and the like.

When one or more chiral centers are present in the compounds of the present invention, the individual isomers and mixtures thereof (e.g., racemates, etc.) are intended to be encompassed by the formulae depicted herein. In certain embodiments, compounds of the invention may exist in several tautomeric forms. Accordingly, the chemical structures depicted herein encompass all possible tautomeric forms of the illustrated compounds. Compounds of the invention may exist in various hydrated forms.

The present invention further provides methods, as described below, for the identification of compounds that may, through their interaction with the TREK-1 gene or TREK-1 gene product, affect the activity of TREK-1. It is also within the scope of the present invention that such methods may be used equally as well for the identification of compounds that may, through their interaction with the TASK-1 gene or TASK-1 gene product, affect the activity of TASK-1.

The following assays are designed to identify: (i) compounds that bind to TREK-1 gene products; (ii) compounds that bind to other intracellular proteins that interact with a TREK-1 gene product; and (iii) compounds that modulate the activity of TREK-1 gene (i.e., modulate the level of TREK-1 gene expression and/or modulate the level of TREK-1 gene product activity). Compounds identified via assays such as those described herein may be useful, for example, in elaborating the biological functions of the TREK-1 gene product, and for treating cardiovascular disorders, including but not limited to atrial fibrillation, peri-operative atrial fibrillation or ventricular arrythmia. It is to be noted that the compositions of the invention include pharmaceutical compositions comprising one or more of the compounds identified via such methods.

Assays may be utilized which identify compounds which bind to TREK-1 gene regulatory sequences (e.g., promoter sequences) and which may modulate the level of TREK-1 gene expression. Such methods for identifying compounds that modulate TREK-1 gene expression, comprise, for example: (a) contacting a test compound with a cell or cell lysate containing a reporter gene operatively associated with a TREK-1 gene regulatory element; and (b) detecting expression of the reporter gene product. Also provided is another method for identifying compounds that modulate TREK-1 gene expression comprising: (a) contacting a test compound with a cell containing TREK-1 transcripts; and (b) detecting the translation of the TREK-1 transcript. Any reporter gene known in the art can be used, such as but not limited to, green fluorescent protein, β-galactosidase, alkaline phosphatase, chloramphenicol acetyltransferase, etc.

In yet another embodiment of the invention, in vitro systems may be designed to identify compounds capable of interacting with, e.g., binding to, the TREK-1 gene product. Such compounds may be useful, for example, in modulating the activity of TREK-1 gene product, in elaborating the biological function of the TREK-1 gene product, or may be utilized in screens for identifying compounds that modulate normal TREK-1 gene product interactions.

The principle of the assays used to identify compounds that interact with the TREK-1 gene product involves preparing a reaction mixture of the TREK-1 gene product, or fragments thereof and the test compound under conditions and for a time sufficient to allow the two components to interact with, e.g., bind to, thus forming a complex, which can represent a transient complex, which-can be removed and/or detected in the reaction mixture. These assays can be conducted in a variety of ways. For example, one method to conduct such an assay would involve anchoring TREK-1 gene product or the test substance onto a solid phase and detecting TREK-1 gene product/test compound complexes anchored on the solid phase at the end of the reaction. In one embodiment of such a method, the TREK-1 gene product or fragment thereof may be anchored onto a solid surface, and the test compound, which is not anchored, may be labeled, either directly or indirectly.

In yet another embodiment of the invention, displacement assays may be used to identify compounds that interact with the TREK-1 gene product, or fragments thereof. The assay is based on the ability of such compounds to displace or preventing binding of compounds known to interact with the TREK-1 gene product or fragments thereof.

The basic principle of the displacement assay system used to identify compounds that interact with the TREK-1 gene product or fragments thereof involves preparing a reaction mixture containing the TREK-1 gene product, or fragments thereof, and the compound know to bind to TREK-1 under conditions and for a time sufficient to allow the two to interact and bind, thus forming a complex. In order to test a compound for inhibitory activity, the reaction mixture is prepared in the presence and absence of the test compound. The test compound may be initially included in the reaction mixture, or may be added at a time subsequent to the addition of TREK-1 gene product and its intracellular interacting partner. Control reaction mixtures are incubated without the test compound or with a placebo. The formation of any complexes between the TREK-1 gene product or fragments thereof and the compound known to bind to TREK-1 is then detected. The formation of a complex in the control reaction, but not in the reaction mixture containing the test compound, indicates that the compound interferes with the interaction of the TREK-1 gene product and the compound known to bind to TREK-1.

The assay for compounds that interfere with the interaction of the TREK-1 gene product and compounds known to bind to TREK-1 can be conducted in a heterogeneous or homogeneous format. Heterogeneous assays involve anchoring either the TREK-1 gene product or the compound known to bind to TREK-1 onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the TREK-1 gene products and the compounds known to bind to TREK-1, e.g., by competition, can be identified by conducting the reaction in the presence of the test substance; i.e., by adding the test substance to the reaction mixture prior to or simultaneously with the TREK-1 gene protein and compound known t bind to TREK-1. Alternatively, test compounds that disrupt preformed complexes, e.g. compounds with higher binding constants that displace one of the components from the complex, can be tested by adding the test compound to the reaction mixture after complexes have been formed.

In a specific embodiment of the invention, compounds known to bind to TREK-1, that may be used in the practice of the invention include, for example, ONO-RS-082, BML263 and BML264. To facilitate the detection of such compounds, the compounds may be radioactively or fluorescently labeled.

In a specific embodiment of the invention, membrane preparations derived from cells known to express TREK-1, or genetically engineered to express TREK-1, may be used in the displacement assays of the invention. In yet another embodiment of the invention, membrane preparations may be derived from tissues derived from transgenic animals engineered to expressTREK-1.

In practice, microtitre plates may conveniently be utilized as the solid phase. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the previously nonimmobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for TREK-1 gene product or the test compound to anchor any complexes formed in solution, and a labeled antibody specific for the other component of the possible complex to detect anchored complexes.

In another embodiment of the invention, assays may be utilized to identify intracellular proteins that interact with the TREK-1 gene product. Any method suitable for detecting protein-protein interactions may be employed for identifying TREK-1 protein-intracellular protein interactions. Among the traditional methods which may be employed are co-immunoprecipitation, crosslinking and co-purification through gradients or chromatographic columns. Utilizing procedures such as these allows for the isolation of intracellular proteins which interact with TREK-1 gene product. Once isolated, such an intracellular protein can be identified and can, in turn, be used, in conjunction with standard techniques, to identify additional proteins with which it interacts.

Assays may also be utilized to identify compounds that interfere with TREK-1 gene product/intracellular macromolecular interactions. TREK-1 gene product may, in vivo, interact with one or more intracellular macromolecules, such as proteins and nucleic acid molecules. For purposes of this discussion, such intracellular macromolecules are referred to herein as "interacting partners." Compounds that disrupt TREK-1 interactions in this way may be useful in regulating the activity of the TREK-1 gene product.

The basic principle of the assay systems used to identify compounds that interfere with the interaction between the TREK-1 gene product and its intracellular interacting partner or partners involves preparing a reaction mixture containing the TREK-1 gene product, or fragments thereof, and the interacting partner under conditions and for a time sufficient to allow the two to interact and bind, thus forming a complex. In order to test a compound for inhibitory activity, the reaction mixture is prepared in the presence and absence of the test compound. The test compound may be initially included in the reaction mixture, or may be added at a time subsequent to the addition of TREK-1 gene product and its intracellular interacting partner. Control reaction mixtures are incubated without the test compound or with a placebo. The formation of any complexes between the TREK-1 gene product or fragments thereof and the intracellular interacting partner is then detected. The formation of a complex in the control reaction, but not in the reaction mixture containing the test compound, indicates that the compound interferes with the interaction of the TREK-1 gene product and the interacting partner.

The assay for compounds that interfere with the interaction of the TREK-1 gene product and interacting partners can be conducted in a heterogeneous or homogeneous format. Heterogeneous assays involve anchoring either the TREK-1 gene product or the binding partner onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the TREK-1 gene products and the interacting partners, e.g., by competition, can be identified by conducting the reaction in the presence of the test substance; i.e., by adding the test substance to the reaction mixture prior to or simultaneously with the TREK-1 gene protein and intracellular interacting partner. Alternatively, test compounds that disrupt preformed complexes, e.g. compounds with higher binding constants that displace one of the components from the complex, can be tested by adding the test compound to the reaction mixture after complexes have been formed.

In yet another embodiment of the invention, cell-based assays may be used for identification of compounds which modulate TREK-1 activity and which may be used in treating cardiovascular disorders by modulating TREK-1 activity. Specifically, such assays identify compounds which affect TREK-1-dependent processes, such as but not limited to the manifestation of a transformed phenotype, i.e, changes in cell morphology, cell division, differentiation, adhesion, motility, or phosphorylation, dephosphorylation of cellular proteins. Other TREK-1-dependent processes which may be affected include but are not limited to stimulation of $K^+$ channel activity. For example, changes in channel activity may be measured by changes in net current by patch clamp recording or changes in resting membrane potential. Compounds identified via such methods can, for example, be utilized in methods for treating cardiovascular disorders.

In an embodiment, cell-based assays are based on expression of the TREK-1 gene product in a mammalian cell and measuring the TREK-1-dependent process. Any mammalian cell that can express the TREK-1 gene and allow the functioning of the TREK-1 gene product can be used. Cells may be recombinantly engineered to express the TREK-1 gene using methods well known to those of skill in the art. In these assays, cells producing functional TREK-1 gene products are exposed to a test compound for an interval sufficient for the compound to modulate the activity of the TREK-1 gene product. The activity of TREK-1 gene product can be measured directly or indirectly through the detection or measurement of TREK-1-dependent cellular processes. As a control, a cell not producing the TREK-1 gene product may be used for comparisons. Depending on the cellular process, any techniques known in the art may be applied to detect or measure it.

In a specific embodiment, the present invention provides a method of identifying an agent that induces activation of a human TREK-1 comprising: (a) providing a cell expressing the human TREK-1 in a membrane of the cell; (b) measuring current produced by the human TREK-1 at a predetermined membrane potential; (c) contacting the human TREK-1 with the agent; and (d) measuring current produced by the human TREK-1 at the predetermined membrane voltage in the presence of the agent, wherein an increase in current measured in step (d) as compared to step (b) indicates that the agent induces activation of human TREK-1.

In another specific embodiment, the present invention provides a method of identifying an agent that induces activation of human TREK-1 comprising: (a) providing a cell expressing a human TREK-1 in a membrane of the cell; (b) measuring current produced by the human TREK-1 at each of a plurality of predetermined membrane potentials; (c) contacting the human TREK-1 with the agent; and (d) measuring current produced by the human TREK-1 at one of the predetermined membrane voltages of step (b) in the presence of the agent, wherein an increase in current measured at the predetermined membrane potential in step (d) as compared to current measured at the same predetermined membrane potential step (b) indicates that the agent induces activation of human TREK-1.

In different embodiments of the instant methods the cell is a Chinese hamster ovary cell, a COS cell, a cardiomyocyte, including a ventricular cardiomyocyte or an atrial cardiomyocyte, or an HEK cell. In a further embodiment, the cell does not normally express TREK-1, and the cell is treated so as to functionally express a TREK-1 channel.

In one embodiment of the instant methods the predetermined membrane potential is from about +40 mV to +60 mV, and more preferably about +50 mV. In one embodiment of the instant methods the each of the plurality of predetermined membrane potentials is from about −120 mV to +60 mV. In another embodiment the predetermined membrane potential in step d) is about +50 mV.

It has been found that, over-expression of TREK-1 can result in an increase in cell proliferation. In contrast, decreasing the TREK-1 mediated current may slow proliferation. Accordingly, the present invention provides methods for identifying modulators of TREK-1 activity based on cell proliferation assays. For example, TREK-1 expressing cells may be grown in a 96-well plate and exposed to varying concentrations of a test substance for 4-24 h followed by measurement of cell proliferation.

Cells that may be utilized in the proliferation assays of the invention include cells over-expressing TREK-1 wherein said over-expression results in an increase in cell proliferation. Such cells include cells that naturally over-express TREK-1 as well as cells genetically engineered to overexpress TREK-1.

Methods of measuring cell proliferation are well known in the art and most commonly include determining DNA synthesis characteristic of cell replication. There are numerous methods in the art for measuring DNA synthesis, any of which may be used according to the invention. For example, DNA synthesis may be determined using a radioactive label ($[^3H]$thymidine) or labeled nucleotide analogues (BrdU) for detection by immunofluorescence. Alternatively, the rate of proliferation can be measured using any of a number of commercial colorimetric kits, such as the MTT assay. Additionally, the cells may be assayed to determine whether there are changes in levels, or modification, of proteins known to be associated with cell proliferation. Such proteins include, for example, cyclin D1, CDK4 or p107. The efficacy of the test compound can be assessed by generating dose response curves from data obtained using various concentrations of the test compound. A control assay can also be performed to provide a baseline for comparison. Compounds which are found to alter cell proliferation may then be screened in an electrophysiological assay to confirm that the effect is due to modulation of TREK-1.

Compounds which may be screened in accordance with the invention include, but are not limited to, small organic or inorganic compounds, peptides, antibodies and fragments thereof, and other organic compounds e.g., peptidomimetics) that modulate TREK-1 activity. Compounds may include, but are not limited to, peptides such as, for example, soluble peptides, including but not limited to members of random peptide libraries (see, e.g., Lam, K. S. et al., 1991, Nature 354:82-84; Houghten, R. et al., 1991, Nature 354:84-86); and combinatorial chemistry-derived molecular library made of D- and/or L-configuration amino acids, phosphopeptides (including, but not limited to, members of random or partially degenerate, directed phosphopeptide libraries; (see, e.g., Songyang, Z. et al., 1993, Cell 72:767-778), antibodies (including, but not limited to, polyclonal, monoclonal, humanized, anti-idiotypic, chimeric or single chain antibodies, and FAb, F(ab')$_2$ and FAb expression library fragments, and epitope binding fragments thereof), and small organic or inorganic molecules.

This invention also provides a method of treating a condition associated with phosphorylation of a human TASK-1 channel in a subject comprising administering to the subject an amount of a compound effective to dephosphorylate amino acid residue S358 and/or T383 of the human TASK-1 channel so as to thereby restore human TASK-1 channel function and thereby treat the condition. In differing embodiments, the compound is an activator of an endogenous phosphatase or a phosphatase.

The present invention further relates to pharmaceutical compositions comprising a compound effective to dephosphorylate TASK-1 and a pharmaceutically acceptable carrier in an amount effective to overcome phosphorylation dependent loss of TASK-1 function. In a preferred embodiment of the invention amino acid residue S358 and/or T383 of the human TASK-1 channel is dephosphorylated.

This invention also provides a method of treating a condition associated with phosphorylation of a human TASK-1 channel in a subject comprising administering to the subject an amount of a compound effective to inhibit phosphorylation of the human TASK-1 channel so as to thereby restore human TASK-1 channel function and thereby treat the condition. In a specific embodiment of the invention, phosphorylation of amino acid residue S358 and/or T383 is inhibited. In one embodiment, the compound is a kinase inhibitor, and in a further embodiment, the kinase inhibitor is an inhibitor of protein kinase C epsilon (PKCε). In one embodiment, the condition associated with phosphorylation of TASK-1 is a cardiovascular disorder.

The present invention further relates to pharmaceutical compositions comprising a compound effective to inhibit TASK-1 phosphorylation and a pharmaceutically acceptable carrier in an amount effective to overcome phosphorylation dependent loss of TASK-1 function.

This invention further provides the instant methods, wherein the condition associated with phosphorylation of TASK-1 is an atrial fibrillation, and particularly a peri-operative atrial fibrillation. In another embodiment the condition associated with phosphorylation of TASK-1 is a ventricular arrhythmia, and in particular a post-ischemic arrhythmia.

In a different embodiment the condition associated with phosphorylation of TASK-1 is an overactive bladder.

The appropriate concentration of the composition capable of modulating the phosphorylation of TASK-1, which will be effective in the treatment of a particular cardiac disorder or condition, will depend on the nature of the disorder or condition, and can be determined by one of skill in the art using standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses maybe extrapolated from dose response curves derived from in vitro or animal model test systems. Additionally, the administration of the compound could be combined with other known efficacious drugs if the in vitro and in vivo studies indicate a synergistic or additive therapeutic effect when administered in combination.

This invention also provides a method of treating a condition associated with an ionic channel dysfunction resulting in reduced net outward current in a subject comprising myocyte overexpression of TREK-1 activity at a level effective to overcome the reduced net outward current so as to thereby treat the condition.

In one embodiment the TREK-1 gene is genetically engineered into a recombinant DNA construct in which expression of TREK-1 is placed under the control of a strong promoter. For general reviews of the methods of gene therapy, see Goldspiel et al., 1993, Clinical Pharmacy 12:488-505; Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62:191-217; May, 1993, TIBTECH 11(5): 155-215). Methods commonly known in the art of recombinant DNA technology which can be used are described in Ausubel et al. (eds.), 1993, Current Protocols in Molecular Biology, John Wiley & Sons, NY; Kriegler, 1990, Gene Transfer and Expression, A Laboratory Manual, Stockton Press, NY; and in Chapters 12 and 13, Dracopoli et al. (eds.), 1994, Current Protocols in Human Genetics, John Wiley & Sons, NY.

The use of recombinant DNA constructs to transfect target cells, i.e, myocytes, in the patient will result in the transcription of sufficient amounts of the TREK-1 gene transcripts. For example, a vector can be introduced in vivo such that it is taken up by a cell and directs the transcription of the TREK-1 gene.

Such vectors can be constructed by recombinant DNA technology methods standard in the art. Vectors can be plasmid, viral, or others known in the art, used for replication and expression in mammalian cells. Expression of the sequence encoding TREK-1 can be by any promoter known in the art to act in mammalian, preferably human cells. Such promoters can be inducible or constitutive. Such promoters include but are not limited to: the SV40 early promoter region (Bernoist and Chambon, 1981, Nature 290:304-310), the promoter contained in the 3' long terminal repeat of Rous sarcoma virus (Yamamoto et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42), etc. Any type of plasmid, cosmid, YAC or viral vector can be used to prepare the recombinant DNA construct which can be introduced either directly into the tissue site, or via a delivery complex. Alternatively, viral vectors can be used which selectively infect the desired tissue.

In a specific embodiment, a viral vector that contains the TREK-1 gene can be used. For example, a retroviral vector can be used (see Miller et al., 1993, Meth. Enzymol. 217:581-599). Adenoviruses are other viral vectors that can be used in gene therapy. Kozarsky and Wilson, (1993, Current Opinion in Genetics and Development 3:499-503) present a review of adenovirus-based gene therapy. Adeno-associated virus (AAV) has also been proposed for use in gene therapy (Walsh et al., 1993, Proc. Soc. Exp. Biol. Med. 204:289-300.

This invention also provides a method of treating a condition associated with an ionic channel dysfunction resulting in reduced net outward current in a subject comprising administering to the subject an amount of a TREK-1 modulator or a two pore-domain potassium channel modulator effective to overcome the altered net outward current so as to thereby treat the condition. In one embodiment the condition is prostate cancer.

Such ion channel dysfunction results in a lower outward ionic current across mammalian cell plasma membranes resulting, including those of heart cells such as myocytes.

EXAMPLES

This invention will be better understood by reference to the Experimental Details which follow, but those skilled in the art will readily appreciate that the specific experiments detailed are only illustrative of the invention as described more fully in the claims which follow thereafter.

Example 1

Platelet-activating factor (PAF), an inflammatory phospholipid, induces ventricular arrhythmia via an unknown ionic mechanism. In this first series of experiments, PAF-mediated cardiac electrophysiologic effects are linked to inhibition of the two-pore domain K+ channel, TASK-1. Superfusion of carbamyl-platelet-activating factor (C-PAF), a stable analogue of PAF, over murine ventricular myocytes causes abnormal automaticity, plateau phase arrest of the action potential and early after depolarizations in paced and quiescent cells from wild-type but not PAF receptor knockout mice. C-PAF-dependent currents are insensitive to $Cs^+$ and are outwardly rectifying with biophysical properties consistent with a $K^+$-selective channel. The current is blocked by TASK-1 inhibitors, including protons, $Ba^{2+}$, $Zn^{2+}$, and methanandamide, a stable analogue of the endogenous lipid ligand of cannabanoid receptors. In addition, when TASK-1 is expressed in CHO cells that express an endogenous PAFR, superfusion of C-PAF decreases the expressed current. Like C-PAF, methanandamide evoked spontaneous activity in quiescent myocytes. C-PAF— and methanandamide-sensitive currents are blocked by a specific PKC inhibitor, implying overlapping signaling pathways. In conclusion, C-PAF blocks TASK-1 or a closely related channel, the effect is PKC-dependent, and the inhibition alters the electrical activity of myocytes in ways that would be arrhythmogenic in the intact heart.

C-PAF alters the rhythm of paced, wild-type, ventricular myocytes.

Myocytes from WT mice were paced (cycle length 1000 ms) and monitored in current clamp mode to record action potentials. When the action potential duration was stable for 2 min, cells were superfused with C-PAF (185 nM, FIG. 1), a concentration that elicited electrophysiologic effects in 9 of 11 cells. C-PAF-evoked responses occurred after a delay (94±21 s; range 23 to 184 s), and typically included abnormal automaticity (FIG. 1, 110 s) leading to a maintained depolarization (FIG. 1, 111 s). In 8 of 9 cells, alteration of the membrane potential slowly returned to normal, presumably due to receptor desensitization and after 3 min of agonist perfusion was indistinguishable from control (FIG. 1 inset).

C-PAF decreases an outward current that is K+-selective and carried by TASK-1.

Figure 2A:
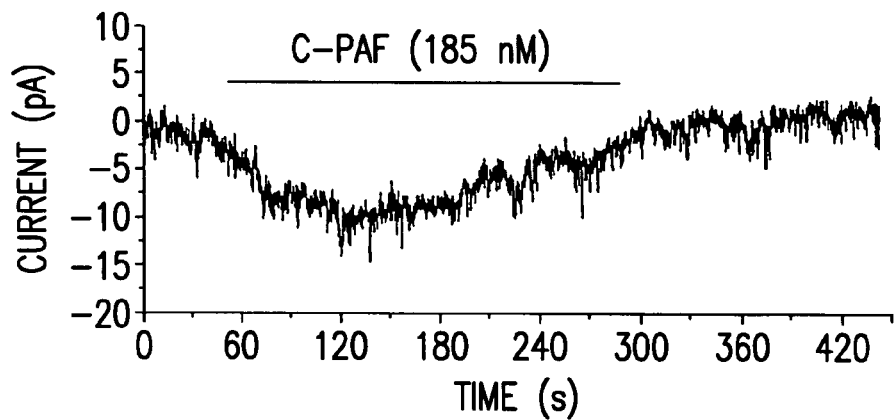
FIGS. 2A-2C. Application of C-PAF causes a depolarizing shift in net membrane current in WT but not in KO myocytes. Superfusion of C-PAF (185 nM) caused a transient decrease in the net outward current in a WT myocyte held at −10 mV (2A). In this trace the baseline outward holding current has been adjusted to zero to illustrate the C-PAF-sensitive current. The spontaneous reversal of the C-PAF effect probably indicates desensitization of the PAFR. The I-V relation of the C-PAF-difference current (control minus C-PAF) is plotted as a net outward current over a range of potentials in WT myocytes (2B, filled squares). In PAFR KO myocytes (filled circles) no C-PAF-sensitive current was detected at all potentials tested. Each data point is the mean±SEM of data from at least 4 cells at each potential. The I-V relation was also measured using a ramp protocol in high extracellular $K^+$ (50 mM) plus $Cs^+$ (5 mM) and $TEA^+$ (1 nM) to permit determination of the reversal potential (2C). Each data point is the mean±±SEM of data from at least 5 cells from 2 animals.
Figure 2B:
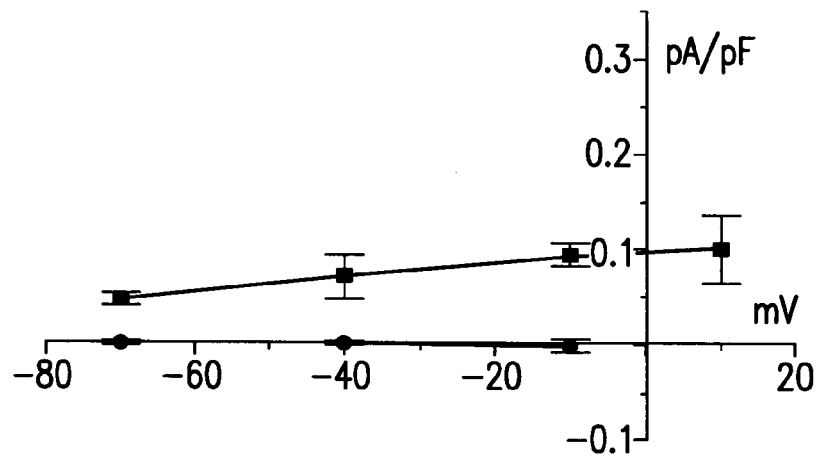

Cells were held at −10 mV and total steady state membrane currents were measured. The mean holding current was 133±12 pA (n=24). WT myocytes responded to C-PAF with decreased net outward current that often began to reverse during the perfusion and recovered completely after wash out (FIG. 2A). Since a depolarizing shift in steady state current can be caused by increased inward currents or decreased outward currents, it was determined how C-PAF affected conductance. When a +10 mV step was applied during control and agonist superfusion, it was found that C-PAF decreased conductance 17.5±3.9% (n=5; p<0.05), indicating that the lipid inhibits outward current(s). The main conductance maintaining resting potential in the ventricle is $IK_1$, therefore whether this inwardly rectifying K+ current was involved in the action of C-PAF was investigated. $Cs^+$ (5 mM), which largely blocks $IK^1$ under these conditions (data not shown), did not reduce the C-PAF-sensitive current in cells held at −70 mV. The average C-PAF-sensitive current density was 0.047±0.01 pA/pF in control cells compared to 0.047±0.03 pA/pF in cells in the presence of $Cs^+$ (n=6). By extending the voltage clamp study to other potentials, a nearly linear I-V relation was obtained for the C-PAF difference current (FIG. 2B, filled squares). In KO myocytes the C-PAF-sensitive current was absent at all potentials tested (FIG. 2B, filled circles).

Figure 2C:
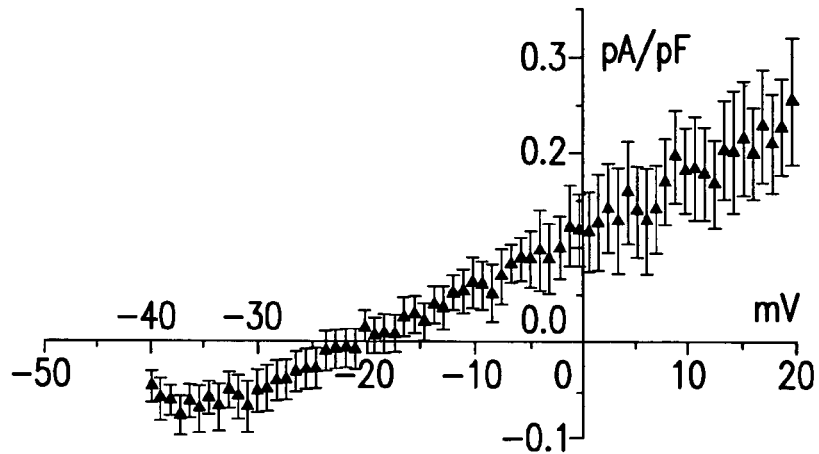

A clear reversal potential in physiologic K+ over the voltage range tested was not observed. Therefore, additional experiments were conducted in elevated extracellular K+ (50 mM with Na+ reduced to 100 mM, plus Cs+5 mM and TEA+ 1 mM) designed to measure the reversal potential of the C-PAF-sensitive current. In elevated extracellular K+, the results show a weakly outward rectifying current with an I-V relation that is consistent with that of a predominantly $K^+$-selective channel (FIG. 2C). The calculated $E_K$ for these recording conditions is −27.6 mV and the observed reversal for the C-PAF-sensitive current occurred at −20.4±3 mV (n=5).

Figure 3:
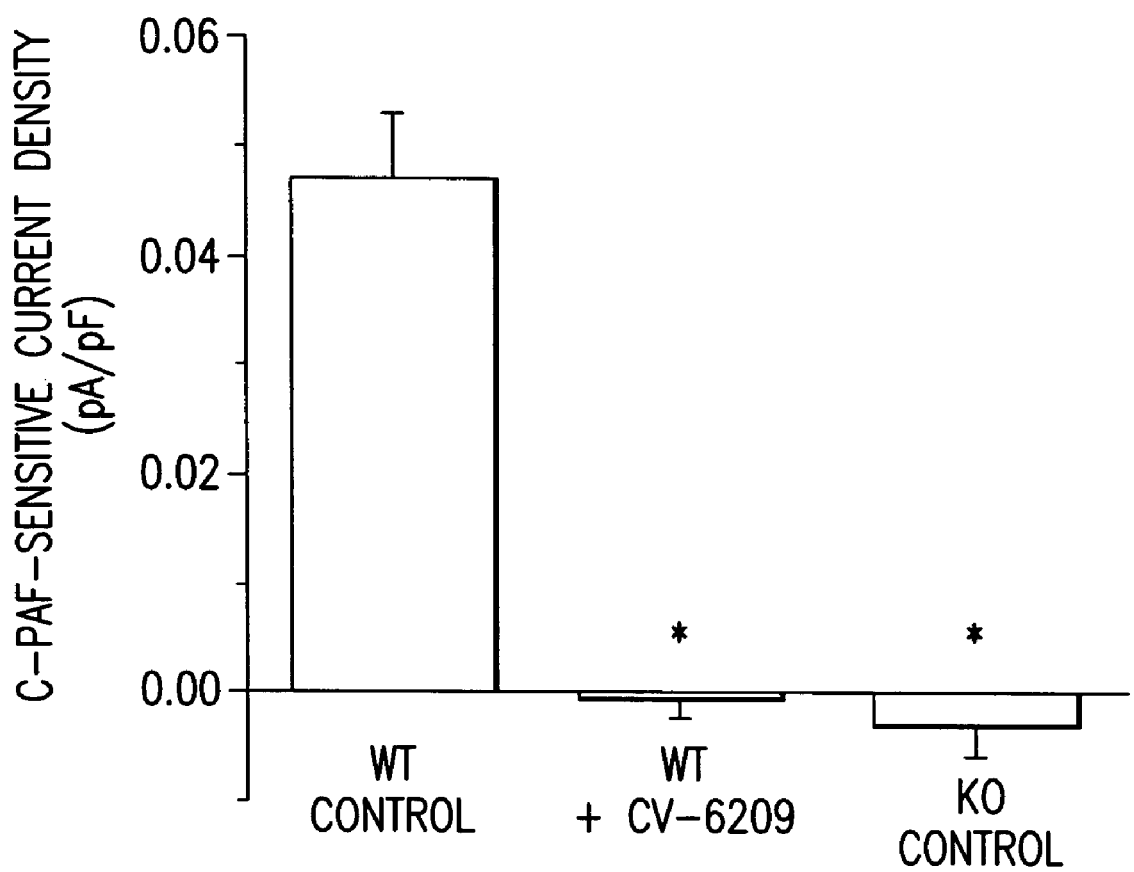
FIG. 3. The C-PAF-sensitive current is receptor-mediated. The C-PAF-sensitive current was measured in WT myocytes held at −70 mV under various conditions. The current under control conditions in wild-type myocytes disappeared in the presence of the PAFR antagonist, CV-6209 (100 nM; n=5). There was no C-PAF-sensitive current detected in myocytes from KO mice (n=3). *, p<0.01.

The C-PAF-sensitive current was blocked by the PAFR antagonist, CV-6209 (100 nM; FIG. 3). The lack of a C-PAF-dependent response in the presence of CV-6209 was identical to the results obtained in myocytes derived from KO mice (FIG. 3). Taken together, these results confirm that the C-PAF effect is mediated by the PAFR and involves inhibition of an outward K+ current distinct from $IK_1$.

These characteristics of the C-PAF-sensitive current suggested that it may be mediated by a member of the "two-pore domain" potassium channel family (Lesage F, and Lazdunski M. (2000) Am J Physiol 279: F793-F801). TASK-1 is a member of this family that is expressed in mammalian heart (Kim D et al. (1998) Circ Res 82: 513.-518; Kim Y et al.(1999) Am J Physiol 277: H1669-H1678, Lesage F, and Lazdunski M. (2000) Am J Physiol 279: F793-F801, 14). In heterologous expression systems, this channel is outwardly rectifying and is blocked by $H^+$, $Ba^{2+}$, $Zn^{2+}$ and anandamide, an endogenous cannabinoid receptor ligand (Kim D et al. (1998) Circ Res 82: 513-518; Kim Y et al.(1999) Am J Physiol 277: H1669-H1678; Lesage F, and Lazdunski M. (2000) Am J Physiol 279: F793-F801; Lopes C M B et al. (2000) J Biol Chem 275: 16969-16978; Maingret F et al.(2001) EMBO J. 20: 47-54; Millar J A et al. (2000) Proc Natl Acad Sci USA 97: 3514-3618; Talley E et al. (2000) Neuron 25: 399-410).

Figure 4:
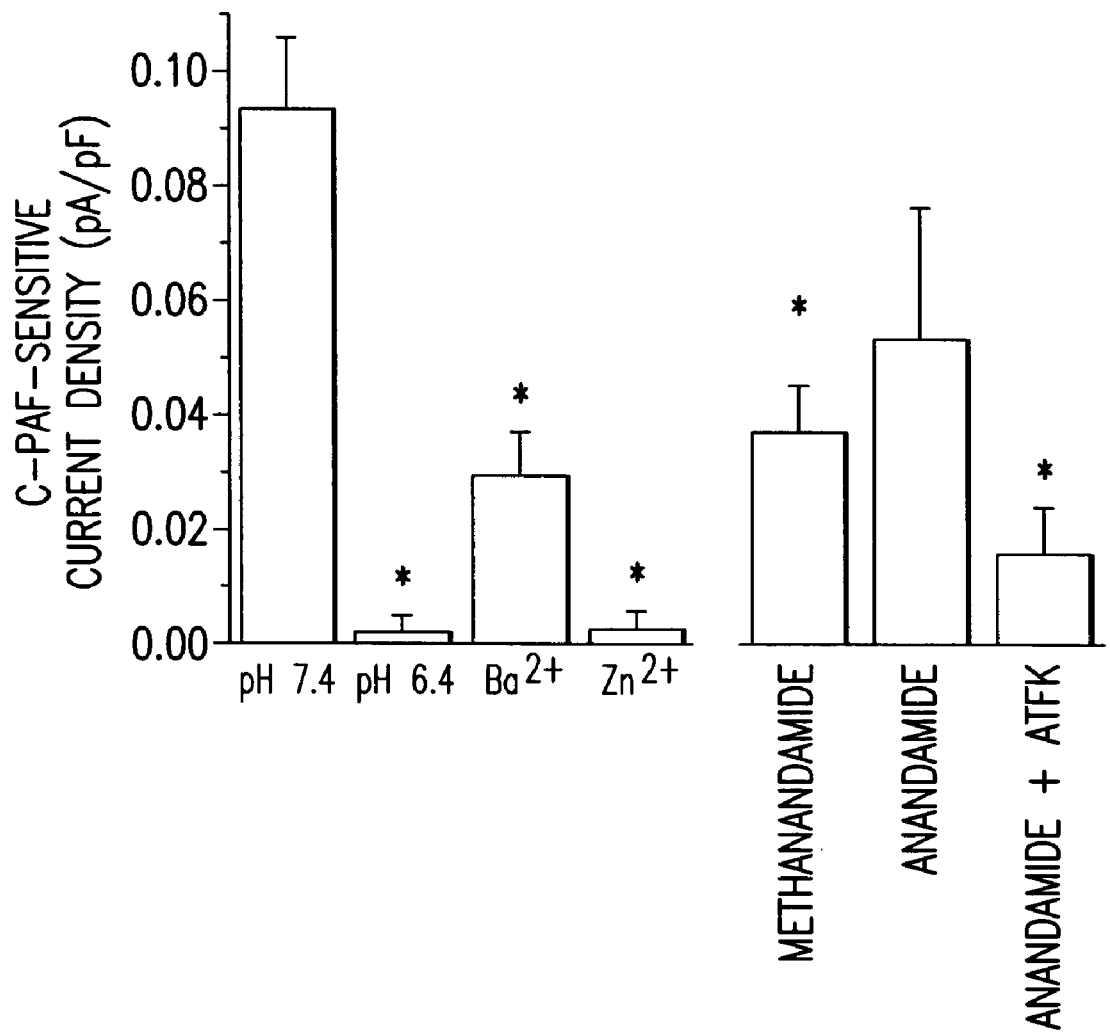
FIG. 4. Block of TASK-1 decreases the C-PAF-sensitive steady-state current. Wild-type myocytes were held at −10 mV and the C-PAF-sensitive current was measured at pH 7.4 (n=25). The change in net current elicited by C-PAF (185 nM) was significantly decreased in the presence of Tyrode's at pH 6.4 (n=6), $Ba^{2+}$ (3 mM; n=6), or $Zn^{2+}$ (3 mM; n=8). The stable anandamide analogue, methanandamide (10 μM; n=12) also significantly reduced the C-PAF-sensitive current as did anandamide in the presence of ATFK, a drug that inhibits anandamide metabolism (10 μM; n=8). Anandamide alone did not significantly inhibit the current (10 μM; n=5) due to its rapid metabolic inactivation. *, p<0.05 compared to control at pH 7.4.

Consistent with this, in isolated myocytes, when the external pH was lowered to 6.4 or when $Ba^{2+}$ (3 mM) or $Zn^{2+}$ (3 mM) were present, the C-PAF-sensitive current was significantly reduced (FIG. 4, left panel). Methanandamide (10 µM), a stable analog of anandamide, also inhibited the C-PAF-sensitive current (FIG. 4, right panel). In contrast, anandamide inhibition was only significant in the presence of ATFK (10 µM), an inhibitor of anandamide hydrolysis (FIG. 4), suggesting rapid metabolism of anandamide by ventricular myocytes. ATFK alone had no effect (not shown).

Figures 5A, 5B:
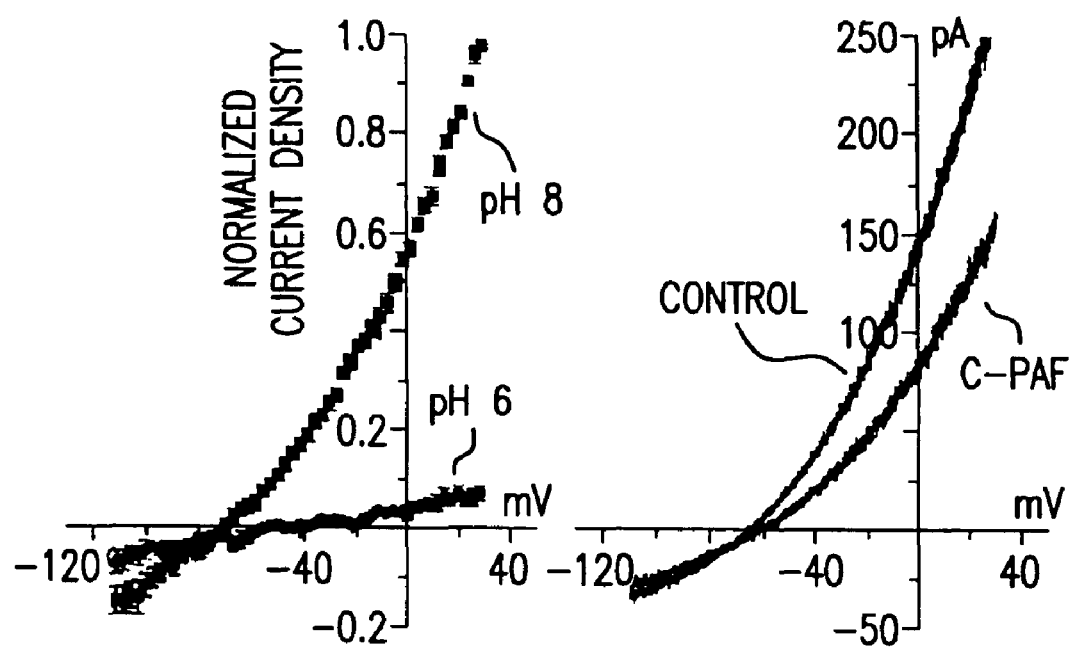
FIGS. 5A-5B. TASK-1, heterologously expressed in CHO cells is sensitive to pH and to C-PAF. Net steady-state current was measured by a ramp clamp under alkaline (pH 8) and acidic (pH 6) conditions demonstrating the pH sensitivity of the expressed TASK-1 current. The I-V relation of each cell was normalized to the current at +30 mV to correct for cell-to-cell variability in expression levels and the mean normalized current density was plotted (5A; n=13) In CHO cells exposed to C-PAF (185 nM) the expressed TASK-1 current was decreased (5B). Representative I-V relations before (Control) and during drug treatment (C-PAF) were compared. This result is representative of 8 cells. On average, the I-V relation returned to within 5% of control value after washout of C-PAF.

CHO cells expressing TASK-1 exhibited a large outwardly rectifying current that was pH sensitive. The mean I-V relation at alkaline and acidic pH is shown in FIG. 5 (left panel) and demonstrates that the reduction of the external pH to 6 completely eliminated the outwardly rectifying current. Mean current density at +30 mV in cells expressing TASK-1 was 26 pA/pF compared to 0.6 pA/pF for non-transfected cells. When TASK-1 transfected CHO cells were superfused with C-PAF (185 nM), the expressed current was reduced (FIG. 5, right panel) demonstrating the inhibitory effect of C-PAF on TASK-1 dependent current.

Figure 6:
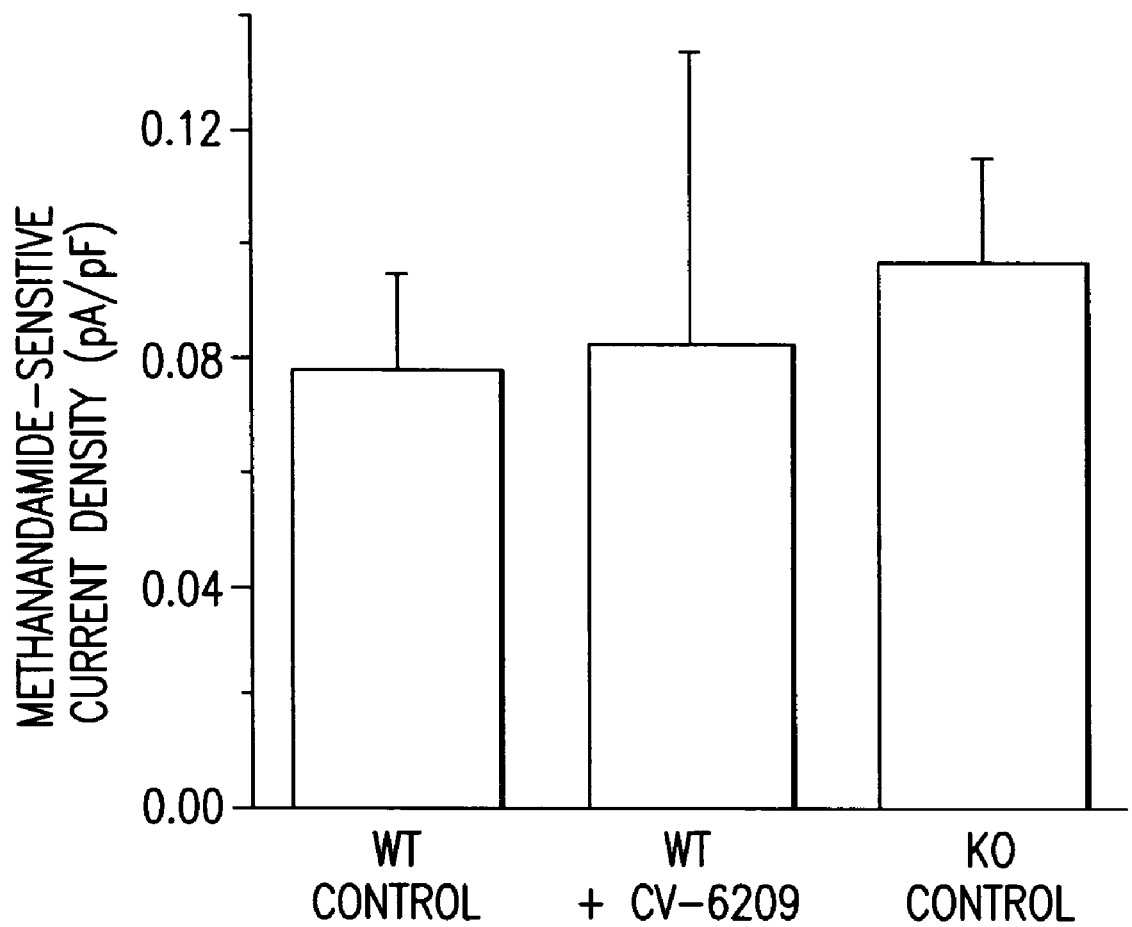
FIG. 6. The methanandamide-sensitive current is independent of the PAFR. WT cells held at −10 mV were superfused with methanandamide (10 μM) and the methanandamide-sensitive current was measured (WT Control; n=6). The methanandamide-sensitive current did not differ from control when WT cells were incubated with the PAFR antagonist, CV-6209 (100 nM; n=3) or in myocytes derived from PAFR knockout mice (KO Control; n=6).

If both C-PAF and methanandamide block TASK-1, then methanandamide itself should cause a decreased net outward current. Thus, the methanandamide-sensitive current was measured (FIG. 6). Since this current is comparable to the C-PAF-sensitive current, it was also investigated whether the methanandamide-sensitive current was mediated by the PAFR. It was found that the lipid was fully effective in the presence of the PAFR antagonist, CV-6209 or when applied to myocytes from KO mice (FIG. 6). Thus, the effect of methanandamide is not mediated by the PAFR.

C-PAF Action Involves PKC-Dependent Block of TASK-1.

Figure 7A:
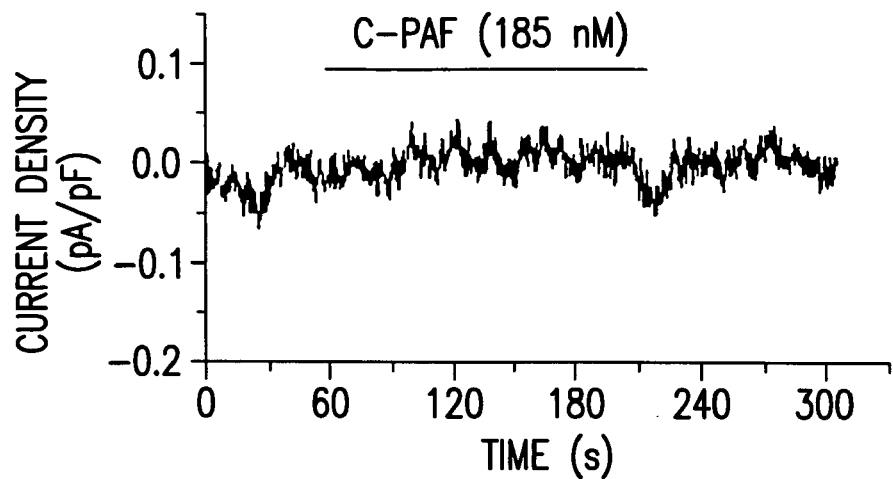
FIGS. 7A-7C. The C-PAF-sensitive current is blocked by inhibition of PKC. The C-PAF-sensitive current is completely blocked in myocytes (held at −10 mV), exposed to BIM I, a specific PKC inhibitor (100 nM; 7A). In this trace, the baseline holding current has been adjusted to zero to illustrate the absence of a C-PAF-sensitive current. BIM I-mediated inhibition of the C-PAF-sensitive current is dose dependent (7B, 40 nM, n=7; 100 nM, n=11). An inactive BIM I analogue, BIM V does not block the C-PAF-sensitive current (7B, right; n=10). The inhibition of the C-PAF-sensitive current by BIM I is independent of voltage (7C; 100 nM BIM; n is at least a 4 for each data point). *, p<0.05; **, p<0.001 versus control.
Figure 7B:
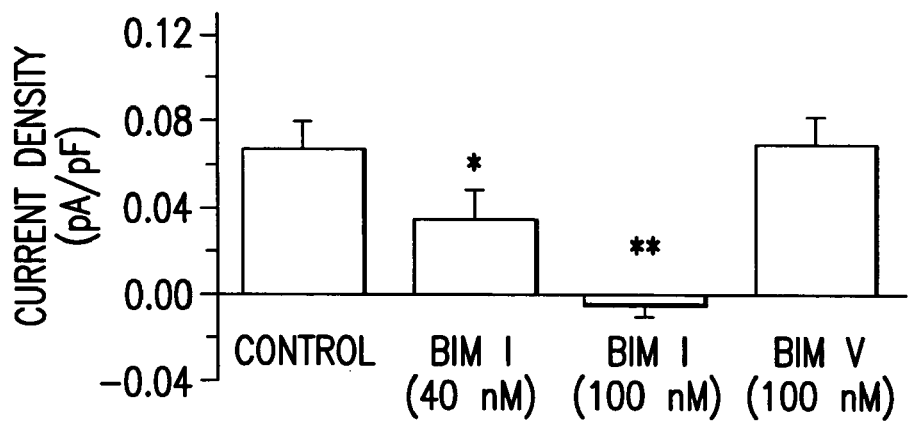
Figure 7C:
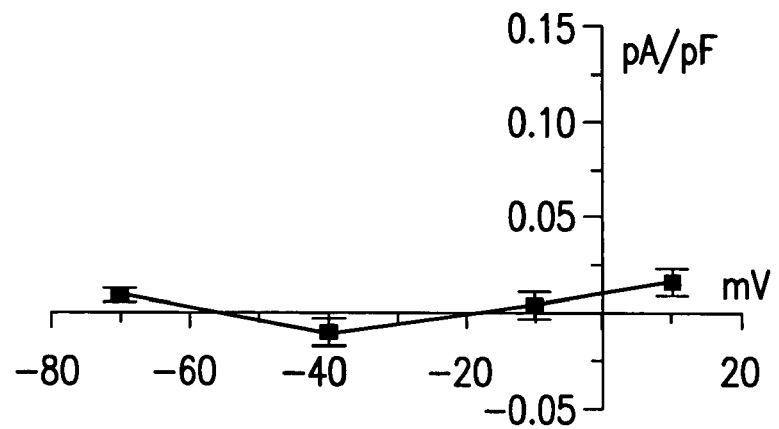

In many cell-types, PAF initiates an intracellular pathway that results in activation of protein kinase C (PKC) (Chao W and Olson M S (1993) Biochem J 292: 617-629, Massey C V et al.(1991) J Clin Invest 88: 2106-2116; Montrucchio G et al. (2000) Physiol Rev 80: 1669-1699; Shukia S D. (1992) FASEB J 6: 2296-2301). To determine if C-PAF initiates this cascade in ventricular myocytes, cells were incubated with bisindolylmaleimide I (BIM I), a selective PKC inhibitor (25) ($K_i$, 14 nM) before applying C-PAF. The C-PAF-sensitive current was blocked in a dose-dependent manner (FIGS. 7A and B) by BIM I but was not altered by the addition of an inactive analogue, BIM V. The inhibition occurred in a voltage-independent manner (FIG. 7C).

It was next queried whether the methanandamide-sensitive current also required PKC activity. BIM I (100 nM) significantly reduced the methanandamide-sensitive current in WT myocytes ($p<0.05$; n=5; data not shown).

C-PAF and Methanandamide Induce Spontaneous Activity in Quiescent Myocytes.

Figure 8A:
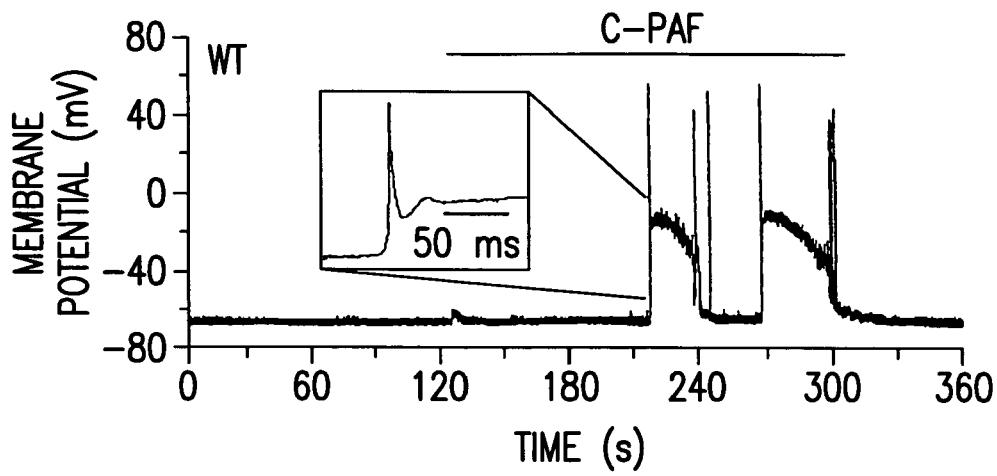
FIGS. 8A-8C. C-PAF and methanadamide elicit spontaneous activity in quiescent myocytes. Quiescent myocytes from WT and KO mice were studied in current clamp mode. C-PAF (185 nM) application elicited spontaneous activity in WT (8A) but not KO myocytes (8B). Superfusion of methanandamide (10 μM) over WT myocytes caused the same effect as C-PAF (8C). There was no measurable change in the resting potential prior to impulse initiation. These recordings are typical of 11 cells for 8A, 7 cells for 8B and 7 cells for 8C.
Figure 8B:
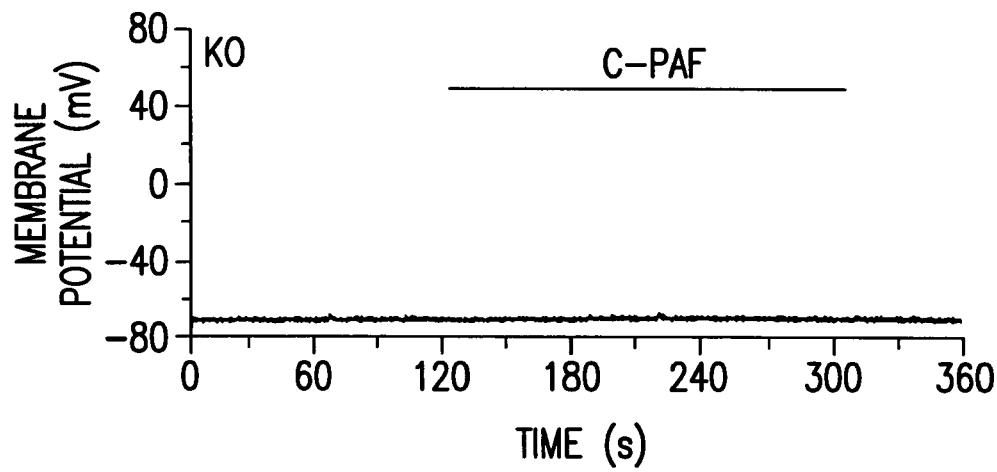

Because C-PAF and methanandamide affect net steady-state current at voltages near the resting potential, whether electrophysiologic effects occurred independent of pacing was determined. Membrane potential was recorded from myocytes that remained quiescent for at least 2 min. Every WT quiescent myocyte tested was sensitive to C-PAF superfusion (11 of 11 cells; FIG. 8A), typically responding with an action potential that arrested in the plateau phase (FIG. 8A, inset) and exhibited many small fluctuations of the membrane potential and EAD. Eventually, the membrane repolarized. The duration of the effect was variable, but its appearance always followed an initial delay (96±11 s). In contrast, when C-PAF was applied to ventricular myocytes isolated from PAFR KO mice, there was no response in most of the cells (7 of 9; FIG. 8B). The responsiveness of WT and KO myocytes to C-PAF differed significantly ($p<0.01$; $\chi^2=9.96$) although their resting potentials did not (−70.6±1.1 mV versus −71.3±1.5 mV). Finally, 6 of 8 quiescent wild-type cells failed to respond to C-PAF (185 nM) following BIM I treatment (100 nM). A comparison of BIM-treated to control myocytes indicated a significant reduction in susceptibility to spontaneous activity ($p<0.01$; $\chi^2=8.84$).

Figure 8C:
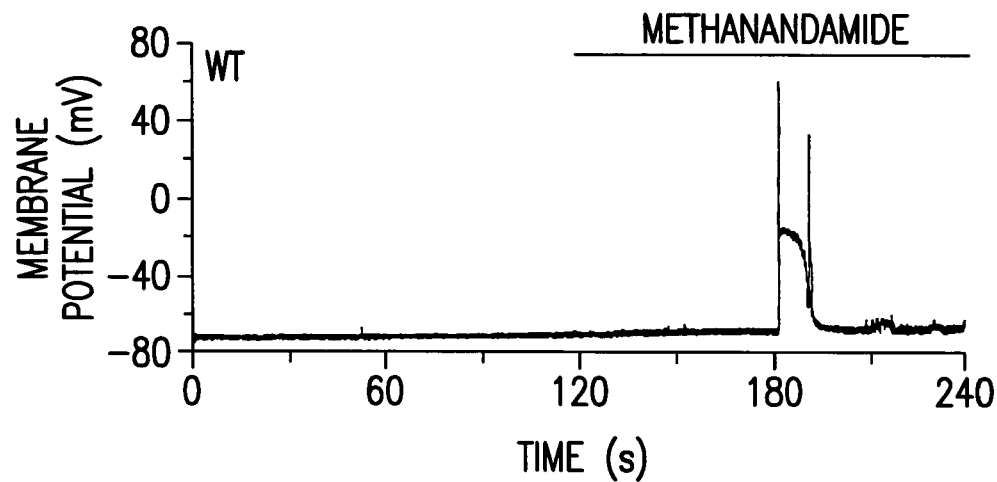

If the decrease in outward current caused by blocking the TASK-1 channel is related to the arrhythmogenic effects of C-PAF, application of a TASK-1 inhibitor in current clamp mode should mimic the effects of C-PAF and evoke spontaneous activity. Accordingly, when methanandamide was applied to quiescent wild-type myocytes, spontaneous action potentials were observed (FIG. 8C; 7 of 12 cells). Statistical analysis showed no difference in occurrence of spontaneous activity during methanandamide as compared to C-PAF superfusion.

Discussion

Inflammatory products released by PMNL can have negative effects on cardiac function and the survival of areas at risk following periods of ischemia and reperfusion (Lucchesi B R, and Mullane K M. (1986) Annu Rev Pharmacol Toxicol 26: 201-224).

Earlier studies, in isolated canine ventricular myocytes (Hoffman B F et al.(1997) J Cardiovasc Electrophysiol 8:679-687), demonstrated that PAF, a PMNL-derived inflammatory lipid, could alter action potentials by prolongation of the APD, EADs and arrest at the plateau. The current study demonstrates that in murine ventricular myocytes C-PAF also triggers a series of alterations in the action potentials, including spontaneous beats, EADs and prolonged depolarization similar to those observed in canine myocytes (Hoffman B F et al.(1997) J Cardiovasc Electrophysiol 8:679-687; Hoffman, B F et al.(1996) J Cardiovasc Electrophysiol 7:120-133). This supports the validity of the mouse as a model in which to study the molecular basis of the arrhythmogenic effect of PAF.

Changes in the membrane potential, spontaneous activity and in specific ion currents in myocytes as they are exposed to C-PAF were measured. This lipid causes a small change in net current that develops over the first minute after application. Changes in the action potential (or appearance of spontaneous action potentials in quiescent cells) lag behind the peak current by approximately 20 s (at −70 mV the C-PAF-sensitive current peaked by 74±13 s). The generation of spontaneous activity in quiescent myocytes implies that changes in membrane potential are not strictly dependent upon the stimulus or alterations in active currents but, rather, it is likely that the agonist perturbs the balance among those currents active at the resting membrane potential. Voltage clamp experiments measuring changes in conductance indicate that C-PAP effects are dependent on a decrease in outward current(s). In addition, the C-PAF-sensitive current, measured in elevated $K^+$ showed weak outward rectification and had a reversal potential close to the calculated $E_K$. These data indicate that the C-PAF-sensitive current is largely carried by $K^+$.

Since experiments utilizing $Cs^+$ argue against the involvement of $IK_1$ in the ionic mechanism underlying the PAF-sensitive current, our attention shifted to other $K^+$ channels that are active at rest. The two-pore domain $K^+$ channels (Lesage F, and Lazdunski M. (2000) Am J Physiol 279: F793-F801) are voltage and time-independent background channels having characteristics similar to the channel responsible for the C-PAF-sensitive current. Among this family, TASK-1 (TWIK related Acid-Sensitive $K^+$ background channel; also referred to as cTBAK-1 (Kim D et al. (1998) Circ Res 82: 513.-518) and Kcnk3 (Lopes C M B et al. (2000) J Biol Chem 275: 16969-16978) is expressed in the heart (Kim Y et al. (1999) Am J Physiol 277: H1669-H1678). TASK-1 is sensitive to small variations in external pH and is almost completely inhibited at pH 6.4. It is also blocked by $Ba^{2+}$ or $Zn^{2+}$ and by the putative endogenous lipid ligand of the cannabinoid receptors, anandamide (Maingret F et al.(2001) EMBO J. 20: 47-54). The C-PAF-sensitive current in murine ventricular myocytes was sensitive to all these interventions suggesting that C-PAF-mediated effects are associated with inhibition of TASK-1 or a closely related channel. Confirmation that the TASK-1 channel is, sensitive to C-PAF was obtained by expressing TASK-1 in CHO cells. When TASK-1 expressing CHO cells were superfused with C-PAF, the expressed current was reduced.

Since the data suggested that the C-PAF-sensitive current is due to TASK-1 blockade, it was reasoned that anandamide treatment might prevent myocytes from responding to C-PAF. In fact, both anandamide in the presence of ATFK, an inhibitor of anandamide hydrolysis, and its nonhydrolyzable analogue, methanandamide, significantly reduced the C-PAF effect confirming our hypothesis. It follows that if C-PAF and methanandamide both inhibit TASK-1 and if this is the ionic basis for the C-PAF-sensitive effects, methanandamide should induce similar changes in myocyte physiology. As predicted, methanandamide caused both a decrease in net outward current and an increase in spontaneous activity in quiescent myocytes. Therefore, it was concluded that both C-PAF and methanandamide exert their biological effects at least in part by inhibiting TASK-1 or a closely related channel.

In a heterologous expression system, Maingret et al. (Maingret F et al.(2001) EMBO J. 20: 47-54) found that anandamide inhibition of TASK-1 was not mediated by the known cannabinoid receptors and since the drug was effective on excised macropatches, they concluded that the lipid interacted directly with the channel. PAF, in contrast, is known to activate cells through a G-protein-linked receptor that initiates a signaling cascade involving activation of phospholipase C generating inositol phosphates and elevating intracellular calcium and diacylglycerol, ultimately activating PKC (Chao W and Olson M S (1993) Biochem J 292: 617-629; Ishii S, and Shimizu T. (2000) Prog Lipid Res 39: 41-82; Massey C V et al.(1991) J Clin Invest 88: 2106-2116; Montrucchio G et al. (2000) Physiol Rev 80: 1669-1699). In these studies, the effect of C-PAF is clearly mediated by the PAFR since its activity can be blocked by the antagonist, CV-6209 and is absent in myocytes derived from mice in which the PAFR has been genetically deleted. In addition, it was found here that inhibition of PKC blocked the C-PAF-sensitive current. Although several reports suggest that TASK-1 is insensitive to PKC activators (Duprat F et al.(1997) EMBO J. 16:5464-5471, Leonoudakis D et al. (1998) J Neurosci 18: 868-877), Lopes, et al. (2000, J Biol Chem 275: 16969-16978) found that PMA causes a slowly developing block of TASK-1 current in an oocyte expression system. This further supports the hypothesis presented here that C-PAF activity is mediated by activation of a PKC-dependent phosphorylation and although it does not resolve the mechanism behind the somewhat unexpected time course of the effect it is entirely consistent with the findings here.

Interestingly, PKC inhibition also reduced the methanandamide-sensitive current suggesting that the two lipids share overlapping intracellular signalling pathways. Therefore, it was tested whether methanandamide required the PAFR for its activity and it was found that it was fully functional in the presence of CV-6209 and in myocytes derived from PAFR KO mice. These data suggest that the methanandamide effect is dependent, at least in part, upon PKC activation. Alternatively the block of the TASK-1 channel by methanandamide may require a basal phosphorylation of the channel itself or an accessory protein and thus, ultimately depends upon but is not mediated by PKC. Such a scenario was recently described for a similar effect of anandamide on the VR1, vanilloid receptor, a non-selective cation channel. In this case, activation of the receptor by anandamide was significantly enhanced when the channel had been phosphorylated by PKC, and anandamide itself stimulated PKC (Premkumar L and Ahem G P (2000) Nature 408: 985-990).

These results suggest a role for the TASK-1 channel in PAF-mediated arrhythmias. However, additional questions remain. While block of TASK-1 channels could contribute to a longer APD and subsequent EADs, this does not preclude additional effects on other currents active during the action potential plateau, including $Ca^{2+}$, Na and the delayed rectifier currents. In addition, the mechanism by which TASK-1 blockade might lead to initiation of spontaneous activity in a quiescent myocyte is not clear, since no measurable change in membrane potential was observed immediately preceding initiation of activity induced by either C-PAF or methanandamide. Additional mechanisms, either secondary to the block of TASK-1 or independent of this action, may occur after exposure to PAF.

Materials and Methods
Cell Preparation

Adult mice, 2-3 months old, were anesthetized with ketamine/xylazine and their hearts were removed according to protocols approved by the Columbia University-IACUC. Experiments were performed on single rod-shaped, quiescent ventricular myocytes dissociated using a standard retrograde collagenase perfusion (Kuznetsov V et al. (1995) Circ Res 76: 40-52) from hearts of mice that were either wild-type (WT), or PAFR knockouts (KO). Both WT and KO mice were bred on a C57/B16 background. The derivation of the KO mice has been described previously (Hoffman, B F et al.(1996) J Cardiovasc Electrophysiol 7:120-133).

Heterologous Expression

The TASK-1 clone (provided by Professor Y. Kurachi, Osaka University) was co-transfected in CHO cells with CD8 plasmid using Lipofectamine Plus (Invitrogen) according to the manufacturer's instructions. 48 h later cells were transferred to the electrophysiology chamber and anti-CD8 coated beads (Dynal Biotech) were added to identify CD8 expressing cells. Expressing cells were voltage clamped using a ramp clamp (see below). CHO cells were used in these experiments, in part, because they express endogenous PAFR.

Buffers and Drugs

Prior to electrophysiological measurements, cells were placed into the perfusion chamber and superfused at room temperature with Tyrode's buffer (in mM: NaCl, 140; KCl, 5.4; $CaCl_2$ 1; $MgCl_2$, Hepes, 5; Glucose, 10; pH 7.4). The whole-cell patch clamp technique was used with pipettes having resistances of 1.5-3 MΩ (intracellular solution, in mM: aspartic acid, 130; KOH, 146; NaCl, 10; $CaCl_2$, 2; EGTA, 5; Hepes, 10; MgATP, 2; pH 7.2). Solutions of C-PAF, the PAFR antagonist, CV-6209 (Biomol) and the PKC inhibitor, bisindolylmaleimide I (BIM I; Calbiochem) were prepared in water and diluted in Tyrode's before use. The inactive analog of BIM I (BIM V; Calbiochem), anandamide, its nonhydrolyzable analogue, methanandamide, and an inhibitor of anandamide hydrolysis, arachidonyltrifluoromethyl ketone (ATFK) (Biomol), were dissolved in DMSO then diluted in Tyrode's. The final DMSO concentration did not exceed 0.1%. A custom-made fast perfusion device was used to exchange the solution around the cell within 1 s (DiFrancesco et al. (1986) J Physiol 377: 61-88).

Electrophysiological Recordings

Current and voltage protocols were generated using Clampex 7.0 software applied by means of an Axopatch 200B amplifier and a Digidata 1200 interface (Axon Instruments). During voltage clamp, steady state current traces were acquired at 500 Hz and final filtered at 10 Hz. During current clamp, membrane voltage was acquired at 5 KHz and filtered at 1 KHz. Ramp clamps were conducted by imposing a voltage ramp (14 mV/s) at a 500 Hz acquisition rate with 1 kHz filtering. Data were analyzed using pCLAMP 8.0 (Axon) and Origin 6.0 (Microcal) and are presented as mean±SEM. Steady-state current was determined by computer calculation of average current over a time period of at least 5 s. In all experiments, the n value indicates the number of myocytes studied, and represents pooled data from at least 2 (voltage clamp) or 3 (current clamp) animals. Student's t-test, one-way ANOVA and $\chi^2$ tests were used; a value of p<0.05 was considered statistically significant. Records have been corrected for the junction potential, which was measured to be 9.8 mV.

Example 2

The second series of experiments focus on one channel that is proposed herein to contribute to cardiac arrhythmias, TASK-1, a member of the recently described family of two pore-domain potassium channels (Bayliss, D. A., Sirois, J. E., and Talley, E. M. (2003) Mol. Interv. 3, 205-219).

The two pore-domain K channel family is composed of at least 15 different members. These channels are widely distributed in excitable tissues—primarily in the brain and heart and in general are responsive to environmental cues such as temperature, pH and stretch (Lesage, F. and Lazdunski, M. (2000) Am. J. Physiol. 279, F793-F801; Kim, D. (2003) Trends Pharmacol. Sci. 24, 648-654). Several are also regulated by lipids such as arachidonic acid or platelet-activating factor (PAF) (Maingret, F. et al., (2000) J. Biol. Chem. 275, 10128-10133; Fink, M. et al. (1998) EMBO J. 17, 3297-3308; Patel, A. J. et al., (1998) EMBO J. 17, 4283-4290). PAF is an inflammatory phospholipid that has been linked to arrhythmogenis in isolated canine ventricular myocytes (Hoffman et al., (1996) J. Cardiovasc. Electrophysiol. 7, 120-133). In the first series of experiments it was shown that PAF regulates the TASK-1 channel and determined that the arrhythmogenic effect of the stable PAF analog, carbamyl-platelet-activating factor (C-PAF) in mouse cardiomyocytes is due to the inhibition of TASK-1 current in a protein kinase C (PKC)-dependent manner (Barbuti, A. et al., (2002) Am. J. Physiol. 282, H2024-H2030).

Activation of the platelet-activating factor receptor (PAFR) leads to a decrease in outward current in murine ventricular myocytes by inhibiting the TASK-1 channel. TASK-1 carries a background or "leak" current and is a member of the two pore-domain potassium channel family. Its inhibition is sufficient to delay repolarization, causing prolongation of the action potential duration and in some cases, early after depolarizations. Here the cellular mechanisms that control regulation of TASK-1 by PAF were determined. Inhibition of TASK-1 via activation of the PAFR is PKC-dependent. Using isoform-specific PKC inhibitor or activator peptides in patch-clamp experiments, it is demonstrated that activation of PKCε is both necessary and sufficient to regulate murine TASK-1 current in a heterologous expression system and to induce repolarization abnormalities in isolated myocytes. Furthermore, site-directed mutagenesis studies have identified threonine-381, in the C-terminal tail of murine TASK-1, as a critical residue in this regulation.

C-PAF Inhibition of TASK-1 Current in CHO Cells Requires Activation of PKC

Figure 9A:
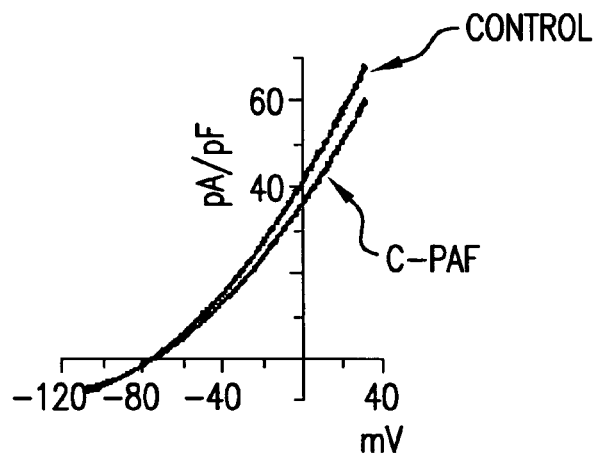
FIGS. 9A-9D. C-PAF inhibition of murine TASK-1 current in CHO cells requires activation of PKC. 9A. The current-voltage relation is plotted for a typical cell in this series under control conditions and after superfusion with C-PAF (185 nM). The average C-PAF-sensitive current (difference current) from 9 cells is plotted in 9B and compared to the C-PAF-sensitive current in the presence of a PKC inhibitor, BIM-I (100 nM) (n=12, p<0.01), 9C. A typical current-voltage recording under control conditions is compared to the recording in the presence of PMA (100 nM). The average PMA-sensitive current is shown in 9D (n=11) together with the α-PMA (an inactive PMA analogue; 100 nM)-sensitive current (n=7). All recordings were made in whole cell configuration using a ramp protocol (−110 to +30 mV over 6 s) in normal Tyrode's solution at pH 8 and corrected for the junction potential. Drugs were applied when the current was stable for at least 1 min and perfused for 2 min for C-PAF or 6 min for PMA. The drug-sensitive current was measured as the difference between the mean current at steady state (averaged from 4 successive ramps) in control and in the presence of the drug. The drug-sensitive currents were normalized by cell capacitance and expressed as current density (pA/pF).
Figure 9B:
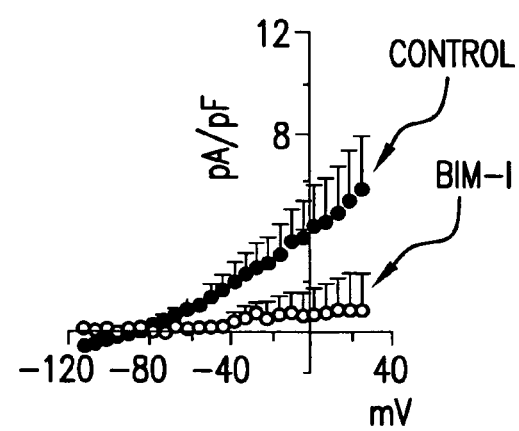

Untransfected CHO cells have no significant endogenous $K^+$ currents (data not shown), thus, all of the current measured in transfected cells was carried by TASK-1. Therefore, TASK-1 was expressed in CHO cells to test the effect of C-PAF (185 nM) on the current in whole-cell patch clamp experiments. During a slow ramp protocol (−110 mV to +30 mV in 6 s), C-PAF rapidly induced a reversible decrease in TASK-1 current that reached steady state within 2 min. When quantified at the maximal current (at +30 mV), this set of cells expressed 68.6±16.4 pA/pF in control solution vs 60.2±14.3 pA/pF in the presence of C-PAF, a 12% decrease in the mean current density (FIG. 9A; n=9, p=0.01). Next it was tested whether the effect of C-PAF on TASK-1 current was due to PKC activation by perfusing the cells with BIM-I (100 nM), a non-isoform specific PKC inhibitor for 2 min before applying C-PAF. In the presence of BIM-I, there was no measurable C-PAF-sensitive current (FIG. 9B, n=12).

Figure 9C:
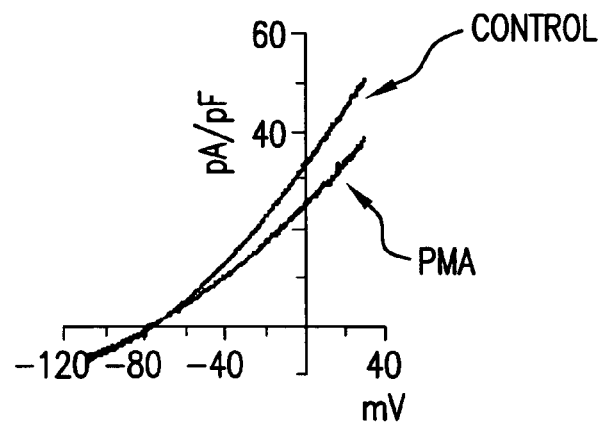
Figure 9D:
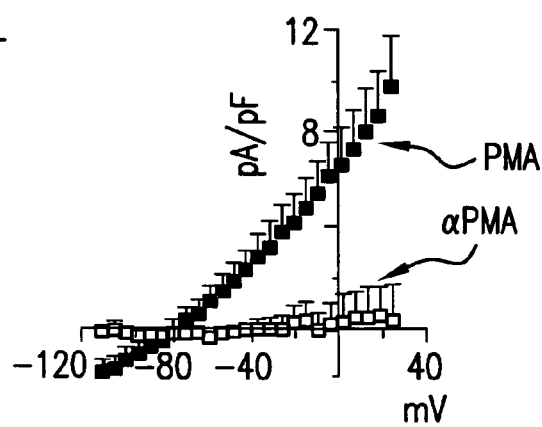

In order to determine whether activation of PKC alone was sufficient to reduce TASK-1 current, CHO cells expressing TASK-1 were treated with a nonspecific activator of PKC, phorbol 12-myristate 13-acetate (PMA, 100 nM). PMA significantly inhibited TASK-1 current in a manner that was similar to the effect of C-PAF (FIG. 9C; n=11, p<0.01). The specificity of the PMA effect was verified by exposing cells to an inactive PMA analogue, 4α-phorbol 12-myristate 13-acetate (αPMA; 100 nM). αPMA had no detectable effect on TASK-1 current, expressed in CHO cells (FIG. 9D). In all TASK-1-expressing cells tested, the mean control current was 71.8±12.3 pA/pF, while in the presence of PMA the current fell to 59.2±10.1 pA/pF. The PMA inhibition (19.8±2.7%, n=17) was significantly greater than that of C-PAF (12.1±1.0%, n=20; p<0.01) when measured at the maximum test voltage of +30 mV, and was irreversible.

The activation of PKCε Decreases TASK-1 Current in CHO Cells

Having shown that the activation of PKC by either C-PAF or PMA was sufficient to cause a decrease of the TASK-1 current, it was subsequently investigated whether one specific isoform of PKC was responsible for this effect. Initially the role of the classical PKC isoforms was discounted since preliminary studies had suggested that the C-PAF effect on TASK-1 was not calcium dependent. Given the prominent role of PKCε in cardiac physiology, the ability of a PKCε-specific inhibitor peptide to block the drug-induced reduction in TASK-1 current was tested. A scrambled peptide was used as a control (Johnson, J et al., (1996) J. Biol. Chem. 271, 24962-24966).

The peptides were introduced to the cells by dialysis through the patch pipette at a final concentration of 100 nM and recordings were initiated 8-10 min after the rupture of the membrane to allow the peptide to equilibrate in the cell. C-PAF failed to inhibit TASK-1 current in the presence of the PKCε-inhibitor peptide (25.6±12.2 pA/pF before C-PAF vs 25.4±12.4 pA/pF after C-PAF, n=8, not significant; FIG. 10A). On the contrary, in the presence of the scrambled peptide, C-PAF-induced inhibition of TASK-1 (8.4±1.5%, n=10) did not differ from control trials in the absence of any peptide. Similarly, the addition of the PKCε-inhibitor peptide to the pipette completely blocked the PMA-sensitive current in CHO cells expressing TASK-1 (FIG. 10B; 42.4±12.7 pA/pF before PMA vs. 41.2±12.3 pA/pF after PMA, n=10, not significant) while the PMA effect was still present with the scrambled peptide (45.1±7.0 pA/pF before PMA vs 36.6±6.2 pA/pF after PMA, n=11, p 0.01). Summary data for C-PAF and PMA are shown in FIG. 10C.

C-PAF Inhibition of TASK-1 Current in Ventricular Myocytes

Is the C-PAF-sensitive current in murine ventricular myocytes, previously defined as a TASK-1 current (Barbuti, A. et al., (2002) Am. J. Physiol. 282, H2024-H2030) also mediated by activation of PKCε. Recordings were done either with the PKCε-inhibitor peptide or the scrambled peptide in the patch pipette while cells were held at −10 mV. Ten to twelve min after the rupture of the membrane and when the holding current was stable for at least 1 min, C-PAF (185 nM) was superfused over the myocytes. In the presence of the scrambled peptide, C-PAF caused a decrease in outward current which was indistinguishable from the effect of C-PAF in the absence of peptide (a typical trace is shown in FIG. 11A). The effect of C-PAF was absent, however, when the PKCε-inhibitor peptide was included in the patch pipette (a typical trace is shown FIG. 11B). Results from numerous trials showed that the inhibitor peptide significantly inhibited the ability of C-PAF to reduce TASK-1 current, in isolated mouse ventricular myocytes while the scrambled peptide had no effect (FIG. 11C).

To further verify that the C-PAF-sensitive current identified in voltage clamp studies was carried by the TASK-1 channel, the I-V relation in myocytes was studied with a slow ramp protocol (−50 mV to +30 mV over 6 s) in the presence of modified Tyrode's. These conditions minimize the contamination of the TASK-1 current by other K$^+$ currents and should allow the calculation of the C-PAF-sensitive current over a wide voltage range by minimizing the outward rectification. To confirm this, the expressed TASK-1 current in CHO cells in modified Tyrode's was firstly examined. As expected, the I-V relation was markedly less rectifying (data not shown) and the reversal potential was less negative (−24.4±1.5 mV, compared to a calculated value of −27.5 mV in modified Tyrode's for a K$^+$ selective current). The C-PAF inhibition in the presence of elevated K$^+$ (10.2±1.8% inhibition, n=16) was indistinguishable from the previously, reported effect of the lipid on TASK-1 in CHO cells recorded in normal Tyrode's (p=0.33).

Figures 12A, 12B:
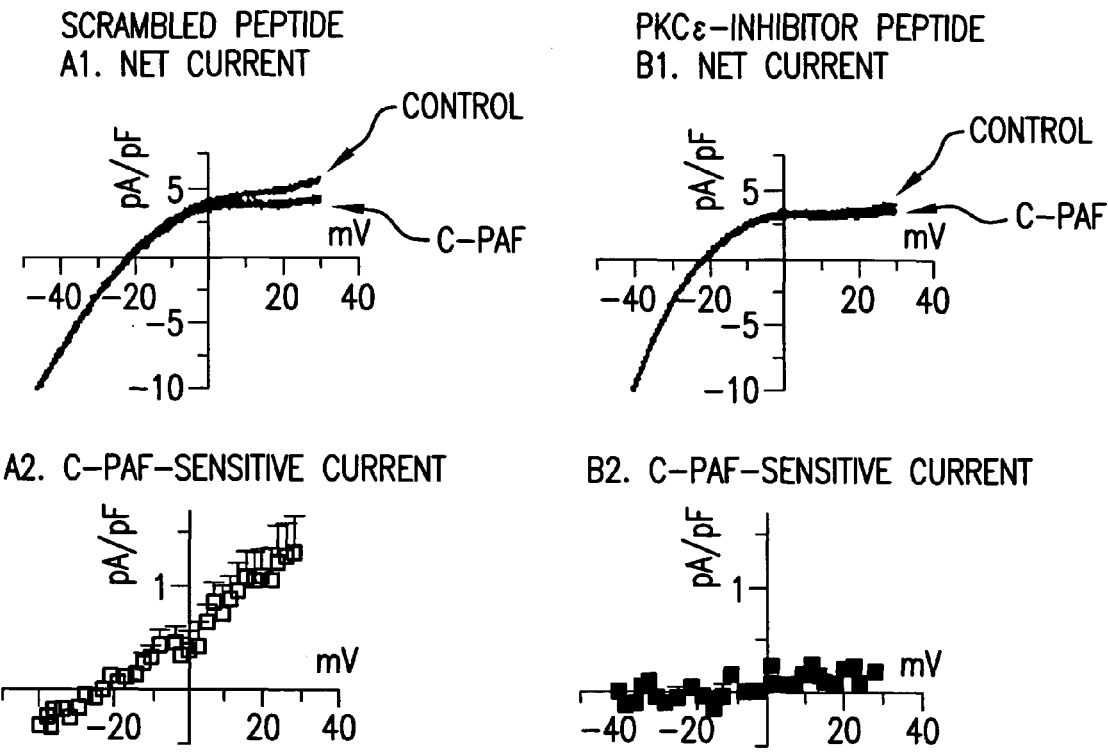
FIGS. 12A-12C. The C-PAF-dependent inhibition of TASK-1 current in mouse ventricular myocytes requires activation of PKCε. Current-voltage relation. C-PAF-sensitive current was recorded in whole cell configuration using a ramp protocol (−50 to +30 mV over 6 s) in modified Tyrode's solution. The recordings started 10-12 min after the rupture of the membrane and C-PAF (185 nM) was applied for 2 min after the current was stable for at least 1 min. C-PAF-sensitive current was obtained as the difference between the mean current (average of 4 successive ramps) at steady state in control and in the presence of C-PAF; the current was normalized by the capacitance of the cell and expressed as current density (pA/pF). 12A(1) depicts the net current from a typical cell before and after C-PAF treatment in the presence of scrambled peptide. 12A(2) depicts the mean. C-PAF-sensitive current recorded from myocytes in the presence of scrambled peptide (100 nM in the pipette; n=8). 12B(1) depicts the net current from a typical cell before and after C-PAF treatment in the presence of inhibitor peptide. 12B(2) illustrates that in presence of the inhibitor peptide the mean C-PAF-sensitive current was abolished (100 nM in the pipette, n=7; *, p<0.05). The mean C-PAF-sensitive current quantified at +30 mV is summarized in 12C.
Figure 12C:
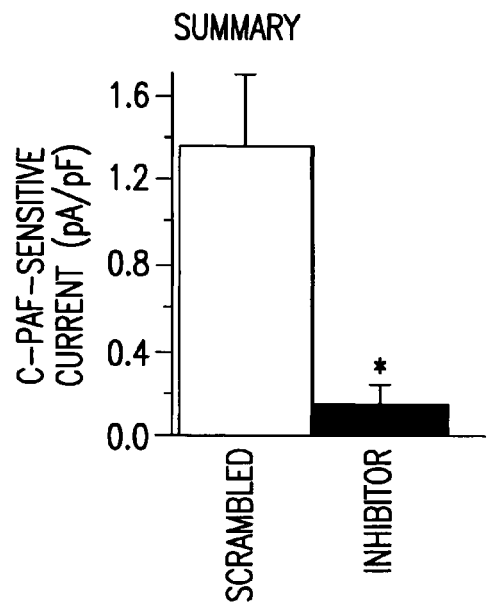

In modified Tyrode's solution, myocytes exposed to the scrambled peptide in the patch pipette had a significant decrease in net current in response to C-PAF (a typical cell is shown in FIG. 12 A1; n=8; p<0.01) that was essentially identical to the effect measured in the absence of peptide in the pipette (data not shown). Typical of TASK-1 in high K$^+$, the C-PAF-sensitive current is nearly linear and has a reversal potential of −26.1±1.9 mV (FIG. 12 A2). In the presence of the inhibitor peptide, however, the C-PAF had virtually no effect on net current (FIG. 12 B1), and the C-PAF-sensitive current was abolished (FIG. 12 B2) indicating that PKCε also plays a crucial role in the regulation of TASK-1 current by PAFR in myocytes. Summary data are shown in FIG. 12C.

PKCε's Role in C-PAF-Induced Repolarization Abnormalities in Isolated Myocytes?

Figure 13A:
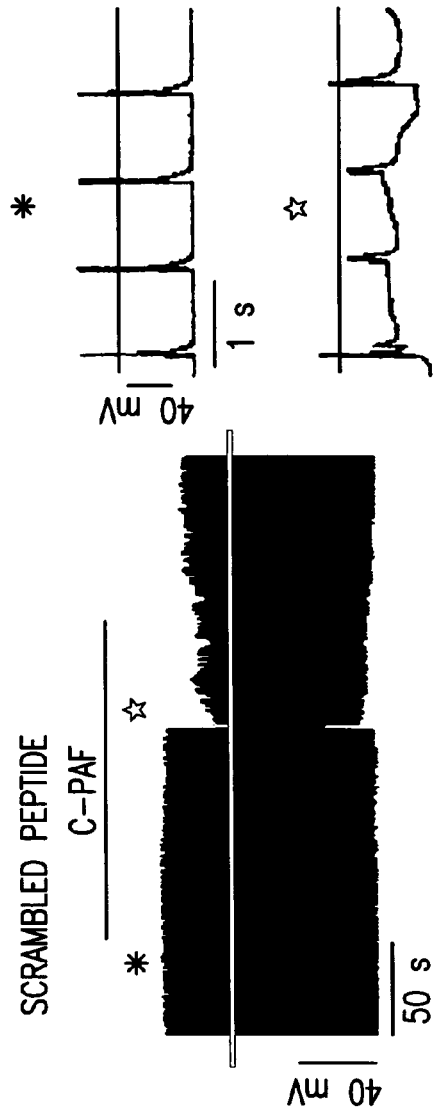
FIGS. 13A-13B. The inhibition of PKCε prevents repolarization abnormalities in paced mouse ventricular myocytes exposed to C-PAF. Action potentials were recorded in current clamp mode from myocytes paced at 1 Hz in regular Tyrode's solution. With no peptide in the pipette, perfusion with C-PAF for 2 min induced repolarization abnormalities in 5 of 7 cells (data not shown) which was similar to the result with the scrambled peptide in the pipette where 14 of 19 cells exhibited repolarization abnormalities during C-PAF perfusion (13A shows the record from a typical cell). In the presence of the inhibitor peptide the effect of C-PAF was completely absent (13B shows a cell typical of 8 studied). Specific areas of interest are: expanded to the right of the record as indicated from control pacing (♦) or during C-PAF application (*). The recordings started 10-12 min after rupture of the membrane. The heavy horizontal line indicates 0 mV in each case.
Figure 13B:
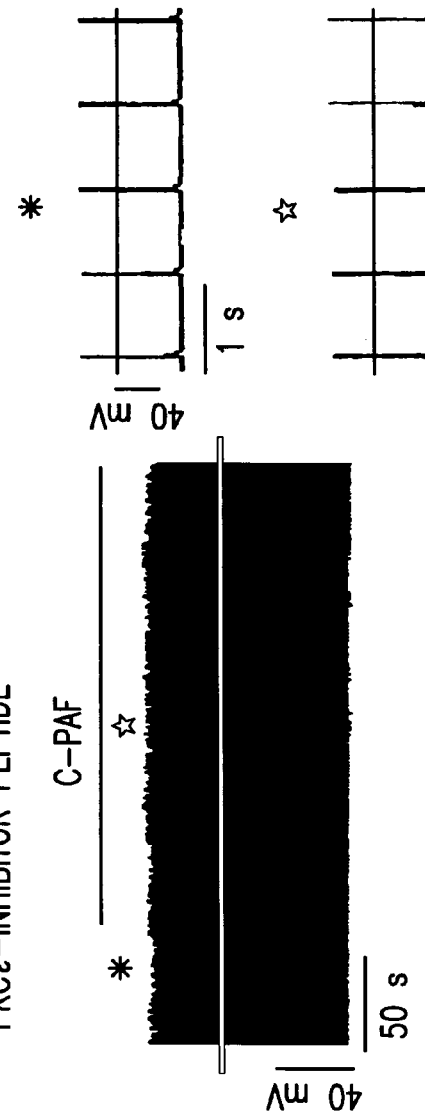

It was previously shown that C-PAF induced abnormal automaticity in paced ventricular mouse myocytes and elicited spontaneous activity in quiescent myocytes (Besana et al., 2004 J. Biol. Chem., 279 (32), 33154-33160). Now, it was questioned whether this abnormal automaticity could be due to PKCε activation. To test this, action potential recordings were done on mouse ventricular myocytes paced at 1 Hz with either the PKCε-specific inhibitor peptide or an inactive scrambled peptide in the pipette (100 nM). Action potentials were continuously monitored, from the rupture of the membrane until the end of the protocol. C-PAF was applied 10-12 min after the rupture. When the scrambled peptide was in the pipette, C-PAF induced abnormalities during repolarization in 14 of 19 cells (FIG. 13A; not different from the response of cells treated with C-PAF in the absence of any peptide). In contrast, C-PAF failed to induce repolarization abnormalities in any of the 8 cells that were exposed to the PKCε-specific inhibitor peptide (FIG. 13B). The difference in observed responses was significant (p<0.001, Fisher's Exact Test).

Figure 14A:
FIGS. 14A-14B. The activation of PKCε mimics the effect of C-PAF to induce repolarization abnormalities during the action potential in mouse ventricular myocytes. AP were recorded in current clamp mode from myocytes paced at 1 Hz in regular Tyrode's solution. When a scrambled peptide was included in the pipette only 2 of 10 cells showed repolarization abnormalities (a typical recording is shown in 14A). In contrast, the presence of the PKCε-specific activator peptide alone, without perfusion of C-PAF, was able to induce EAD and abnormalities during the repolarization of the AP in 8 of 9 cells tested (a typical recording is shown in 14B). Specific areas of interest are expanded to the right of the record as indicated from control pacing (*) or during the effect of the peptide (*). The recordings started immediately after rupture of the membrane. The heavy horizontal line indicates 0 mV in each case.
Figure 14B:
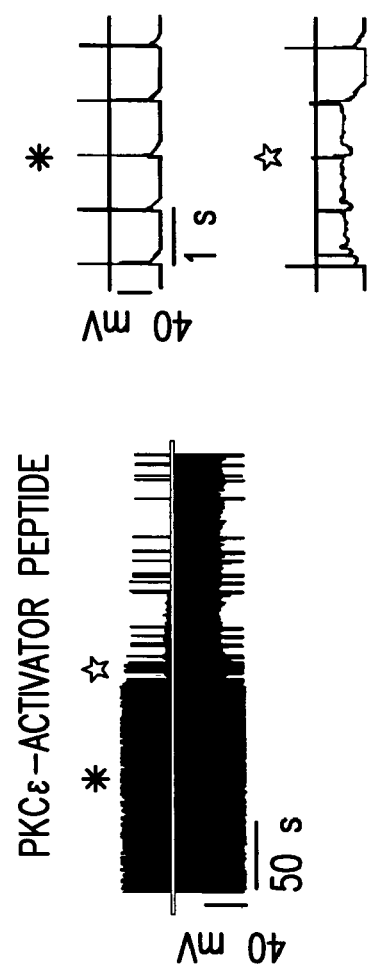

Further confirming that activation of PKCε is sufficient to alter the electrical activity of the myocyte, a specific activator peptide of this kinase included in the patch pipette was observed to induce prolongation of repolarization, early after depolarizations (EAD) and additional spontaneous beats in 8 of 9 cells tested in the absence of any added C-PAF. In these trials, recordings were begun immediately after the rupture of the membrane and abnormal rhythm occurred 5 to 6 min later. Under similar conditions but with the scrambled peptide in the pipette, abnormal automaticity was observed in only 2 of 10 cells tested (FIG. 14; p<0.006; Fisher's Exact Test).

Figure 15A:
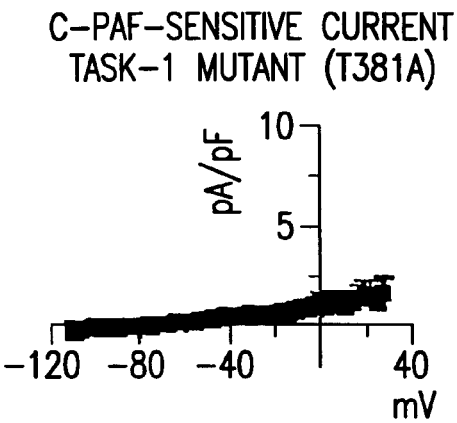
FIGS. 15A-15C. Mutation of threonine-381 removes the sensitivity of murine TASK-1 to C-PAF and PMA when the channel is expressed in CHO cells. A TASK-1 mutant in which T381 was converted to alanine (T381A) was generated and expressed in CHO cells and compared to the wild-type channel. The C-PAF-sensitive current was obtained in Tyrode's at pH 8 using a ramp protocol in whole cell configuration. The mutant channel displayed normal current (in amplitude, sensitivity to pH, reversal potential and shape) but C-PAF (185 nM) did not inhibit the current (n=10; 15A). In each experiment cells transfected with the wild-type channel were used as control for current and C-PAF effect (n=11, 15B). The drug-sensitive currents are calculated as the difference between mean current (average of 4 successive ramps) at steady state in control and in the presence of C-PAF or PMA as noted. C-PAF was applied for 2 min after the current was stable for at least 1 min. PMA was applied for 6 min after the current was stable for at least 1 min. The current was normalized by cell capacitance and expressed as current density (pA/pF). The percent of control TASK-1 current was calculated and the data summarized (15C; *, p<0.05).
Figure 15B:
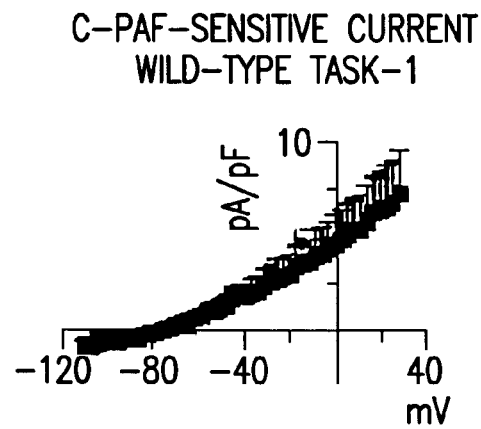
Figure 15C:
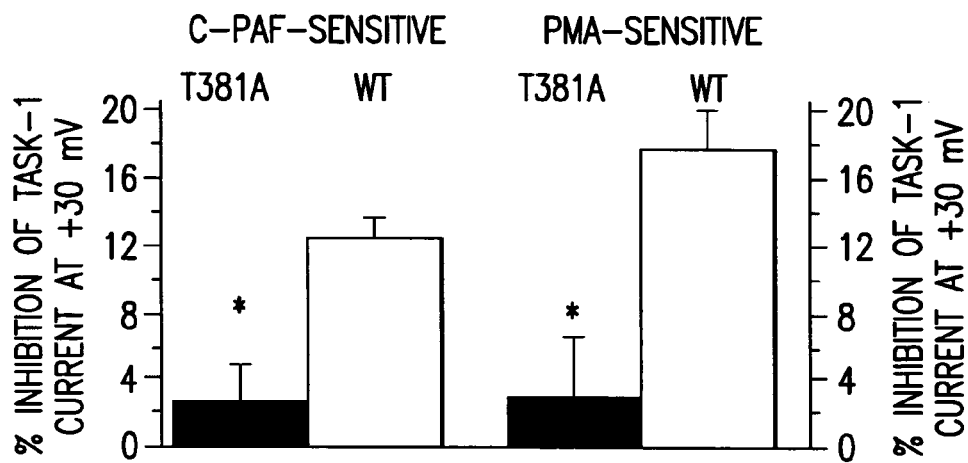

An analysis of the murine TASK-1 sequence revealed a single PKC consensus site which included threonine (residue 381) as the kinase target. Therefore, a site-directed mutant was constructed at this site converting T381 to alanine. The mutant construct, named T381A-pTEE, was expressed in CHO cells and when tested by our typical ramp protocol, demonstrated activity that was comparable to the wild-type channel. However, the mutant channel was no longer sensitive to C-PAF inhibition (maximal current recorded at +30 mV in the absence of C-PAF was 45.5±7 pA/pF versus the current in the presence of C-PAF, 44.2±7 pA/pF; n=10; not significant, FIG. 15). Similar results were obtained when mutant TASK-1 current was tested in the presence of PMA (FIG. 15C, right).

Discussion

It was shown that the abnormalities of repolarization induced by PAF in ventricular myocytes are due to alterations of the background potassium current carried by TASK-1 (Barbuti, A. et al., (2002) Am. J. Physiol. 282, H2024-H2030). Shortly after the channel was cloned, heterologous expression studies showed that TASK-1 was inhibited by PMA and that the inhibition could be blocked by BIM I (Lopes, C. M. B et al., (2000) J. Biol. Chem. 275, 16969-16978), suggesting a role for PKC in the regulation of channel function. Here it is shown that both overexpressed and native TASK-1 are inhibited by activation of the PAFR and that this inhibition is dependent upon the activation of the epsilon isoform of PKC. The activation of PKCε is not only necessary but also sufficient to alter repolarization in isolated myocytes. This sufficiency is evident both by the ability of PMA to inhibit TASK-1 current in CHO cells and by the ability of a PKCε activator peptide to induce abnormal automaticity in myocytes in the absence of added PAF. The results obtained when the TASK-1 channel is over-expressed in a heterologous system support the myocyte data by confirming PAF inhibits TASK-1 in a PKCε-dependent manner. Furthermore, in the heterologous system, PKCε appears to be the only PKC isoform involved in the regulation of murine TASK-1 since blocking PKCε is sufficient to fully block the PMA effect on the channel. Murine TASK-1 has a single consensus PKC site which is threonine-381, a residue in the C-terminal cytoplasmic tail. Using site-directed mutagenesis, this site was mutated replacing threonine with the nonphosphorylatable residue, alanine. The T381A mutant expresses normally in CHO cells but is not inhibited by the addition of C-PAF nor is it sensitive to PMA treatment. The mutagenesis studies allow the recognition of T381 as a critical residue in the PKC-dependent regulation of murine TASK-1 and are supportive of the hypothesis that this site is phosphorylated by PKCε resulting in regulation of the channel. Although human TASK-1 is 83% identical to the murine channel, the PKC site is not in a region that is highly conserved. In fact, the cytoplasmic tail of human TASK-1 contains two putative PKC consensus sequences. Indeed, FIG. 22 shows results obtained in human TASK-1. The T383A mutant is not C-PAF sensitive, and the S358A mutant is not PMA sensitive.

In addition to TASK-1, several other two pore-domain channels are regulated by kinase activity although the molecular mechanisms that underlie the regulation are not entirely clear. For example, TREK-1 (Kim D et al. (1998) Circ Res 82: 513.-518) and its putative invertebrate homologue, the Aplysia S-K channel (Shuster, M. J. Et al., (1985) Nature 313, 392-395), are inhibited by a cyclic-AMP-dependent protein kinase phosphorylation in the C-terminal cytoplasmic tail (Bockenhauer, D. et al., (2001) Nat. Neurosci. 4, 486-491; Maingret, F. et al., (2002) Biochem. Biophys. Res. Commun. 292, 339-346). In both channels the effect is due to a change in the open probability of the channel. Human TWIK-1 and TWIK-2 are activated by application of PMA when expressed in oocytes (Lesage, F. et al., (1996) EMBO J. 15, 1004-1011; Chavez, R. A. et al., (1999) J. Biol. Chem. 274, 7887-7892). There does not appear to be any change in the single channel conductance. Rather, PMA appears to recruit previously silent channels within the cell-attached patch. In this case, however, there is no direct evidence of TWIK channel phosphorylation and thus, the possibility that the altered channel function may be mediated by kinase action on a second protein cannot be discounted.

Single channel studies of the Drosophila two pore-domain channel, Kcnk0, have described three gating states: one open and two closed. The two closed states are typified by either short or long intraburst closures. When the channel is phosphorylated, the open probability of the channel increases due to a decrease in the frequency and duration of the long-lasting closed state resulting in an increase in the total current (Zilberberg, N. et al., (2000) J. Gen. Physiol. 116, 721-734).

Thus, kinase dependent modulation of two pore-domain channels is generally associated with altered open probability rather than a change in single channel conductance. In the case of TASK-1, four gating states have been proposed: two open (one principal and one substrate with different conductance) and two closed (Maingret F et al.(2001) EMBO J. 20: 47-54; Shukia S D. (1992) FASEB J 6: 2296-2301). By analogy to other two pore-domain channels, phosphorylation of murine TASK-1 at T381 and human TASK-1 might decrease the total current by favoring gating of the substrate relative to the principal conductance state, decreasing mean open time, or increasing mean closed time. Single channel studies will be needed to reach a clear conclusion on this mechanism. Nevertheless, it does seem clear that channel regulation through activation of PKCε differs fundamentally from inhibition induced by methanandamide since neither PMA nor PAF reduce the current more than 20% while methanandamide inhibition typically reaches approximately 60% (Barbuti, A. et al., (2002) Am. J. Physiol. 282, H2024-H2030).

The role of PKCε in cardiac function is complicated by observations that this isoform can mediate the cardioprotective events of ischemic preconditioning (Ping, P. et al., (1997) Circ. Res. 81, 404-414, and reviewed in Armstrong, S. C. (2004) Cardiovasc. Res. 61, 427-436) and under other conditions plays a lead role in the development of hypertrophy and failure (Pass, J. M. et al., (2001) Am. J. Physiol. 280, H946-H955). Some of the explanation for these dichotomous results may lie in the variability of the level of expression of the kinase and in the subsequent control of its subcellular localization and formation of signaling complexes. For example, it has been shown that PKCε localizes in complexes at mitochondrial membranes after brief repeated episodes of ischemia. Could this sequester enough of the kinase to prevent its association with TASK-1 in the plasma membrane and thereby prevent the arrhythmogenic reduction in this background $K^+$ current. Pharmacological antagonism of the PAFR or ischemic preconditioning are both able to significantly reduce the occurrence of ventricular ectopic beats after coronary occlusion (Sariahmetoglu, M. et al. (1998) Pharmac. Res. 38, 173-178) but likely work by different mechanisms. The effect of the PAFR antagonist is consistent with the known sequence of events that include cardiac generation of PAF during ischemia leading to inhibition of TASK-1 via a PKCε-dependent pathway and subsequent generation of abnormal repolarization in ventricular myocytes. This pathway may not occur after preconditioning if the repeated ischemic events lead to movement of PKCε away from the site where it may interact with TASK-1.

The transient nature of the C-PAF induced current in isolated myocytes has previously been noted. This is also evident in FIG. 11, and is presumably due to desensitization of the signaling cascade. It is not known if the response is equally transient in the in situ heart. However, even a transient repolarization abnormality, if induced on the appropriate myocardial substrate as might be found in a diseased heart, could initiate a sustained arrhythmic event. In this regard, the outward rectifying nature of the TASK-1 I-V relation makes it particularly relevant to the plateau phase of the action potential. The plateau represents a period of high membrane resistance where even small currents can exert a significant effect. It is well recognized that reduction in net outward current during the action potential plateau can lead to action potential prolongation and subsequent arrhythmias through the activation of other currents (Anderson, M. E., Al Khatib., S. M., Roden, D. M., and Califf, R. M. (2002) Am. Heart J. 144, 769-781). Further, in the setting of cardiac disease down regulation of outward $K^+$ currents can result, in reduction of "repolarization reserve" (Roden, D. M. (1998) Pacing Clin. Electrophysiol. 21, 1029-1034) such that even a small further decrease in net outward current can lead to marked action potential prolongation and arrhythmogenesis. In these experiments it is likely that there is a progressive inhibition of TASK-1 current either by C-PAF or the activator peptide activating PKCε.

However, due to the repolarization reserve a marked failure of repolarization and subsequent arrhythmias does not occur until the current is reduced beyond a critical threshold level. This accounts for the delay in the onset of arrhythmias during C-PAF superfusion, and suggests that PAF-induced inhibition of TASK-1 current is likely to be particularly arrhythmogenic in the context of cardiac disease, where other $K^+$ currents are already compromised.

Materials and Methods

Myocyte Preparation

Mouse ventricular myocytes were isolated using a retrograde coronary perfusion method previously published (Kuznetsov V et al. (1995) Circ Res 76: 40-52). All the experiments were carried out according to the guidelines issued by the IACUC of Columbia University. Adult mice 2 or 3 months old, were anaesthetized with a xylazine and ketamine mix and heparinized, the heart was quickly removed and the ascending aorta was connected to the outlet of a Langendorff column and perfused with 20-25 ml of a buffer solution (37° C.) containing (mM):NaCl, 112; KCl, 5.4; $NaHCO_3$, 4.2; $MgCl_2$, 1.6; HEPES, 20; glucose, 5.4; $NaH_2PO_4$, 1.7; taurine, 10; L-glutamine, 4.1; MEM amino acids solution, 2%; MEM vitamin solution, 1%; adjusted to pH 7.4, and equilibrated with 100% $O_2$. Next, the heart was perfused with an enzyme solution containing collagenase (0.2 mg/ml; Worthington Type II) and trypsin (0.04 mg/ml) at 35° C. for 10-12 min. After this perfusion, the atria were removed and the ventricles minced and transferred to a 50 ml flask with an enzyme solution containing collagenase (0.45 mg/ml), trypsin (0.08 mg/ml), $Ca^{2+}$ (0.75 mM) and bovine serum albumin (BSA; 4.8 mg/ml). The flask was shaken vigorously for 5-10 min at 32° C. before the supernatant was removed and the cells were collected by centrifugation, this operation was repeated two or three times and additional disaggregated cells were collected. After centrifugation, the myocytes were resuspended in the buffer solution containing $Ca^{2+}$ (0.75 mM) and BSA and stored at room temperature until use. Rod-shaped, $Ca^{2+}$-tolerant myocytes, obtained with this procedure, were used within 6 h of dissociation. Measurements were performed only on quiescent myocytes with clear striations Plasmids pCMV-TASK1 (cTBAK) consists of a 1.9 kb sequence of murine TASK-1 inserted in pcDNA3.1 (a kind gift of Dr. Yoshihisa Kurachi, University of Osaka, Japan) and has been previously described (Leonoudakis D et al. (1998) J Neurosci 18: 868-877). pEGFP-C1 and pIRES-EGFP were purchased from Clontech. pTIE (TASK1-IRES-EGFP) was constructed by inserting a 1.9 kb EcoR1 fragment from pCMV-TASK1 into EcoR1 digested pIRES-EGFP. Site-directed mutagenesis was performed on pTIE using the Quik-Change kit (Stratagene) following the manufacturer's instructions. Primers were designed to generate a mutation in pTEE where threonine-381 was converted to alanine (T381A-pTEE): forward-5'-TGCCTGTGCAGCGGGGCGCACGCTCGGC-CATCAGCTCG-3' (SEQ ID NO: 1) and reverse-5'TCGAGCTGATGGCCGAGCGCTGCGCCCCGCTGCACAGGCA-3' (SEQ ID NO:2).

Cell Culture and Transfection

Chinese hamster ovary cells (CHO) were grown in F-12 medium supplemented with 10% fetal bovine serum. Twenty-four hours prior to transfection, cells were seeded into 6 well plates at 80-90% of confluence. Transfections were carried out with the GeneJammer transfection reagent (Stratagene) according to the manufacturer's instructions. Briefly, cells were washed with PBS and their medium replaced with supplemented F-12 medium (900 μl/well). For each well, GeneJammer (6 μl) was incubated with Opti-MEM (90 μl) followed by the addition of DNA (1 μg). This mixture was then added to the wells and 3 h later an additional 2 ml of supplemented F-12 medium was added. After incubating overnight, the cells were washed and their medium replaced.

Cells were either co-transfected with pCMV-TASK1 together with pEGFP-C1 (1 μg total, 3:1) or transfected with pTEE or T381A-pTIE (1 μg). 48 h after the transfection the cells were checked under the microscope for green fluorescence. Approximately 20% of the cells were positive for EGFP and these were then used for patch-clamp experiments. Due to the culture-to-culture variability in the expression of TASK-1 current, most comparisons were made on matched controls from the same transfection. Summary results were then obtained by pooling data from several different culture preparations.

Solutions and Recording Apparatus

The myocyte suspension or the coverslip with CHO cells was placed into a perfusion chamber, mounted on the stage of an inverted microscope. Unless otherwise indicated, CHO cells were superfused at room temperature with standard external Tyrode's buffer, containing (mM): NaCl, 140; KCl, 5.4; $CaCl_2$, 1; $MgCl_2$, 1; HEPES, 5; glucose, 10; adjusted to pH 7.4. Recordings were begun after the current reached a stable baseline (usually 3 to 4 min after initial cell rupture). In myocytes, TASK-1 current is small and exists in the presence of numerous larger $K^+$ currents. In order to increase the inward component of TASK-1 current and to block other potassium currents in myocytes, a modified high $K^+$ external solution (modified Tyrode's) was used to reduce outward rectification of TASK-1 current. The composition of this solution-was (in mM): NaCl, 100; KCl, 50; $CaCl_2$, 1; $MgCl_2$, 1; HEPES, 5; glucose, 10; tetraethylammonium (TEA), 1; CsCl, 5; adjusted to pH 7.4. Membrane potential and current were measured in the whole cell configuration using borosilicate glass pipettes with a tip resistance between 3 and 5 Mg and filled with a pipette solution containing (mM): aspartic acid, 130; KOH, 146; NaCl, 10; $CaCl_2$, 2; EGTA, 5; HEPES, 10; MGATP, 2; pH 7.2. The stock solutions of C-PAF and of the PKC inhibitor, bisindolylmaleimide (BIM-I; Calbiochem), were prepared in water and diluted to the final concentrations in Tyrode's or modified Tyrode's, as appropriate. The PKC activator, PMA, was prepared in DMSO and then diluted in Tyrode's. The final DMSO concentration did not exceed 0.1% and the same concentration was present in the control solution. The peptides, εV1-2 [EAVSLKPT; (Johnson, J. et al. (1996) J. Biol. Chem. 271, 24962-24966)] and εV1-7 [HDAPIGYD; (Dorn, G. W. et al., (1999) Proc.Natl. Acad. Sci. U.S. A. 96, 12798-12803; Hu, K. et al. (2000) Am. J. Physiol. 279, H2658-H2664)], PKCε-specific inhibitor and activator, respectively and an inactive scrambled peptide [LSETKPAV, (Johnson, J., et al. (1996) J. Biol. Chem. 271, 24962-24966)] were synthesized by the Columbia University Protein Core. Peptides were prepared in water and then diluted in the pipette solution to a final concentration of 100 μM. Myocytes treated with the peptides were monitored continuously beginning immediately after rupture to detect the occurrence of any arrhythmias during dialysis of the peptide. Application of C-PAF to cells treated with the inhibitor peptide was started after the peptide had been permitted to dialyse into the cell (8-10 min after rupture for CHO or 10-12 min after rupture for myocytes).

The current and the voltage protocols were generated using Clampex 8.0 software applied by means of an Axopatch 200-B and a Digidata 1200 interface (Axon Instruments). In current clamp mode, for recording action potentials, the signals were filtered at 1 KHz (low pass Bessel filter) and acquired at a sampling rate of 5 KHz. In voltage clamp mode, the current signals were filtered at 1 KHz and acquired at 500 Hz.

Data Analysis and Statistics

Data were analyzed using pCLAMP 8.0 (Axon) and Origin 6.0 (Microcal) and are presented as mean±SEM. Records have been corrected for the junction potential, which was measured to be −9.8 mV. Steady state currents were determined by computer calculation of average current over at least 1 min. Unless otherwise stated, current density comparisons were determined at a voltage of +30 mV. Current density changes are expressed as percent inhibition in CHO cell experiments where TASK-1 is essentially the only current and a pre-treatment baseline current can be readily recorded. In myocytes TASK-1 is measured as the drug-sensitive current and thus, it is not possible to measure a baseline current to normalize the result when studying the effect of C-PAF or PMA on TASK-1. Therefore, changes in this current in myocytes are expressed in absolute values (pA/pF). Fisher's exact test was used to test the significance of frequency data and Student's t-test was used to compare paired or independent data; a value of $\leq 0.05$ was considered statistically significant.

Example 3

Figures 16A, 16B:
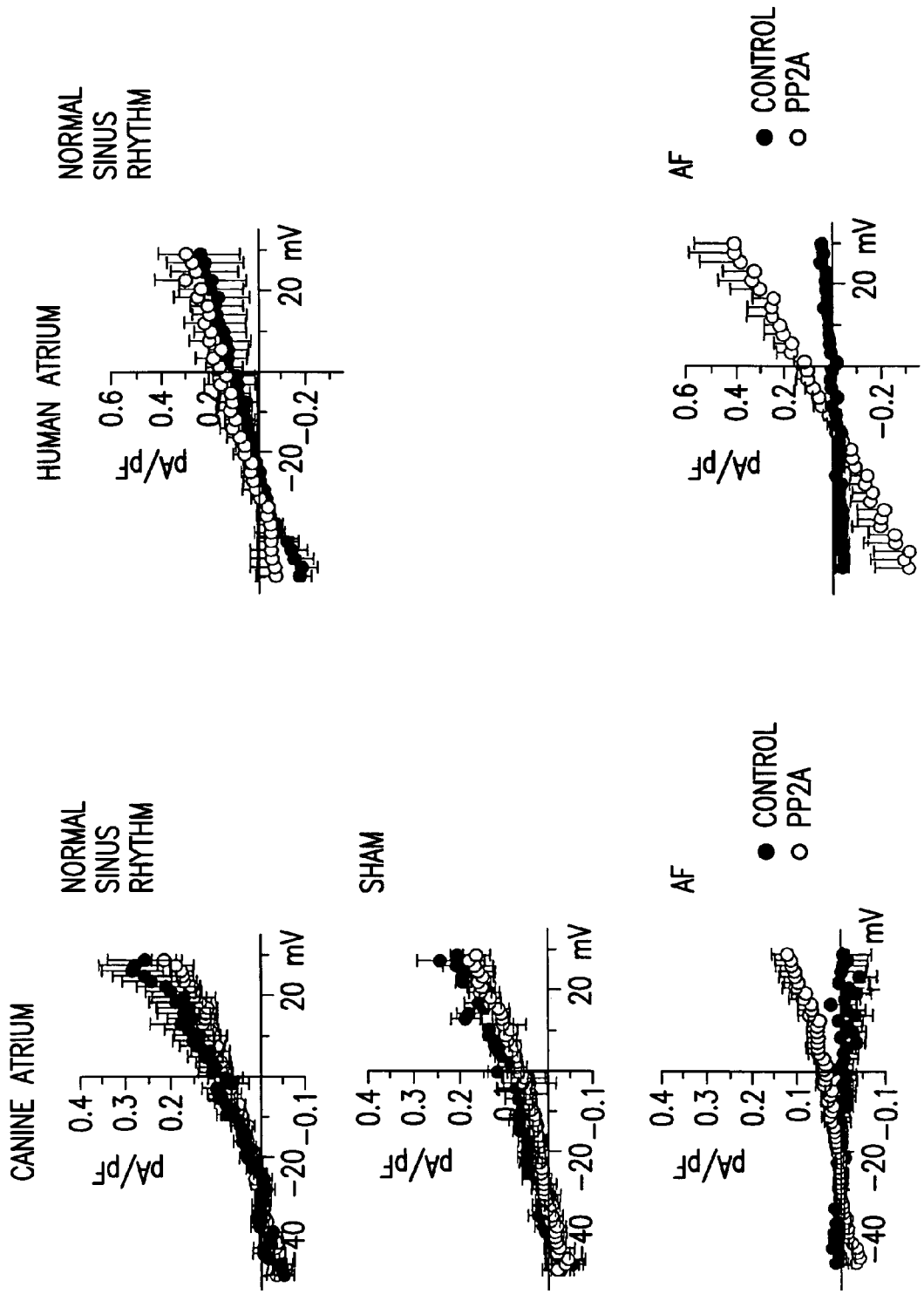
FIGS. 16A-16B. There is phosphorylation-dependent loss of TASK-1 current in both canine and human AF. 16A: TASK-1 current, measured as the methanandamide-sensitive difference current in 50 mM external $K^+$, in canine atrial myocytes from a control dog (top), a sham operated dog (middle) and a dog in chronic AF (bottom), using normal pipette solution (filled symbols) and pipette solution containing the phosphatase, PP2A (unfilled symbols). Data illustrate the loss of current in AF and its rescue by PP2A. 16B: TASK-1 current in human atrial myocytes from patients in normal sinus rhythm (top) and patients in AF (bottom). PP2A has no effect on TASK-1 current in human myocytes from patients in normal sinus rhythm. In the case of AF, data were collected from separate sets of cells using normal pipette solution (filled symbols) and with pipette solution containing PP2A. Data illustrate the loss of TASK-1 current in AF and its rescue by PP2A.

It was found that there is a loss of TASK-1 current (FIGS. 16A and 16B) measured as the methanandamide-sensitive current, in atrial myocytes isolated from either canine or human hearts that are in atrial fibrillation (AF). FIG. 16 shows that this current can be rescued by the addition of a phosphatase, PP2A, to the patch pipette even though the phosphatase alone has no effect on control current. FIG. 16 (top), shows that the TASK-1 current normally expressed in atrial myocytes derived from canine (16A) and human (16B) hearts in normal sinus rhythm is not affected by the addition of PP2A to the patch pipette. However, this current is absent in atrial myocytes from AF hearts (16B, bottom, filled circles). The current is rescued when PP2A is included in the patch pipette (16B, bottom, unfilled symbols).

Western blot analysis of 2PK channel expression in dog and human heart was also performed (see FIG. 17). Membrane fractions were prepared from atria of hearts that were either in normal sinus rhythm (NSR) or in chronic atrial fibrillation (AF). Equal amounts of protein were loaded to each lane and the mixtures were separated by SDS-PAGE. Proteins in the gel were transferred to nitrocellulose and the blot was probed with anti-TASK-1 and anti-TREK-1. The signal was detected with an enhanced ECL system.

Figure 18:
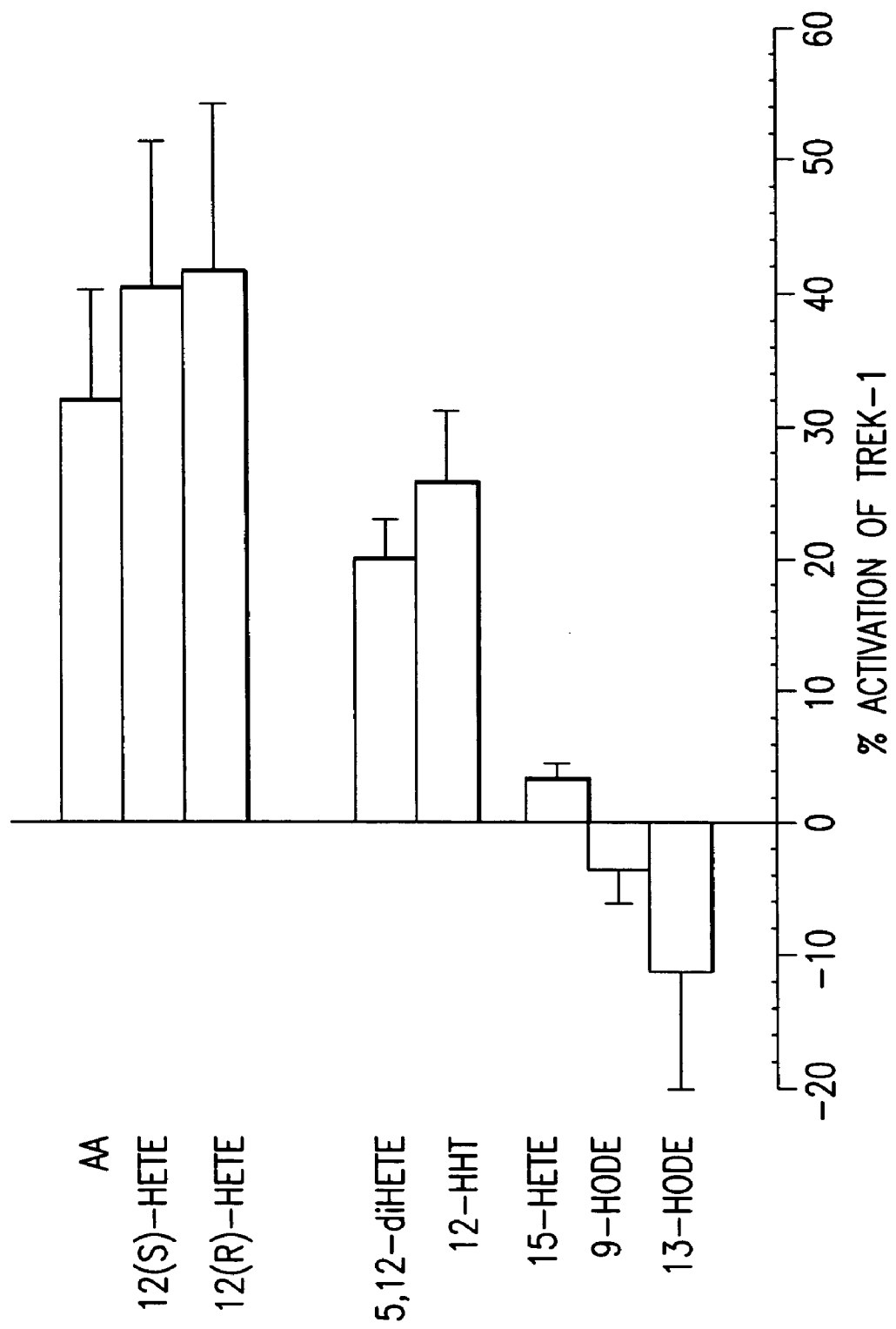
FIG. 18. Structure-activity analysis of activators of human TREK-1 channel. Human TREK-1 was expressed in CHO cells and current was measured during a ramp protocol (−120 to +50 mV in 6 s). The activation of the current at +50 mV in the presence of various putative TREK-1 activators was measured and summarized in the bar graph as % activation over basal. Various endogenous lipids, most related to lipoxygenase metabolites of either arachidonic acid or linoleic acid, were tested (all at 100 nM).
Figure 19:
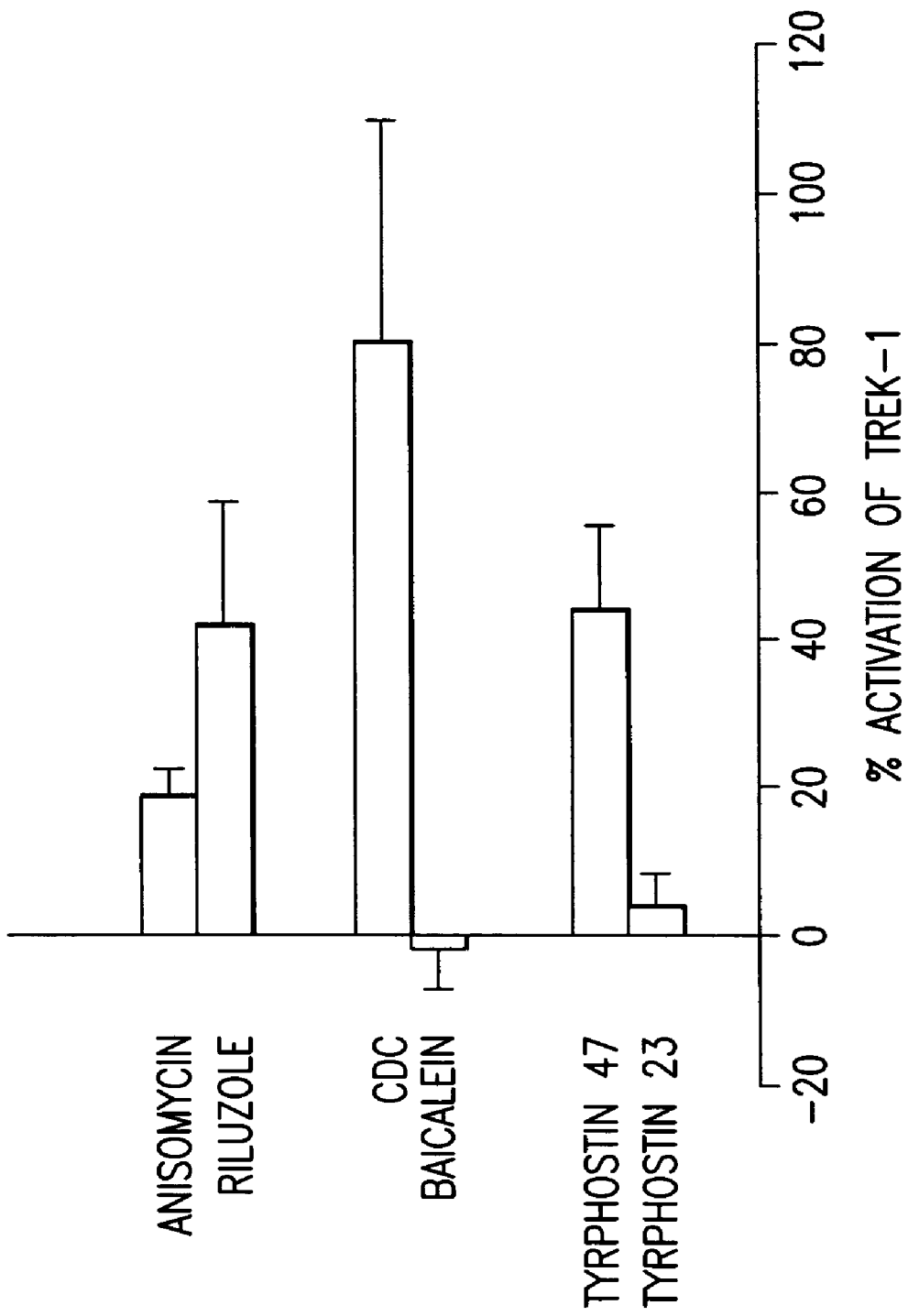
FIG. 19. Structure-activity analysis of activators of human TREK-1 channel. Three groups of activators were tested including slow-onset activators, riluzole (100 nM) and anisomycin (3.7 µM), and rapid-onset activators, caffeic acid esters (CDC, 10 µM) and tyrphostins (10 µM).
Figure 20:
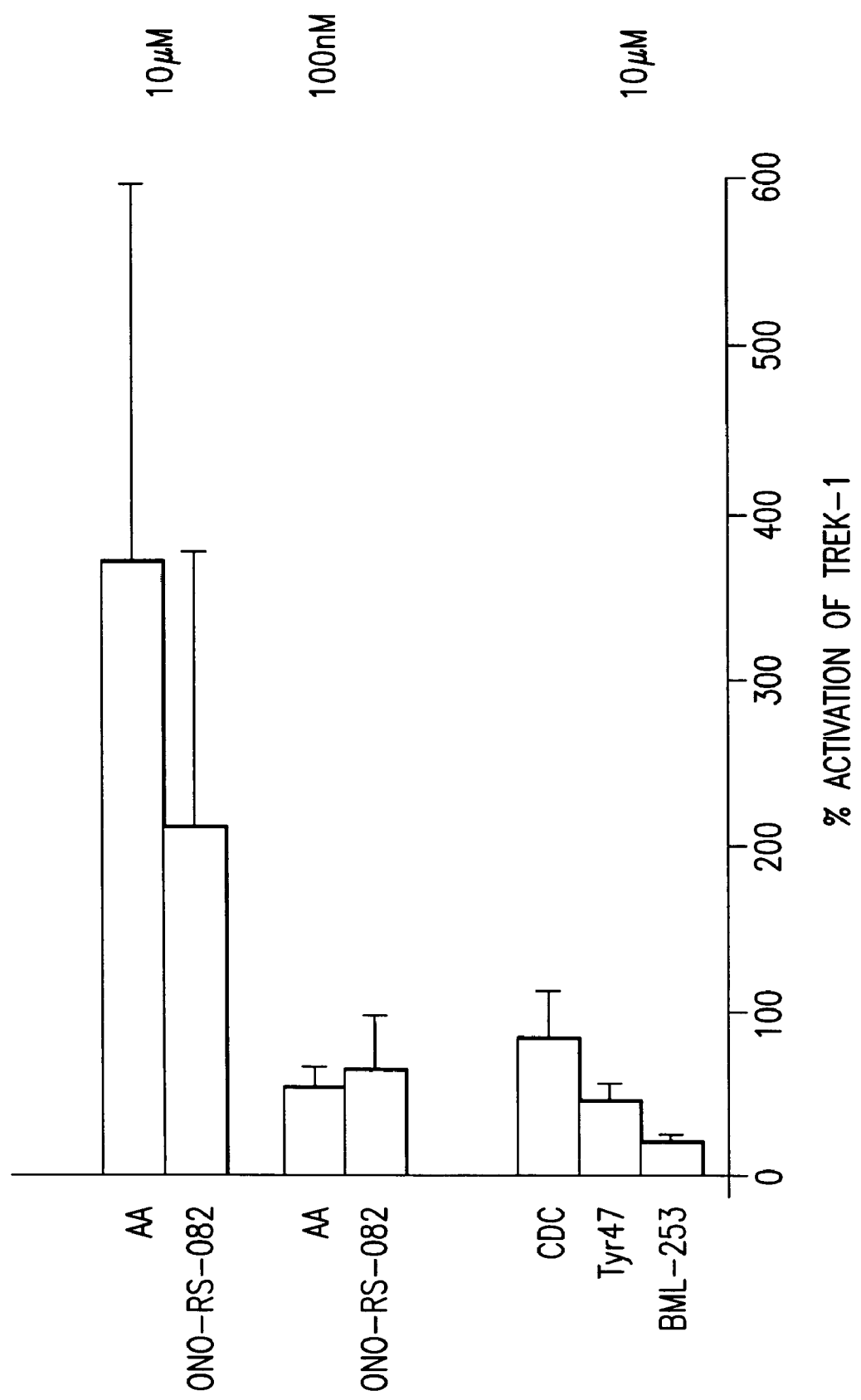
FIG. 20. Structure-activity analysis of activators of human TREK-1 channel. ONO-RS-082 was tested and compared to arachidonate, CDC and several tryphostins (doses varied from 100 nM to 10 µM, as shown).
Figure 21:
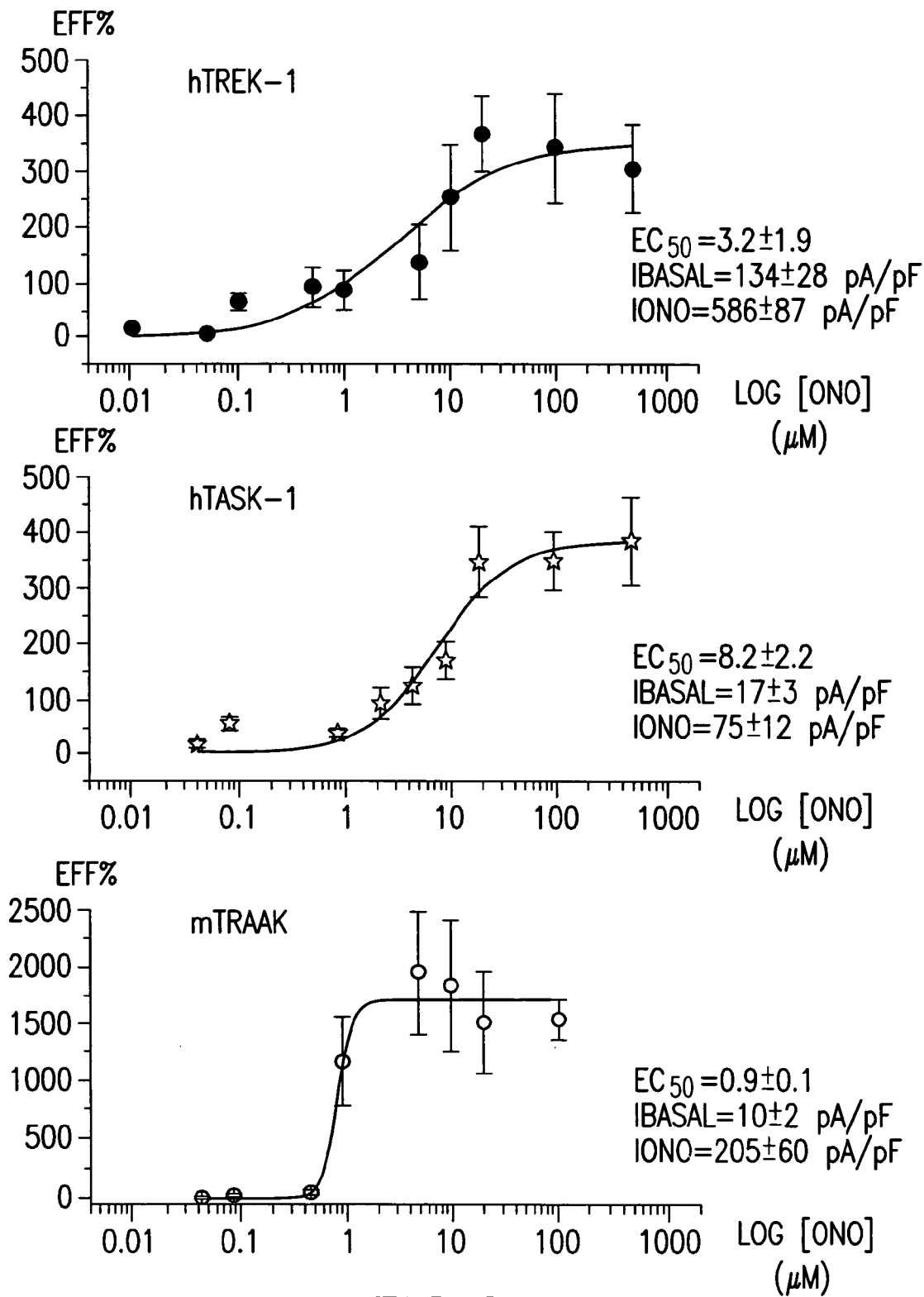
FIG. 21. CHO cells (hTREK-1, hTASK-1) or HEK cells (mTRAAK) were co-transfected with plasmids encoding one of the two pore domain channels and GFP using the Gene-Jammer reagent. After 48-60 h, the expressed current was measured using a ramp protocol while the cells were perfused with regular Tyrode's solution containing varying concentrations of ONO-RS-082 (range of concentration from 10 nM to 500 µM as noted in FIG. 21) until a steady state was reached. Each cell was exposed to only one concentration of drug. Panel A: TREK-1 current was determined using a ramp clamp, and the percent increase induced by ONO-RS-082 was measured at the most positive imposed voltage (n≧5). The $EC_{50}$ for activation was around 3 µM and the basal and ONO-activated current densities are noted. Panel B: TASK-1 current was determined using a ramp clamp in Tyrode's solution at pH=8 and the percent increase induced by ONO-RS-082 was measured at the most positive imposed voltage (n≧4). The $EC_{50}$ was around 8 µM and the basal and ONO-activated current densities are noted. Panel C: TRAAK current was determined using a ramp clamp, and the percent increase induced by ONO-RS-082 was measured at the most positive imposed voltage (n≧4). The $EC_{50}$ was around 0.9 µM and the basal and ONO-activated current densities are noted.
Figure 22B:
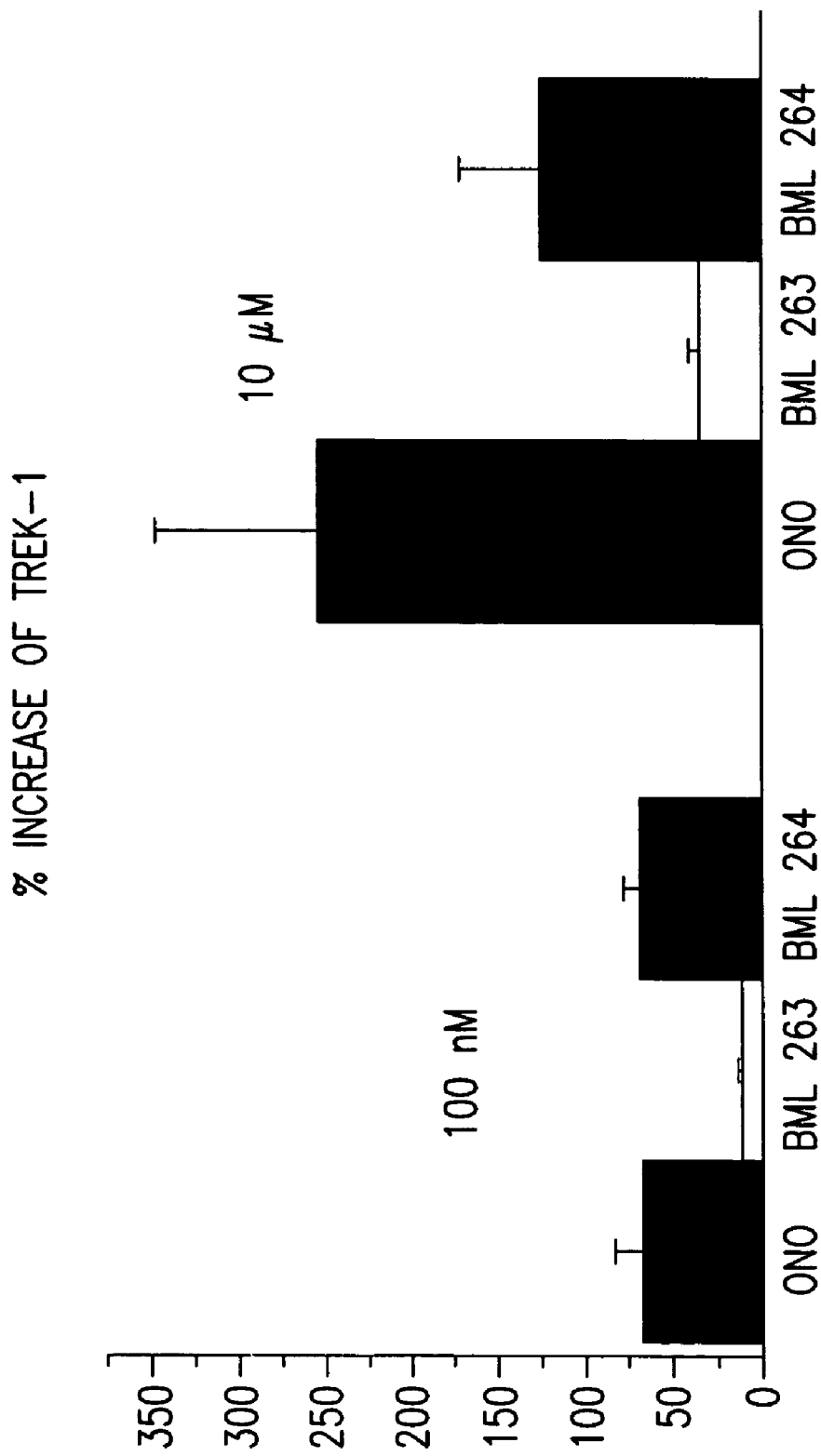

Subsequently, the structure-activity analysis of activators of human TREK-1 channel was determined. FIGS. 18-20 show that human TREK-1 was expressed in CHO cells and current was measured during a ramp protocol (−120 to +50 mV in 6 s). The activation of the current at +50 mV in the presence of various putative TREK-1 activators was measured and summarized in the bar graph as % activation over basal. As shown in FIG. 18, various endogenous lipids, most related to lipoxygenase metabolites of either arachidonic acid or linoleic acid, were tested (all at 100 nM). FIG. 19 shows three groups of activators were tested including slow-onset activators, riluzole (100 nM) and anisomycin (3.7 μM), and rapid-onset activators, caffeic acid esters (CDC, 10 μM) and tyrphostins (10 μM). FIG. 20 shows ONO-RS-082 was tested and compared to arachidonate, CDC and several tryphostins (doses varied from 100 nM to 10 μM, as shown). FIG. 21 demonstrates ONO-RS-082 activation of several two-pore channels in a dose dependent manner. FIG. 22A-B demonstrates the activity of two ONO-RS-082 analogues.

Figure 31:
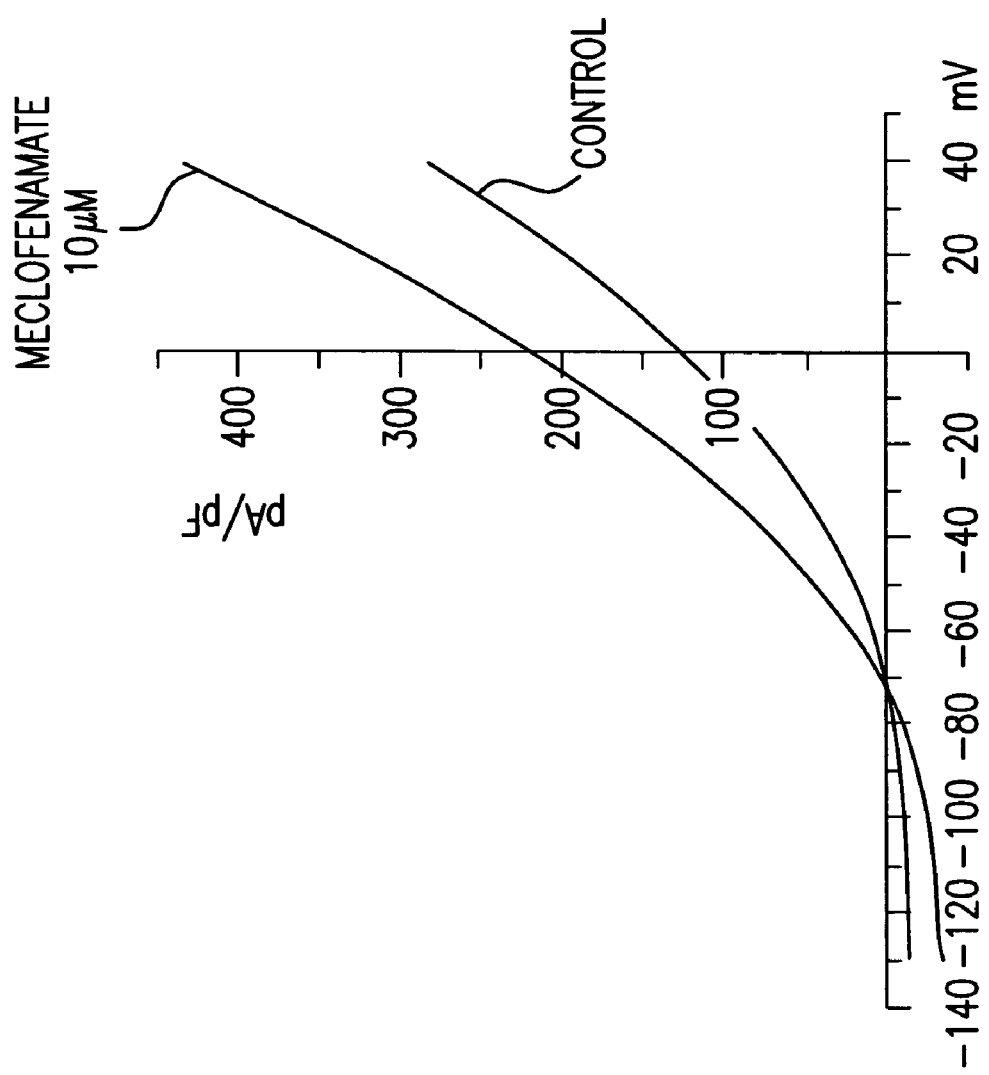
FIG. 31. Meclofenamate activates TREK-1 current in CHO cells that heterologously express the channel. CHO cells were transfected with a plasmid encoding human TREK-1 and the current was studied by patch clamp. The current-voltage relation was determined using a ramp protocol that went from −130 mV to +40 mV in 6 s (after correction for the junction potential). Current was greater in the presence of meclofenamate. This is typical of 7 cells.

FIG. 31 reveals that Meclofenamate activates TREK-1 current in CHO cells that heterologously express the channel. CHO cells were transfected with a plasmid encoding human TREK-1 and the current was studied by patch clamp. The current-voltage relation was determined using a ramp protocol that went from −130 mV to +40 mV in 6 s (after correction for the junction potential). Current was greater in the presence of meclofenamate. This is typical of 7 cells.

Figure 23A:
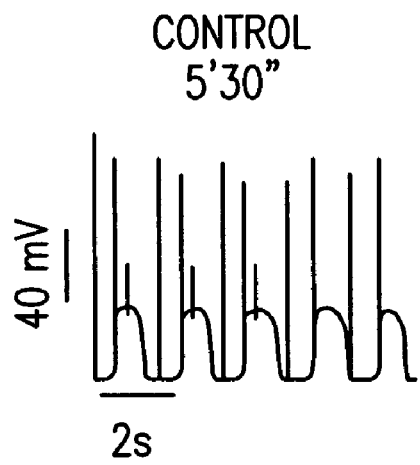
FIGS. 23A-23D. Activation of TREK-1 can overcome arrhythmias induced by inhibition of TASK-1. Isolated murine ventricular myocytes were studied in current clamp mode and paced at 1 Hz. The cells were studied in regular Tyrode's, pH 7.4. Recordings were begun immediately after rupture and continued for 12-15 min, with the 5.5 min time point illustrated. A PKCε-specific activator peptide (100 nM) was included in the patch pipette, which lead to inhibition of TASK-1 current and repolarization abnormalities (23A and 23B). However, when TREK-1 was simultaneously activated by superfusion of the myocytes with either arachidonic acid (AA, 100 nM) or tyrphostin 47 (50 µM) beginning 1 min after rupture, the PKCε-specific activator peptide induced fewer arrhythmias (23C and 23D).
Figure 23B:
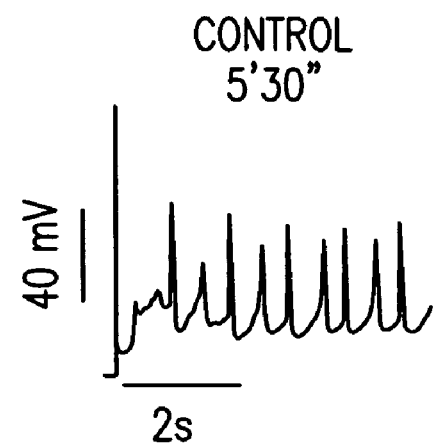
Figure 23C:
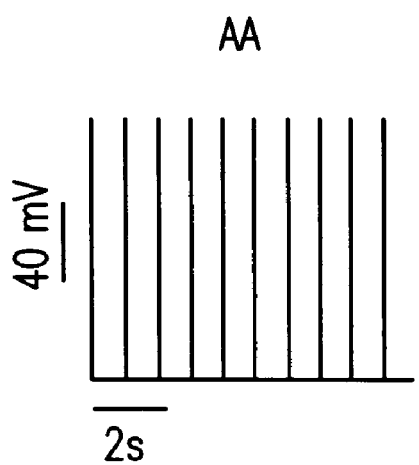
Figure 23D:
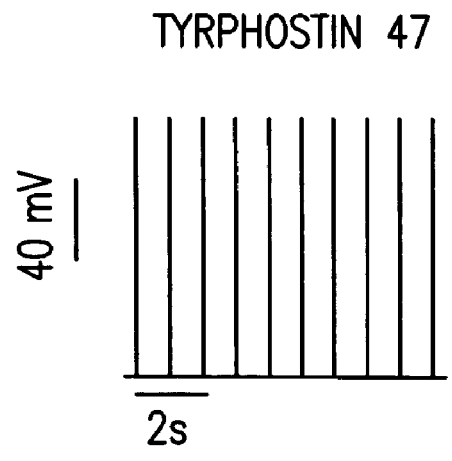
Figure 25A:
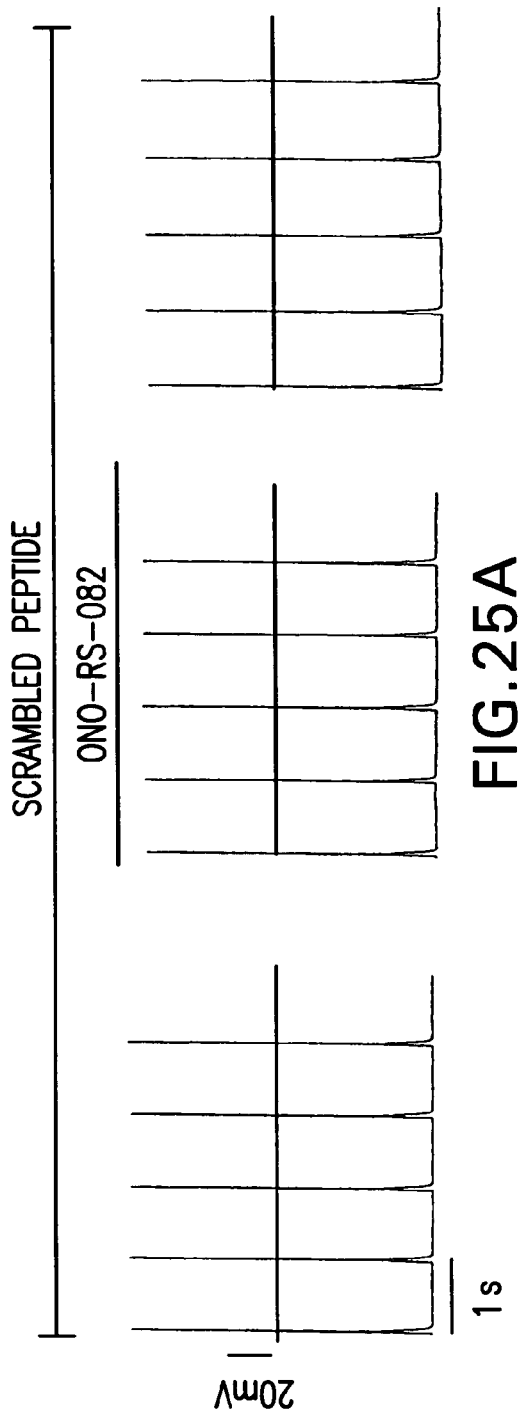
FIG. 25. Activation of TREK-1 can overcome arrhythmias induced by inhibition of TASK-1. Isolated murine ventricular myocytes were studied in current clamp mode and paced at 1 Hz. The cells were studied in regular Tyrode's, pH 7.4. Recordings were begun immediately after rupture and continued for 12-15 min. A PKCε-specific activator peptide (100 nM) (23B) or a scrambled control peptide (100 nM) (25A) was included in the patch pipette. After the activator peptide had induced repolarization abnormalities (25B left panel), a TREK-1 activator, ONO-RS-082 (100 nM) was added to the superfusion. The addition of this drug promptly reversed the arrhythmia (25B center panel). When ONO-RS-082 was removed and allowed to washout, the arrhythmias recurred (25B right panel).
Figure 25B:
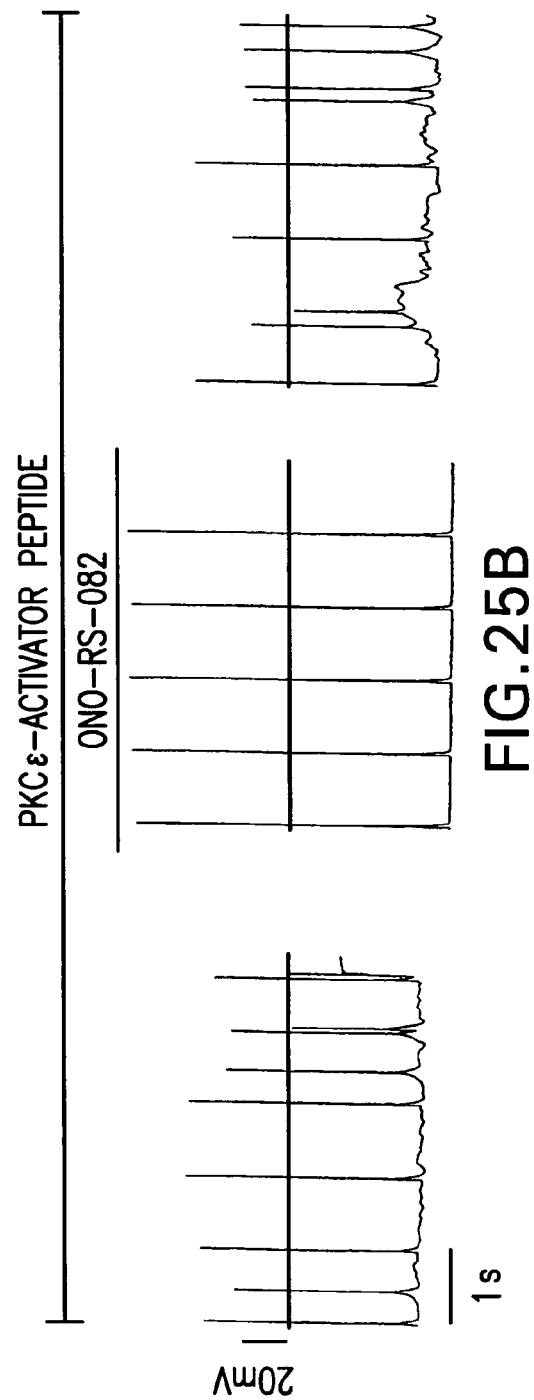

It was revealed that activation of TREK-1 can overcome arrhythmias induced by inhibition of TASK-1. Isolated murine ventricular myocytes were studied in current clamp mode and paced at 1 Hz. The cells were studied in regular Tyrode's, pH 7.4, and recordings were begun immediately after rupture and continued for 12-15 min, with the 5.5 min timepoint illustrated. As shown in FIGS. 23A and 23B, a PKCε-specific activator peptide (100 nM) was included in the patch pipette which lead to inhibition of TASK-1 current and repolarization abnormalities. However, when TREK-1 was simultaneously activated by superfusion of the myocytes with either arachidonic acid (AA, 100 nM) or tyrphostin 47 (50 μM), beginning 1 min after rupture, the PKCε-specific activator peptide induced fewer arrhythmias (FIGS. 23C and 23D).

Figure 26:
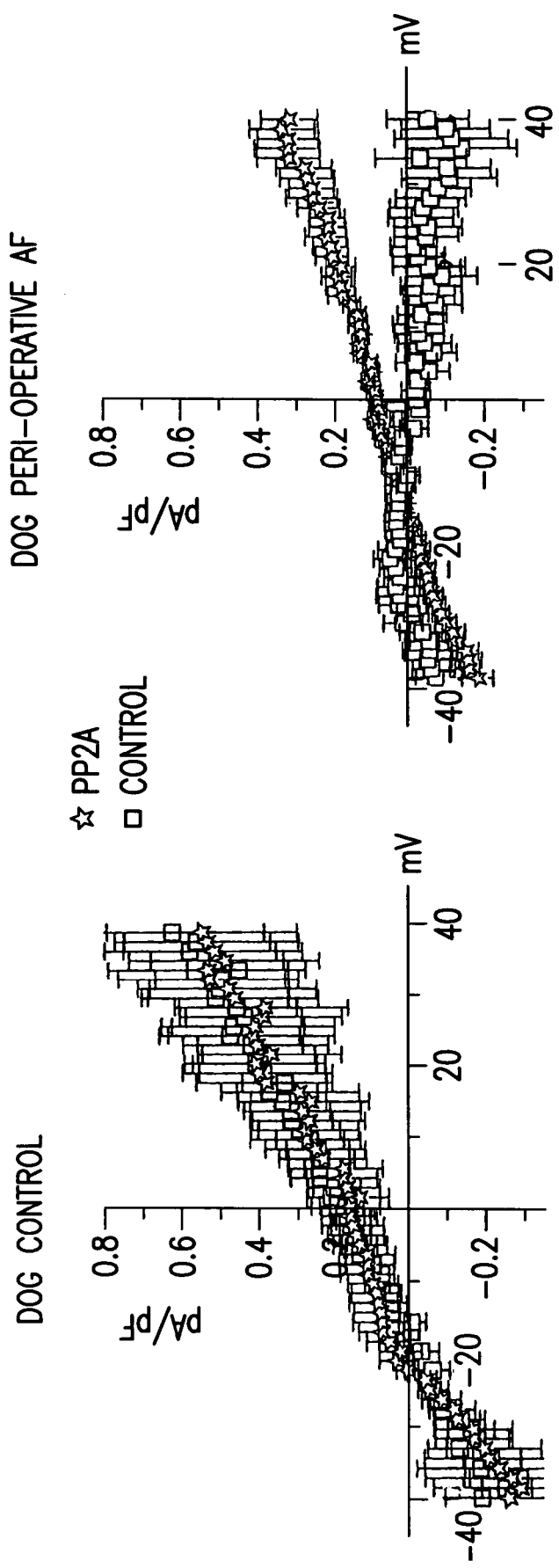
FIG. 26. Peri-operative atrial fibrillation (AF) occurs with a loss of TASK-1 current that can be rescued by protein phosphatase 2A. Peri-operative AF was induced by pacing three days after right atriotomy. Tissue was collected from the right atrium during the initial surgery (control) and again after AF was induced (AF). TASK-1 current was measured in myocytes isolated from before and after induction of AF. Cells were perfused with a modified Tyrode's solution to minimize other K currents. The perfusate contained: KCl 50 mM, CsCl 5 mM, TEA 1 mM and nifedipine 5 µM. Total current was measured using a ramp protocol from −50 mV to +30 mV in 6 s, and the TASK-1 current was defined as the methanandamide-sensitive current. The average TASK-1 current is shown from control tissue (9 cells from 4 dogs, left panel, squares) and after induction of AF (II cells from 4 dogs, right panel, squares). TASK-1 current is completely absent in the cells from the peri-operative AF condition but the current can be rescued adding a serine-threonine phosphatase, PP2A (1 U/ml, 10 min) to the patch pipette solution (10 cells from 4 dogs, right panel, stars). PP2A in the patch pipette has no effect on control cells (8 cells from 4 dogs, left panel, stars).

FIG. 26 demonstrates that peri-operative atrial fibrillation (AF), which occurs with a loss of TASK-1 current, can be rescued by protein phosphatase 2A. Peri-operative AF was induced by pacing three days after right atriotomy. Tissue was collected from the right atrium during the initial surgery (control) and again after AF was induced (AF). TASK-1 current was measured in myocytes isolated from before and after induction of AF. Cells were perfused with a modified Tyrode's solution to minimize other K currents. The perfusate contained: KCl 50 mM, CsCl 5 mM, TEA 1 mM and nifedipine 5 μM. Total current was measured using a ramp protocol from −50 mV to +30 mV in 6 s, and the TASK-1 current was defined as the methanandamide-sensitive current. The average TASK-1 current is shown from control tissue (9 cells from 4 dogs, left panel, squares) and after induction of AF (11 cells from 4 dogs, right panel, squares). TASK-1 current is completely absent in the cells from the peri-operative AF condition but the current can be rescued by adding a serine-threonine phosphatase, PP2A (1 U/ml, 10 min) to the patch pipette solution (10 cells from 4 dogs, right panel, stars). PP2A in the patch pipette has no effect on control cells (8 cells from 4 dogs, left panel, stars).

Figure 27:
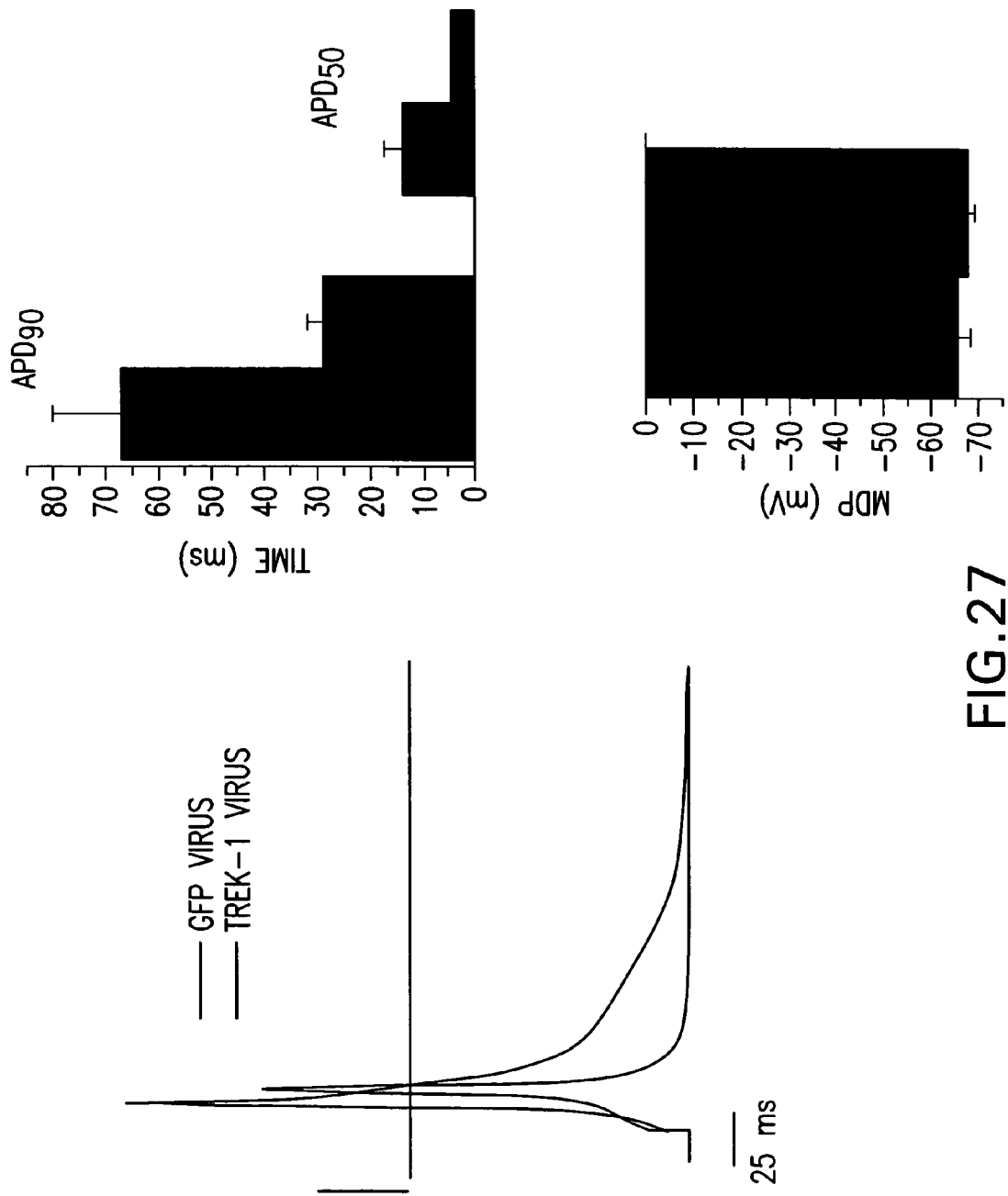
FIG. 27. TREK-1 expressing adenovirus causes expression of TREK-1 current and is associated with shortening of the action potential duration in cultured rat myocytes. Left panel: Cultured adult rat ventricular myocytes were infected with an adenovirus carrying either GFP or TREK-1. The action potential was recorded in current clamp mode with a stimulation rate of 1 Hz. Zero mV is indicated by the solid line. Right Panel: The action potential duration measured at 90% and 50% repolarization was significantly shorter when TREK-1 was overexpressed (top). The resting potential (MDP) was not changed by the expression of TREK-1 (bottom).

FIG. 27 depicts the results obtained from experiments utilizing a TREK-1 expressing adenovirus. The adenovirus mediated expression of TREK-1 causes expression of TREK-1 current and is associated with shortening of the action potential duration in cultured rat myocytes. FIG. 27, left panel, depicts results obtained when cultured adult rat ventricular myocytes were infected with an adenovirus carrying either GFP or TREK-1. The action potential was recorded in current clamp mode with a stimulation rate of 1 Hz. Zero mV is indicated by the solid line. FIG. 27, right panel, demonstrates that the action potential duration measured at 90% and 50% repolarization was significantly shorter when TREK-1 was overexpressed (top). The resting potential (MDP) was not changed by the expression of TREK-1 (bottom).

Figure 28:
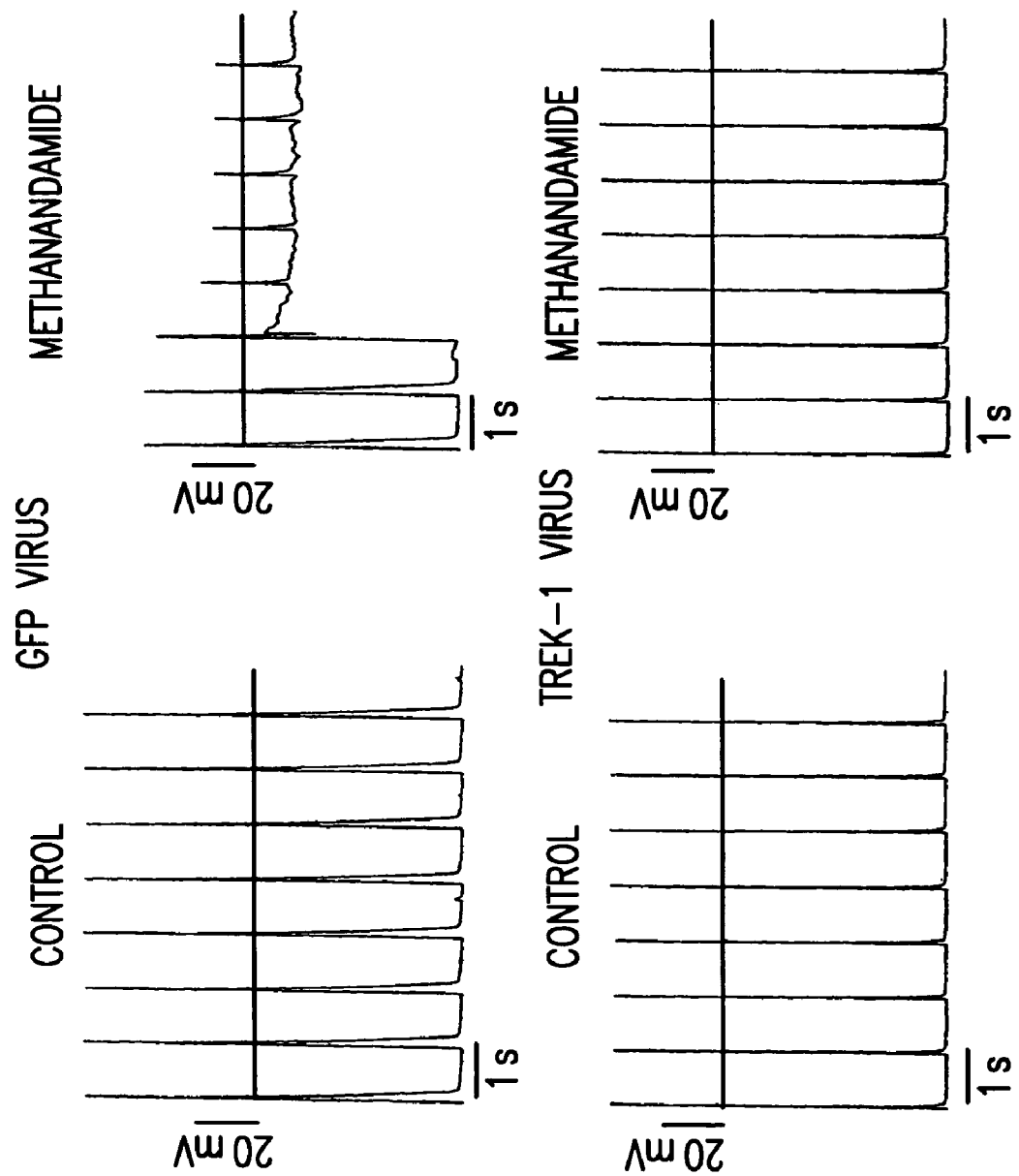
FIG. 28. Methanandamide-induced arrhythmias are prevented by over expression of TREK-1 in cultured myocytes. The action potentials of cultured adult rat ventricular myocytes were recorded in current clamp mode during stimulation at 1 Hz. When control cells expressing only GFP were superfused with TASK-1 inhibitor, methanandamide, typical arrythmias were observed (top right). However, when myocytes overexpress GFP and TREK-1, inhibition of TASK-1 is unable to induce arrhythmias.

FIG. 28 indicates that methanandamide-induced arrhythmias are prevented by over expression of TREK-1 in cultured myocytes. The action potentials of cultured adult rat ventricular myocytes were recorded in current clamp mode during stimulation at 1 Hz. When control cells expressing only GFP were superfused with TASK-1 inhibitor, methanandamide, typical arrythmias were observed (top right). However, when myocytes overexpress GFP and TREK-1, inhibition of TASK-1 is unable to induce arrhythmias.

Figure 29A:
FIG. 29. Treatment with ONO-RS-082 halts atrial fibrillation (AF) in a dog model. Peri-operative AF was induced in a dog three days after a right atriotomy by brief, rapid pacing. Routinely, this procedure results in AF that continues for at least 30 min and is only stopped by electrical cardioversion. Panel A depicts an EKG trace of the animal just prior to the induction of AF. This run of AF continued for 30 min and the animal was shocked into a normal sinus rhythm (NSR). After 15 min, a second run of AF was induced and a recording of the EKG obtained during this period of AF is shown in Panel B. 20 min later, ONO-RS-082 (0.7 mg/kg) was infused over 2 min. The heart rate slowed within 1 min of the administration of the drug and the EKG normalized within 5 min and persisted in NSR for over an hour at which point the experiment was terminated (Panel C).
Figure 29B:
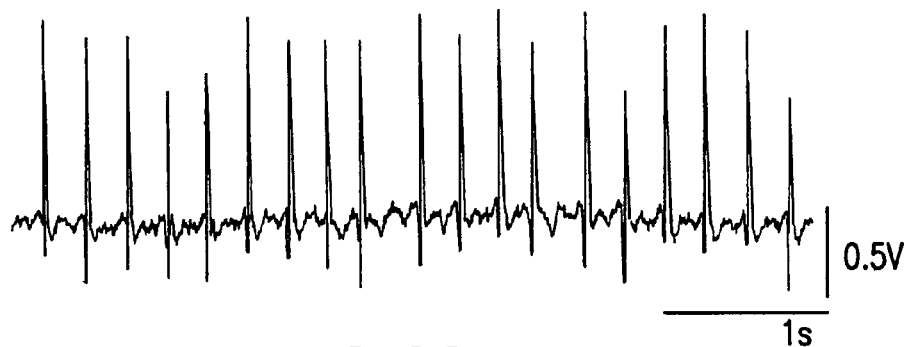
Figure 29C:

Furthermore, as depicted in FIG. 29, treatment with ONO-RS-082 halted atrial fibrillation (AF) in a dog model. Peri-operative AF was induced in a dog three days after a right atriotomy by brief, rapid pacing. Routinely, this procedure results in AF that continues for at least 30 min and is only stopped by electrical cardioversion. Panel A of FIG. 29 depicts an EKG trace of the animal just prior to the induction of AF. This run of AF continued for 30 min and the animal was shocked into a normal sinus rhythm (NSR). After 15 min, a second run of AF was induced and a recording of the EKG obtained during this period of AF is shown in Panel B. 20 min later, ONO-RS-082 (0.7 mg/kg) was infused over 2 min. Following administration of the drug, the heart rate slowed within 1 min of the administration of the drug and the EKG normalized within 5 min and persisted in NSR for over an hour at which point the experiment was terminated (FIG. 29, Panel C).

FIG. 30 demonstrates with single channel recordings that ONO-RS-082 activates TREK-1 in a cell-free patch. CHO cells were transfected with a plasmid that encodes the human TREK-1 channel. 48 h after transfection cells were used in the patch clamp experiments. Single channel recordings were obtained in the inside-out configuration holding the patch at −80 mV in symmetrical K⁺ (155 mM). FIG. 30, Panel A, shows a typical recording of the channel openings in CHO cell membrane under control conditions. FIG. 30, Panel B, shows an increase in single channel activity 1 min 30s after perfusion of the patch with 100 nM ONO-RS-082. This result is typical of at least 4 patches.

Example 4

Prostate Cancer

Prostate cancer is the most commonly diagnosed cancer in the US male population with over 230,000 new cases anticipated in 2004. In spite of advances in detection and treatment, prostate cancer is still expected to kill 30,000 Americans this year.

Tissue from human prostate carcinoma and from established prostate cancer cell lines, such as LNCaP and PC-3 cells, express 15-lipoxygenase 1 (15-LOX1), an enzyme that converts linoleic acid (LA) to 13(S)-hydroxyoctadecadienoic acid (13-HODE) (Spindler S. A. et al., (1997) Biochem Biophys Res Commun, 239:775-81). Normal prostatic tissue expresses a different isoform of this enzyme, 15-LOX2, which generally metabolizes arachidonic acid (AA) to 15 (S)-hydroxyeicosatetraenoic acid (15-HETE) (Shappell S. B. et al., (1999) Am J Pathol, 155:235-45). In fact, there is a strong positive correlation between the Gleason staging of a prostate carcinoma and the expression of 15-LOX1 (Kelavkar U. P. et al., (2000) Carcinogenesis, 21:1777-87). Conversely, the expression of the "normal" isoform, 15-LOX2 is strongly suppressed in prostate tumors and in prostate cancer cell lines (Tang S. et al., (2002) J Biol Chem, 277:16189-201, 2002). In vitro studies also demonstrated that the stable overexpression of 15-LOX1 in PC-3 cells increases cell proliferation and enhances the tumorigenicity of these cells when injected into nude mice (Kelavkar U. P. et al., (2001) Carcinogenesis, 22:1765-73) while expression of 15-LOX2 suppress cell proliferation (Tang S. et al., (2002) J Biol Chem, 277:16189-201, 2002). There is no settled mechanism to explain why 13-HODE is pro-tumorigenic or why 15-HETE suppresses tumor formation in the prostate but some (Hsi L C et al., (2002) J Biol Chem, 277:40549-56, 2002) have proposed that these lipids have opposing effects on mitogen-activated protein kinase (MAPK) signaling and ultimately alter the activity of peroxisome proliferator-activated receptor gamma.

Here a mechanism by which these lipids might alter cell proliferation is set forth. Recently, the two pore-domain potassium channels (2PK) have been identified as a new family of time- and voltage-independent channels that are responsible for background currents in a very wide variety of cells (reviewed in Lesage F and Lazdunski M, (2000) Am J Physiol Renal Physiol, 279:F793-801). Active 2PK channels are dimers formed from two subunits that each have four transmembrane segments and two pore-forming domains. These channels have a number of interesting properties, some being acid-sensitive, others respond to stretch or to various unsaturated fatty acids. In excitable cells, these channels help set the resting membrane potential but their role in tissues such as the prostate is less well defined. Of interest, is a recent finding that the 2PK channel, TASK-3, is over-expressed in a subset of breast, lung, colon and metastatic prostate carcinomas (Mu D et al., (2003) Cancer Cell, 3:297-302). This led to investigations by several groups that linked the expression of 2PK to the regulation of cell proliferation and tumorigenicity (Mu D et al., (2003) Cancer Cell, 3:297-302; Pei L et al., (2003) Proc Nat'l Acad Sci USA, 100:7803-7; Lauritzen I et al., (2003) J Biol Chem, 278:32068-76). Dominant-negative mutants of these channels were created by altering a single amino acid in the K$^+$ selectivity filter of the channel and in contrast, to the results with wild-type channels expression of dominant-negative mutants of 2PK abrogated the ability of the 2PK to affect cell proliferation in vitro, or the tumorigenic potential in nude mice. These results confirm that the effects on cell proliferation were dependent upon the function of these channels.

In heterologous expression studies of one 2PK, TREK-1, it has been observed that a divergence in the sensitivity of the channel to various lipoxygenase products exists. Specifically, the 15-LOX1 product, 13-HODE reduces current through the channel while 15-HPETE, a 15-LOX2 product, increases TREK-1 current. Thus, these results would suggest that abnormally elevated endogenous 13-HODS levels found in prostate cancer cells may lead to a significant impairment in 2PK channel function. Altered channel function may underlie some of the aberrant regulation of cell proliferation characteristic of the carcinoma cells. In addition, it has been observed that Northern analysis of normal prostate tissue show expression of TASK-1, TASK-3 and TREK-1 in prostate (Duprat F et al., (1991) EMBO J. 16:5464-71; Mu D et al., (2003) Cancer Cell, 3:297-302; Medhurst A D et al., (2001) Brain Res, 86:101-14).

Throughout this application, various publications are referenced in parentheses. The disclosures of these publications in their entireties are hereby incorporated by reference into this application to more fully describe the state of the art to which this invention pertains.

What is claimed is:

1. A method of treating an arrhythmia associated with phosphorylation of TASK-1 in a subject comprising administering to the subject an amount of a TREK-1 agonist effective to overcome the phosphorylation dependent loss of TASK-1 function so as to thereby treat the arrhythmia, wherein the TREK-1 agonist is a compound of the formula:

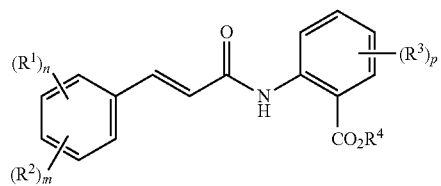

or a pharmaceutically acceptable ester or salt thereof, wherein:

R$^2$ selected from the group consisting of
—C$_1$ to C$_8$ alkyl,
—C$_2$ to C$_8$ alkenyl,
—O—(C$_1$ to C$_8$ alkyl),
—NH(C$_1$ to C$_8$ alkyl),
wherein each C$_1$ to C$_8$ alkyl and C$_2$ to C$_8$ alkenyl may be branched or unbranched and may be optionally substituted with one or more substituents selected from the group consisting of halo, lower alkoxy, oxo, CN, NO2, NH2, NH—(lower alkyl), N(lower alkyl)2, cycloalkyl, and aryl;

each R3 is independently selected from the group consisting of halo, lower alkyl, lower alkoxy, NH2, NH—(lower alkyl), N(lower alkyl)2, NO2, CN, CF3, and;

R4 is selected from the group consisting of H and lower alkyl; and n=0, m=0 to 2, and p=0 to 2.

2. The method of claim 1, wherein the arrhythmia is an atrial arrhythmia.

3. The method of claim 2, wherein the atrial arrhythmia is an atrial fibrillation.

4. The method of claim 3, wherein the atrial fibrillation is peri-operative atrial fibrillation.

5. The method of claim 1, wherein the arrhythmia is a post-ischemic arrhythmia.

6. The method of claim 1, wherein the arrhythmia is a ventricular arrhythmia.

7. A method of treating an arrhythmia associated with phosphorylation of TASK-1 in a subject comprising administering to the subject an amount of a TREK-1 agonist effective to overcome the phosphorylation dependent loss of TASK-1 function so as to thereby treat the arrhythmia, wherein the TREK-1 agonist is BML264 or BML263.

8. A method of treating an arrhythmia associated with phosphorylation of TASK-1 in a subject comprising administering to the subject an amount of a TREK-1 agonist effective to overcome the phosphorylation dependent loss of TASK-1 function so as to thereby treat the arrhythmia, wherein the TREK-1 agonist is ONO-RS-082.

9. The method of claim 1, wherein the TREK-1 agonist is a pharmaceutically acceptable salt thereof.

10. The method of claim 1, wherein the TREK-1 agonist is a pharmaceutically acceptable ester thereof.

* * * * *